(12) United States Patent
Friedland et al.

(10) Patent No.: US 9,913,678 B2
(45) Date of Patent: Mar. 13, 2018

(54) METHODS, APPARATUSES, AND SYSTEMS FOR REDUCING INTRAOCULAR PRESSURE AS A MEANS OF PREVENTING OR TREATING OPEN-ANGLE GLAUCOMA

(71) Applicant: TearScience, Inc., Morrisville, NC (US)

(72) Inventors: Beth Friedland, Raleigh, NC (US); Donald R. Korb, Boston, MA (US); Steve Grenon, Durham, NC (US); John Jans, Hillsborough, NC (US); Keith Gausmann, Cary, NC (US); Timothy R. Willis, Raleigh, NC (US)

(73) Assignee: TearScience, Inc., Morrisville, NC (US)

( * ) Notice: Subject to any disclaimer, the term of this patent is extended or adjusted under 35 U.S.C. 154(b) by 874 days.

(21) Appl. No.: 14/074,123

(22) Filed: Nov. 7, 2013

(65) Prior Publication Data

US 2014/0066821 A1 Mar. 6, 2014

Related U.S. Application Data

(60) Division of application No. 12/246,071, filed on Oct. 6, 2008, now abandoned, which is a
(Continued)

(51) Int. Cl.
*A61F 7/00* (2006.01)
*A61B 18/04* (2006.01)
(Continued)

(52) U.S. Cl.
CPC .......... *A61B 18/04* (2013.01); *A61F 9/00781* (2013.01); *A61H 1/008* (2013.01);
(Continued)

(58) Field of Classification Search
None
See application file for complete search history.

(56) References Cited

U.S. PATENT DOCUMENTS

| 168,352 A | 10/1875 | Sloan |
| 1,006,945 A | 10/1911 | Houston |

(Continued)

FOREIGN PATENT DOCUMENTS

| AU | 2011203832 A1 | 8/2012 |
| AU | 2011302478 A1 | 3/2013 |

(Continued)

OTHER PUBLICATIONS

Non-final Office Action for U.S. Appl. No. 12/246,071 dated Aug. 29, 2012, 17 pages.
(Continued)

*Primary Examiner* — Kaitlyn Smith
(74) *Attorney, Agent, or Firm* — Withrow & Terranova, PLLC

(57) ABSTRACT

Embodiments include methods, apparatuses, and systems for reducing elevated intraocular pressure (IOP) in a patient to either prevent or treat open-angle glaucoma. Heat is applied to the trabecular meshwork in the patient's eye without damaging proteins in the trabecular meshwork. The application of heat to the trabecular meshwork has the effect of relaxing or loosening protein clogs or other inhibitors in the trabecular meshwork, which are either reducing or obstructing of the outflow of aqueous humor, thereby increasing the patient's IOP and causing ocular hypertension (OHT). By loosening or relaxing clogs or other inhibitors in the trabecular meshwork, the outflow path for aqueous humor is increased or restored, which can lower IOP and either prevent or treat glaucoma. Force may also be applied to the patient's eye to apply pressure to the trabecular
(Continued)

meshwork to further assist in the loosening or relaxing of clogs or other inhibitors in the trabecular meshwork.

25 Claims, 22 Drawing Sheets

Related U.S. Application Data continuation-in-part of application No. 11/541,291, filed on Sep. 29, 2006, now Pat. No. 7,981,095, which is a continuation-in-part of application No. 11/434,033, filed on May 15, 2006, application No. 14/074,123, which is a continuation-in-part of application No. 11/541,308, filed on Sep. 29, 2006, which is a continuation-in-part of application No. 11/434,054, filed on May 15, 2006, now Pat. No. 8,083,787, application No. 14/074,123, which is a continuation-in-part of application No. 12/015,558, filed on Jan. 17, 2008, now Pat. No. 7,981,146.

(60) Provisional application No. 60/700,233, filed on Jul. 18, 2005, provisional application No. 60/880,850, filed on Jan. 17, 2007.

(51) Int. Cl.
*A61F 9/007* (2006.01)
*A61H 1/00* (2006.01)
*A61B 18/10* (2006.01)
*A61B 18/00* (2006.01)
*A61N 7/00* (2006.01)

(52) U.S. Cl.
CPC ..... *A61B 18/10* (2013.01); *A61B 2018/00642* (2013.01); *A61B 2018/00791* (2013.01); *A61B 2018/046* (2013.01); *A61B 2018/048* (2013.01); *A61F 2007/0004* (2013.01); *A61F 2007/0059* (2013.01); *A61F 2007/0071* (2013.01); *A61N 7/00* (2013.01)

(56) References Cited

U.S. PATENT DOCUMENTS

| | | | |
|---|---|---|---|
| 1,924,315 A | 8/1933 | Hemphill et al. |
| 2,545,724 A | 3/1951 | Curtis |
| 2,891,252 A | 6/1959 | Lazo |
| 3,140,390 A | 7/1964 | Smith et al. |
| 3,173,419 A | 3/1965 | Dubilier et al. |
| 3,333,586 A | 8/1967 | Bellis et al. |
| 3,404,678 A | 10/1968 | Ardenne |
| 3,411,364 A | 11/1968 | Horley et al. |
| 3,415,299 A | 12/1968 | Hinman, Jr. et al. |
| 3,667,476 A | 6/1972 | Muller |
| 3,915,346 A | 10/1975 | Allsop |
| 3,952,735 A | 4/1976 | Wirtschafter et al. |
| 4,069,084 A | 1/1978 | Mlodozeniec et al. |
| 4,131,115 A | 12/1978 | Peng |
| 4,261,364 A | 4/1981 | Haddad et al. |
| 4,387,707 A | 6/1983 | Polikoff |
| 4,612,959 A | 9/1986 | Costello |
| 4,778,457 A | 10/1988 | York |
| 4,883,454 A | 11/1989 | Hamburg |
| 4,914,088 A | 4/1990 | Glonek et al. |
| 4,918,818 A | 4/1990 | Hsieh |
| 4,955,377 A | 9/1990 | Lennox et al. |
| 4,958,632 A | 9/1990 | Duggan |
| 5,020,455 A | 6/1991 | Takashi et al. |
| 5,030,214 A | 7/1991 | Spector |
| 5,097,829 A | 3/1992 | Quisenberry |
| 5,151,100 A | 9/1992 | Abele et al. |
| 5,158,082 A | 10/1992 | Jones |
| 5,169,384 A | 12/1992 | Bosniak et al. |
| 5,213,097 A | 5/1993 | Zeindler |
| 5,251,627 A | 10/1993 | Morris |
| 5,283,063 A | 2/1994 | Freeman |
| 5,314,456 A | 5/1994 | Cohen |
| 5,327,886 A | 7/1994 | Chiu |
| 5,343,561 A | 9/1994 | Adamo |
| D352,106 S | 11/1994 | Fanney et al. |
| 5,368,582 A | 11/1994 | Bertera |
| 5,368,591 A | 11/1994 | Lennox et al. |
| 5,377,701 A | 1/1995 | Fang |
| 5,419,772 A | 5/1995 | Teitz et al. |
| 5,425,380 A | 6/1995 | Hudson et al. |
| 5,496,311 A | 3/1996 | Abele et al. |
| 5,601,548 A | 2/1997 | Smith et al. |
| 5,628,772 A | 5/1997 | Russell |
| 5,643,336 A | 7/1997 | Lopez-Claros |
| 5,690,123 A | 11/1997 | Medina |
| 5,700,238 A | 12/1997 | Hyson |
| 5,720,773 A | 2/1998 | Lopez-Claros |
| 5,769,806 A | 6/1998 | Radow |
| 5,782,857 A | 7/1998 | Machuron |
| 5,795,312 A | 8/1998 | Dye |
| 5,807,302 A | 9/1998 | Wandel |
| 5,807,357 A | 9/1998 | Kang |
| 5,836,927 A | 11/1998 | Fried |
| 5,893,719 A | 4/1999 | Radow |
| 5,958,912 A | 9/1999 | Sullivan |
| 5,960,608 A | 10/1999 | Ohtonen |
| 5,964,723 A | 10/1999 | Augustine |
| 6,007,501 A | 12/1999 | Cabados et al. |
| 6,024,095 A | 2/2000 | Stanley, III |
| 6,041,821 A | 3/2000 | Grossman |
| 6,059,772 A | 5/2000 | Hsia et al. |
| 6,090,060 A | 7/2000 | Radow |
| 6,107,289 A | 8/2000 | Sullivan |
| 6,110,292 A | 8/2000 | Jewett et al. |
| 6,112,900 A | 9/2000 | Adkins, Jr. |
| 6,113,561 A | 9/2000 | Augustine |
| 6,143,010 A | 11/2000 | Silvestrini et al. |
| 6,153,607 A | 11/2000 | Pflugfelder et al. |
| 6,155,995 A | 12/2000 | Lin |
| 6,181,970 B1 | 1/2001 | Kasevich |
| 6,193,740 B1 | 2/2001 | Rodriguez |
| 6,206,842 B1 | 3/2001 | Tu et al. |
| 6,213,966 B1 | 4/2001 | Augustine |
| 6,273,886 B1 | 8/2001 | Edwards et al. |
| 6,275,735 B1 | 8/2001 | Jarding et al. |
| 6,309,364 B1 | 10/2001 | Cathaud et al. |
| 6,312,397 B1 | 11/2001 | Gebhard |
| D456,079 S | 4/2002 | Fujii |
| 6,423,018 B1 | 7/2002 | Augustine |
| 6,425,883 B1 | 7/2002 | Urich et al. |
| 6,425,888 B1 | 7/2002 | Embleton et al. |
| 6,428,508 B1 | 8/2002 | Ross |
| 6,436,128 B1 | 8/2002 | Usui |
| 6,438,398 B1 | 8/2002 | Pflugfelder et al. |
| 6,455,583 B1 | 9/2002 | Pflugfelder et al. |
| 6,482,203 B2 | 11/2002 | Paddock et al. |
| 6,490,488 B1 | 12/2002 | Rudie et al. |
| D472,637 S | 4/2003 | Cooper et al. |
| 6,544,193 B2 | 4/2003 | Abreu |
| 6,544,257 B2 | 4/2003 | Nagase et al. |
| D477,084 S | 7/2003 | Menezes et al. |
| 6,641,264 B1 | 11/2003 | Schwebel |
| 6,648,904 B2 | 11/2003 | Altshuler et al. |
| 6,706,001 B2 | 3/2004 | Fresco |
| 6,780,176 B2 | 8/2004 | Hasegawa |
| 6,788,977 B2 | 9/2004 | Fenn et al. |
| 6,827,898 B1 | 12/2004 | Fausset et al. |
| 6,840,954 B2 | 1/2005 | Dietz et al. |
| 6,860,852 B2 | 3/2005 | Schonenberger et al. |
| 6,860,880 B2 | 3/2005 | Treat et al. |
| 6,874,884 B2 | 4/2005 | Schwebel |
| 6,882,885 B2 | 4/2005 | Levy, Jr. et al. |
| 6,886,933 B2 | 5/2005 | Schwebel |
| 6,899,694 B2 | 5/2005 | Kadziauskas et al. |
| 6,908,195 B2 | 6/2005 | Fuller |
| 6,925,317 B1 | 8/2005 | Samuels et al. |
| 6,955,656 B2 | 10/2005 | Bergheim et al. |

(56) References Cited

U.S. PATENT DOCUMENTS

| | | |
|---|---|---|
| 6,974,454 B2 | 12/2005 | Hooven |
| 6,986,753 B2 | 1/2006 | Bui |
| 6,989,007 B2 | 1/2006 | Shadduck |
| 7,001,379 B2 | 2/2006 | Behl et al. |
| 7,004,942 B2 | 2/2006 | Laird et al. |
| 7,018,355 B2 | 3/2006 | Kadziauskas et al. |
| 7,036,928 B2 | 5/2006 | Schwebel |
| 7,060,061 B2 | 6/2006 | Altshuler et al. |
| 7,069,084 B2 | 6/2006 | Yee |
| 7,083,783 B2 | 8/2006 | Kaufman et al. |
| 7,084,128 B2 | 8/2006 | Yerxa et al. |
| 7,094,225 B2 | 8/2006 | Tu et al. |
| 7,108,694 B2 | 9/2006 | Miura et al. |
| 7,118,591 B2 | 10/2006 | Frank et al. |
| 7,122,013 B2 | 10/2006 | Liu |
| 7,122,047 B2 | 10/2006 | Grahn et al. |
| 7,123,968 B1 | 10/2006 | Casscells, III et al. |
| 7,146,209 B2 | 12/2006 | Gross et al. |
| 7,186,232 B1 | 3/2007 | Smedley et al. |
| 7,211,070 B2 | 5/2007 | Soroudi |
| 7,229,468 B2 | 6/2007 | Wong, Jr. et al. |
| 7,231,922 B2 | 6/2007 | Davison et al. |
| D546,459 S | 7/2007 | Banryu |
| 7,273,475 B2 | 9/2007 | Tu et al. |
| D552,736 S | 10/2007 | Yamaoka |
| D553,750 S | 10/2007 | Yamaoka |
| 7,316,657 B2 | 1/2008 | Kleinhenz et al. |
| 7,357,500 B2 | 4/2008 | Schwebel |
| 7,384,405 B2 | 6/2008 | Rhoades |
| 7,442,174 B2 | 10/2008 | Butler |
| 7,513,893 B2 | 4/2009 | Soroudi |
| 7,559,907 B2 | 7/2009 | Krempel et al. |
| 7,594,728 B2 | 9/2009 | Seal et al. |
| 7,637,878 B2 | 12/2009 | Lin |
| D612,941 S | 3/2010 | Youngquist et al. |
| D614,774 S | 4/2010 | Gausmann et al. |
| 7,712,899 B2 | 5/2010 | Tanassi et al. |
| 7,976,573 B2 | 7/2011 | Korb et al. |
| 7,981,146 B2 | 7/2011 | Korb et al. |
| 7,981,147 B2 | 7/2011 | Korb et al. |
| 8,007,524 B2 | 8/2011 | Korb et al. |
| D645,565 S | 9/2011 | Smith et al. |
| 8,025,689 B2 | 9/2011 | Korb et al. |
| 8,083,787 B2 | 12/2011 | Korb et al. |
| 8,128,673 B2 | 3/2012 | Korb et al. |
| 8,128,674 B2 | 3/2012 | Korb et al. |
| 8,137,390 B2 | 3/2012 | Korb et al. |
| 8,187,310 B2 | 5/2012 | Korb et al. |
| 8,187,311 B2 | 5/2012 | Korb et al. |
| 8,262,715 B2 | 9/2012 | Wong, Jr. et al. |
| 8,455,016 B2 | 6/2013 | Maskin |
| 8,491,508 B2 | 7/2013 | Smith et al. |
| 8,617,229 B2 | 12/2013 | Korb et al. |
| 8,628,504 B2 | 1/2014 | Grenon et al. |
| 8,791,158 B2 | 7/2014 | Dalton et al. |
| 8,906,427 B2 | 12/2014 | Maskin |
| 8,925,484 B2 | 1/2015 | Maier, Jr. et al. |
| 9,039,718 B2 | 5/2015 | Rynerson |
| 9,510,972 B2 | 12/2016 | Badawi |
| 9,763,827 B2 | 9/2017 | Kelleher et al. |
| 9,822,142 B2 | 11/2017 | Cavanagh et al. |
| 2001/0016707 A1 | 8/2001 | Urich et al. |
| 2001/0039442 A1 | 11/2001 | Gorge et al. |
| 2001/0041886 A1 | 11/2001 | Durkin et al. |
| 2002/0013572 A1* | 1/2002 | Berlin ............ A61F 2/15 606/4 |
| 2002/0019607 A1 | 2/2002 | Bui |
| 2002/0035345 A1 | 3/2002 | Beck |
| 2002/0099094 A1 | 7/2002 | Anderson |
| 2002/0111608 A1 | 8/2002 | Baerveldt et al. |
| 2002/0128696 A1 | 9/2002 | Pearl et al. |
| 2002/0151835 A1 | 10/2002 | Ross |
| 2002/0156402 A1 | 10/2002 | Woog et al. |
| 2002/0169130 A1 | 11/2002 | Tu et al. |
| 2003/0050594 A1 | 3/2003 | Zamierowski |
| 2003/0056281 A1 | 3/2003 | Hasegawa |
| 2003/0065277 A1 | 4/2003 | Covington |
| 2003/0073987 A1 | 4/2003 | Sakurai et al. |
| 2003/0088241 A1 | 5/2003 | Hasegawa |
| 2003/0097151 A1 | 5/2003 | Smedley |
| 2003/0100936 A1 | 5/2003 | Altshuler et al. |
| 2003/0114426 A1 | 6/2003 | Pflugfelder et al. |
| 2003/0139790 A1 | 7/2003 | Ingle et al. |
| 2003/0195438 A1* | 10/2003 | Petillo ............ A61H 5/00 601/15 |
| 2003/0211043 A1 | 11/2003 | Korb |
| 2003/0233135 A1 | 12/2003 | Yee |
| 2004/0064169 A1 | 4/2004 | Briscoe et al. |
| 2004/0064171 A1 | 4/2004 | Briscoe et al. |
| 2004/0076695 A1 | 4/2004 | Gilbard |
| 2004/0097868 A1 | 5/2004 | Kadziauskas et al. |
| 2004/0097869 A1 | 5/2004 | Kadziauskas et al. |
| 2004/0097870 A1 | 5/2004 | Kadziauskas et al. |
| 2004/0111138 A1 | 6/2004 | Bleam et al. |
| 2004/0153093 A1 | 8/2004 | Donovan |
| 2004/0162545 A1 | 8/2004 | Brown et al. |
| 2004/0186534 A1 | 9/2004 | Shadduck |
| 2004/0193095 A1 | 9/2004 | Shadduck |
| 2004/0193262 A1 | 9/2004 | Shadduck |
| 2004/0199158 A1 | 10/2004 | Hood et al. |
| 2004/0237969 A1 | 12/2004 | Fuller |
| 2004/0249427 A1 | 12/2004 | Nabilsi |
| 2004/0260209 A1 | 12/2004 | Ella et al. |
| 2005/0022823 A1 | 2/2005 | Davison et al. |
| 2005/0096639 A1* | 5/2005 | Slatkine ............ A61F 9/00802 606/5 |
| 2005/0119629 A1 | 6/2005 | Soroudi |
| 2005/0125003 A1 | 6/2005 | Pinchuk et al. |
| 2005/0143798 A1 | 6/2005 | Bleam et al. |
| 2005/0187502 A1 | 8/2005 | Krempel et al. |
| 2005/0220742 A1 | 10/2005 | Breen |
| 2005/0234506 A1 | 10/2005 | Weser |
| 2005/0250788 A1 | 11/2005 | Tu et al. |
| 2006/0018953 A1 | 1/2006 | Guillon |
| 2006/0030604 A1 | 2/2006 | Elsinger et al. |
| 2006/0047263 A1 | 3/2006 | Tu et al. |
| 2006/0055878 A1 | 3/2006 | Yee |
| 2006/0069420 A1 | 3/2006 | Rademacher et al. |
| 2006/0104914 A1 | 5/2006 | Soroudi |
| 2006/0116626 A1 | 6/2006 | Smedley et al. |
| 2006/0135890 A1 | 6/2006 | Tsai |
| 2006/0136022 A1 | 6/2006 | Wong et al. |
| 2006/0139569 A1 | 6/2006 | Schwebel |
| 2006/0154901 A1 | 7/2006 | Pflugfelder et al. |
| 2006/0157064 A1 | 7/2006 | Davison |
| 2006/0183698 A1 | 8/2006 | Abelson |
| 2006/0200113 A1 | 9/2006 | Haffner et al. |
| 2006/0212101 A1 | 9/2006 | Cheng |
| 2006/0233859 A1 | 10/2006 | Whitcup et al. |
| 2007/0016254 A1 | 1/2007 | Grenon et al. |
| 2007/0016256 A1 | 1/2007 | Korb et al. |
| 2007/0027411 A1 | 2/2007 | Ella et al. |
| 2007/0049913 A1 | 3/2007 | Grenon et al. |
| 2007/0088415 A1* | 4/2007 | Peyman ............ A61F 7/02 607/108 |
| 2007/0106349 A1 | 5/2007 | Kami et al. |
| 2007/0129711 A1 | 6/2007 | Altshuler et al. |
| 2007/0173799 A1 | 7/2007 | Hsia |
| 2007/0203462 A1 | 8/2007 | Soroudi |
| 2007/0203478 A1 | 8/2007 | Herekar |
| 2007/0270760 A1 | 11/2007 | Dacquay et al. |
| 2007/0280924 A1 | 12/2007 | Daniels et al. |
| 2007/0282280 A1 | 12/2007 | Tennican |
| 2008/0015488 A1 | 1/2008 | Tu et al. |
| 2008/0051681 A1* | 2/2008 | Schwartz ............ A61F 9/00781 601/2 |
| 2008/0051741 A1 | 2/2008 | Grenon et al. |
| 2008/0075787 A1 | 3/2008 | Hibino |
| 2008/0081999 A1 | 4/2008 | Gravely et al. |
| 2008/0114311 A1 | 5/2008 | Muri et al. |
| 2008/0114312 A1 | 5/2008 | Muri et al. |
| 2008/0114421 A1 | 5/2008 | Korb et al. |
| 2008/0114423 A1 | 5/2008 | Grenon et al. |
| 2008/0114425 A1 | 5/2008 | Korb et al. |

(56) References Cited

U.S. PATENT DOCUMENTS

| | | | |
|---|---|---|---|
| 2008/0114426 | A1 | 5/2008 | Korb et al. |
| 2008/0132973 | A1 | 6/2008 | Lord et al. |
| 2008/0132978 | A1 | 6/2008 | Korb et al. |
| 2008/0188839 | A1 | 8/2008 | Chan et al. |
| 2008/0200848 | A1 | 8/2008 | Avni |
| 2008/0221649 | A1 | 9/2008 | Echague et al. |
| 2008/0251085 | A1 | 10/2008 | Schwebel |
| 2009/0043365 | A1 | 2/2009 | Friedland et al. |
| 2009/0137533 | A1 | 5/2009 | Adkins, Jr. |
| 2009/0149930 | A1 | 6/2009 | Schenck |
| 2009/0192478 | A1 | 7/2009 | Soroudi |
| 2009/0306111 | A1 | 12/2009 | Nakamura et al. |
| 2009/0306607 | A1 | 12/2009 | Yasuhiro |
| 2010/0087899 | A1 | 4/2010 | Erez et al. |
| 2010/0100029 | A1 | 4/2010 | Maskin |
| 2010/0292630 | A1 | 11/2010 | Maskin |
| 2011/0022010 | A1 | 1/2011 | Grenon et al. |
| 2011/0039805 | A1 | 2/2011 | Pflugfelder et al. |
| 2011/0059902 | A1 | 3/2011 | Sullivan et al. |
| 2011/0059925 | A1 | 3/2011 | Donnenfeld |
| 2011/0124725 | A1 | 5/2011 | Maskin |
| 2011/0130729 | A1 | 6/2011 | Korb et al. |
| 2011/0172302 | A1 | 7/2011 | Dalton et al. |
| 2011/0203832 | A1 | 8/2011 | Schrock |
| 2011/0251532 | A1 | 10/2011 | Yang |
| 2011/0273550 | A1 | 11/2011 | Amano et al. |
| 2011/0294897 | A1 | 12/2011 | Aberg et al. |
| 2012/0003296 | A1 | 1/2012 | Shantha et al. |
| 2012/0004320 | A1 | 1/2012 | Gao et al. |
| 2012/0065556 | A1 | 3/2012 | Smith et al. |
| 2012/0093876 | A1 | 4/2012 | Ousler, III et al. |
| 2012/0109041 | A1 | 5/2012 | Munz |
| 2012/0128763 | A1 | 5/2012 | Maskin |
| 2012/0209154 | A1 | 8/2012 | Williams, III et al. |
| 2012/0220612 | A1 | 8/2012 | Nakamura et al. |
| 2012/0321673 | A1 | 12/2012 | Ogawa et al. |
| 2013/0045927 | A1 | 2/2013 | Dana et al. |
| 2013/0046367 | A1 | 2/2013 | Chen |
| 2013/0053733 | A1 | 2/2013 | Korb et al. |
| 2013/0065867 | A1 | 3/2013 | Smith et al. |
| 2013/0110101 | A1 | 5/2013 | Van Valen et al. |
| 2013/0131171 | A1 | 5/2013 | Maskin |
| 2013/0172790 | A1 | 7/2013 | Badawi |
| 2013/0172829 | A1 | 7/2013 | Badawi |
| 2014/0330129 | A1 | 11/2014 | Grenon et al. |
| 2014/0378878 | A1 | 12/2014 | Sharma et al. |
| 2015/0005750 | A1 | 1/2015 | Kelleher et al. |
| 2015/0038851 | A1 | 2/2015 | Hamrah et al. |
| 2015/0057701 | A1 | 2/2015 | Kelleher et al. |
| 2015/0100001 | A1 | 4/2015 | Bujak |
| 2015/0148711 | A1 | 5/2015 | Bujak et al. |
| 2015/0174425 | A1 | 6/2015 | Toyos et al. |
| 2015/0182415 | A1 | 7/2015 | Olkowski et al. |
| 2015/0320590 | A1 | 11/2015 | Whitehurst et al. |
| 2015/0320594 | A1 | 11/2015 | Smith |
| 2016/0120692 | A1 | 5/2016 | Chen |
| 2016/0120693 | A1 | 5/2016 | Guillon et al. |
| 2016/0317379 | A1 | 11/2016 | Mosaddegh |
| 2017/0014300 | A1 | 1/2017 | Dippo et al. |
| 2017/0079834 | A1 | 3/2017 | Badawi |
| 2017/0079842 | A1 | 3/2017 | Maskin |

FOREIGN PATENT DOCUMENTS

| | | | |
|---|---|---|---|
| CA | 2331257 | A1 | 11/1999 |
| CA | 2679448 | A1 | 9/2008 |
| CA | 2787114 | A1 | 7/2011 |
| CA | 2809274 | A1 | 3/2012 |
| CN | 2650737 | Y | 10/2004 |
| CN | 1631344 | A | 6/2005 |
| CN | 2855388 | Y | 1/2007 |
| CN | 102204854 | A | 10/2011 |
| CN | 101663064 | B | 3/2013 |
| CN | 103002737 | A | 3/2013 |
| CN | 103108669 | A | 5/2013 |
| CN | 102600008 | B | 5/2014 |
| CN | 103816033 | A | 5/2014 |
| CN | 103948490 | A | 7/2014 |
| CN | 102697593 | B | 12/2014 |
| CN | 102697595 | B | 12/2014 |
| CN | 104203190 | A | 12/2014 |
| CN | 104398234 | A | 3/2015 |
| DE | 202005011496 | U1 | 7/2006 |
| EP | 0993814 | A1 | 4/2000 |
| EP | 1816980 | A2 | 8/2007 |
| EP | 2151438 | A1 | 2/2010 |
| EP | 1587468 | B1 | 1/2011 |
| EP | 2523556 | A1 | 11/2012 |
| JP | 0370557 | A | 3/1991 |
| JP | 06269473 | A | 9/1994 |
| JP | 06315499 | A | 11/1994 |
| JP | 10085248 | A | 4/1998 |
| JP | 11221247 | A | 8/1999 |
| JP | 2000225141 | A | 8/2000 |
| JP | 2001276113 | A | 10/2001 |
| JP | 2002078727 | A | 3/2002 |
| JP | 2004350803 | A | 12/2004 |
| JP | 3112008 | B | 7/2005 |
| JP | 2005237724 | A | 9/2005 |
| JP | 2006198249 | A | 8/2006 |
| JP | 2010155012 | A | 7/2010 |
| JP | 2014205069 | A | 10/2014 |
| KR | 20120115380 | A | 10/2012 |
| MX | 2012008110 | A | 10/2012 |
| WO | 9810723 | A1 | 3/1998 |
| WO | 9920213 | A1 | 4/1999 |
| WO | 9958131 | A1 | 11/1999 |
| WO | 0187380 | A1 | 11/2001 |
| WO | 02089699 | A2 | 11/2002 |
| WO | 2004041134 | A1 | 5/2004 |
| WO | 2004043217 | A2 | 5/2004 |
| WO | 2004073564 | A2 | 9/2004 |
| WO | 2006020003 | A2 | 2/2006 |
| WO | 2006058189 | A2 | 6/2006 |
| WO | 2006093851 | A2 | 9/2006 |
| WO | 2006129308 | A1 | 12/2006 |
| WO | 2008024100 | A2 | 2/2008 |
| WO | 2008106228 | A2 | 9/2008 |
| WO | 2009064834 | A2 | 5/2009 |
| WO | 2010005527 | A1 | 1/2010 |
| WO | 2010056848 | A1 | 5/2010 |
| WO | 2011085385 | A1 | 7/2011 |
| WO | 2012036931 | A1 | 3/2012 |
| WO | 2012051313 | A2 | 4/2012 |
| WO | 2012137545 | A1 | 10/2012 |
| WO | 2013003594 | A3 | 1/2013 |
| WO | 2013003731 | A3 | 1/2013 |
| WO | 2013006574 | A1 | 1/2013 |
| WO | 2013036894 | A2 | 3/2013 |
| WO | 2013114127 | A1 | 8/2013 |
| WO | 2013126599 | A1 | 8/2013 |
| WO | 2013149318 | A1 | 10/2013 |
| WO | 2013166353 | A1 | 11/2013 |
| WO | 2014049841 | A1 | 4/2014 |
| WO | 2014158356 | A1 | 10/2014 |
| WO | 2014179356 | A1 | 11/2014 |
| WO | 2014179795 | A2 | 11/2014 |
| WO | 2015163821 | A1 | 10/2015 |
| WO | 2016070134 | A1 | 5/2016 |
| WO | 2017072575 | A1 | 5/2017 |
| WO | 2017100608 | A1 | 6/2017 |
| WO | 2017156002 | A1 | 9/2017 |
| WO | 2017178892 | A3 | 11/2017 |

OTHER PUBLICATIONS

Non-final Office Action for U.S. Appl. No. 13/368,976 dated Aug. 31, 2012, 10 pages.

Non-final Office Action for U.S. Appl. No. 11/541,308 dated Aug. 31, 2012, 20 pages.

Non-final Office Action for U.S. Appl. No. 13/367,865 dated Sep. 13, 2012, 9 pages.

(56) References Cited

OTHER PUBLICATIONS

Non-final Office Action for U.S. Appl. No. 13/367,908 dated Sep. 13, 2012, 11 pages.
Extended European Search Report for patent application 07716441.6 dated Sep. 4, 2012, 7 pages.
Non-final Office Action for U.S. Appl. No. 11/931,398 dated Nov. 2, 2012, 8 pages.
Non-final Office Action for U.S. Appl. No. 11/928,681 dated Nov. 20, 2012, 10 pages.
European Search Report for patent application 06801969.4 dated Nov. 5, 2012, 4 pages.
Examination Report for Indian patent application 563/MUMNP/2009 dated Oct. 31, 2012, 1 pages.
Office Action for Japanese patent application 2009-546506 dated Sep. 4, 2012, 6 pages.
Examination Report dated Oct. 17, 2012, for European Application No. 07716444.0, 5 pages.
Examination Report dated Nov. 16, 2012, for European Application No. 06801969.4, 6 pages.
Non-Final Rejection dated Dec. 27, 2012, for U.S. Appl. No. 12/015,593, 27 pages.
Final Rejection dated Dec. 27, 2012, for U.S. Appl. No. 13/183,901, 10 pages.
Non-Final Rejection dated Jan. 4, 2013, for U.S. Appl. No. 12/015,600, 8 pages.
International Search Report dated Jan. 7, 2013, for PCT/US12/44650, 44 pages.
Non-Final Rejection for U.S. Appl. No. 11/928,681, dated Nov. 20, 2012, 9 pages.
Final Rejection for U.S. Appl. No. 13/242,068, dated Feb. 14, 2013, 10 pages.
Examination Report for Indian Patent Application No. 564/MUMNP/2009, dated Jan. 30, 2013, 1 page.
European Search Report for European Patent Application No. 08727830.5 dated Dec. 20, 2012, 3 pages.
Examination Report for European Patent Application No. 08727830.5 dated Jan. 15, 2013, 5 pages.
Final Office Action for U.S. Appl. No. 11/928,681 dated Feb. 26, 2013, 7 pages.
Advisory Action for U.S. Appl. No. 11/928,681 dated May 3, 2013, 3 pages.
Final Office Action for U.S. Appl. No. 11/541,308 dated Mar. 19, 2013, 25 pages.
Advisory Action for U.S. Appl. No. 11/541,308 dated Jun. 26, 2013, 3 pages.
Final Office Action for U.S. Appl. No. 11/931,398 dated Mar. 4, 2013, 7 pages.
Advisory Action for U.S. Appl. No. 11/931,398 dated May 15, 2013, 2 pages.
English translation of Final Japanese Office Action for patent application 2009-544825 dated Jan. 29, 2013, 4 pages.
English translation of Final Japanese Office Action for patent application 2009-525537 dated Jan. 29, 2013, 4 pages.
Examination Report for Indian Patent Application No. 555/MUMNP/2009, dated Apr. 15, 2013, 1 page.
Advisory Action for U.S. Appl. No. 13/183,901 dated Mar. 11, 2013, 3 pages.
Final Office Action for U.S. Appl. No. 12/368,976 dated Mar. 11, 2013, 8 pages.
Final Office Action for U.S. Appl. No. 13/242,068 dated Feb. 14, 2013, 10 pages.
Final Office Action for U.S. Appl. No. 13/367,865 dated Mar. 4, 2013, 7 pages.
Notice of Allowance for U.S. Appl. No. 13/367,865 dated May 23, 2013, 9 pages.
Final Office Action for U.S. Appl. No. 13/367,908 dated Feb. 27, 2013, 7 pages.
Advisory Action for U.S. Appl. No. 13/367,908 dated May 22, 2013, 3 pages.
Non-final Office Action for U.S. Appl. No. 12/887,165 dated Apr. 10, 2013, 13 pages.
Translation of Notice of Rejection for Japanese Patent Application No. 2009-525529 dated May 14, 2013, 5 pages.
Final Office Action for U.S. Appl. No. 12/246,071 dated May 7, 2013, 16 pages.
Non-final Office Action for U.S. Appl. No. 12/015,600 dated Aug. 5, 2013, 8 pages.
Notice of Allowance for U.S. Appl. No. 12/887,165 dated Sep. 3, 2013, 10 pages.
Advisory Action for U.S. Appl. No. 13/368,976 dated Jul. 10, 2013, 3 pages.
Non-final Office Action for U.S. Appl. No. 13/242,068 dated Jul. 3, 2013, 7 pages.
Notice of Allowance for U.S. Appl. No. 13/367,908 dated Aug. 19, 2013, 8 pages.
Notice of Allowance for U.S. Appl. No. 13/368,976 dated Aug. 30, 2013, 9 pages.
Final Office Action for U.S. Appl. No. 12/015,593 dated Oct. 3, 2013, 21 pages.
Advisory Action for U.S. Appl. No. 12/015,593 dated Dec. 13, 2013, 3 pages.
Non-final Office Action for U.S. Appl. No. 13/183,901 dated Oct. 4, 2013, 10 pages.
Notice of Allowance for U.S. Appl. No. 13/242,068 dated Nov. 12, 2013, 10 pages.
International Preliminary Report on Patentability for PCT/US2012/044650 dated Jan. 16, 2014, 41 pages.
First Office Action for Chinese patent application 201210077169.8 dated Nov. 26, 2013, 18 pages.
First Office Action for Chinese patent application 201210077192.7 dated Nov. 22, 2013, 12 pages.
Liu, Ze-Yuan et al., "Treatment of dry eye caused by meibomian gland dysfunction," International Eye Science, vol. 14, No. 2, Feb. 2014, pp. 270-272.
Non-final Office Action for U.S. Appl. No. 11/434,033 dated Feb. 19, 2014, 10 pages.
Examiner's Decision of Rejection for Japanese Patent Application No. 2009-544825 dated Jan. 7, 2014, 6 pages.
Examiner's Decision of Rejection for Japanese Patent Application No. 2009-525537 dated Jan. 7, 2014, 6 pages.
Final Office Action for U.S. Appl. No. 13/183,901 dated Feb. 3, 2014, 10 pages.
Lu, Hui et al., "Tear film measurement by optical reflectometry technique," Journal of Biomedical Optics, vol. 19, No. 2, Feb. 2014, 8 pages.
Non-final Office Action for U.S. Appl. No. 12/015,593 dated Mar. 14, 2014, 19 pages.
First Office Action for Chinese patent application 201210127347.3 dated Jan. 15, 2014, 13 pages.
Purslow, Christine, "Evaluation of the ocular tolerance of a novel eyelid-warming device used for meibomian gland dysfunction," Contact Lens & Anterior Eye, vol. 36, No. 5, Elsevier Ltd., Oct. 2013, pp. 226-231.
Final Office Action for U.S. Appl. No. 12/015,600 dated Apr. 29, 2014, 9 pages.
Advisory Action and Applicant-Initiated Interview Summary for U.S. Appl. No. 13/183,901 dated Apr. 21, 2014, 5 pages.
Second Office Action for Chinese patent application 201210077192.7 dated May 5, 2014, 3 pages.
Final Office Action for U.S. Appl. No. 11/434,033 dated Jun. 2, 2014, 11 pages.
Non-final Office Action for U.S. Appl. No. 11/931,398 dated Jun. 3, 2014, 8 pages.
Non-final Office Action for U.S. Appl. No. 11/928,681 dated Jun. 4, 2014, 7 pages.
Non-final Office Action for U.S. Appl. No. 11/931,914 dated Jun. 10, 2014, 15 pages.
First Office Action for Chinese patent application 201310017764.7 dated Mar. 31, 2014, 20 pages.
First Office Action for Chinese patent application 201310017761.3 dated May 6, 2014, 12 pages.

(56) References Cited

OTHER PUBLICATIONS

Second Office Action for Chinese patent application 201210077169.8 dated May 20, 2014, 3 pages (no translation).
Notice of Allowance for U.S. Appl. No. 11/434,033 dated Aug. 8, 2014, 8 pages.
Final Office Action for U.S. Appl. No. 12/015,593 dated Jul. 7, 2014, 19 pages.
Advisory Action for U.S. Appl. No. 12/015,600 dated Jul. 16, 2014, 3 pages.
Examination Report for European Patent Application No. 07716441.6 dated May 19, 2014, 4 pages.
Notice of Allowance for U.S. Appl. No. 11/928,681, dated Sep. 22, 2014, 9 pages.
Advisory Action for U.S. Appl. No. 12/015,593, dated Oct. 16, 2014, 3 pages.
Lin, Hui et al., "Dry eye disease: A review of diagnostic approaches and treatments," Saudi Journal of Ophthalmology, vol. 28, Issue 3, Jul.-Sep. 2014, Saudi Ophthalmological Society, pp. 173-181.
Ozer, P.A. et al., "Eyelid nodule in a child: a chalazion or idiopathic facial aseptic granuloma?" Eye, vol. 28, No. 9, Sep. 2014, The Royal College of Ophthalmologists, pp. 1146-1147.
Non-Final Office Action for U.S. Appl. No. 12/015,600 dated Oct. 31, 2014, 9 pages.
Bron, Anthony J. et al., "Rethinking Dry Eye Disease: A Perspective on Clinical Implications," The Ocular Surface, vol. 12, No. 2S, Apr. 2014, Elsevier Inc., 31 pages.
Foulks, Gary N., "The Correlation Between the Tear Film Lipid Layer and Dry Eye Disease," Survey of Ophthalmology, vol. 52, Issue 4, Jul.-Aug. 2007, Elsevier Inc., pp. 369-374.
Second Office Action for Chinese Patent Application No. 201310017764.7, dated Nov. 15, 2014, 12 pages.
Second Office Action for Chinese Patent Application No. 201210127347.3, dated Nov. 2, 2014, 7 pages.
Zhang, J. et al., "A Meibomian Gland Massage Mechanism for Upper and Lower Eyelids Based on Anti-phase Rolling and Enveloping Movement," Chinese Journal of Medical Instrumentation, vol. 38, No. 4, Jul. 2014, pp. 255-258, 273.
Notice of Allowance for U.S. Appl. No. 11/931,398, dated Jan. 16, 2015, 8 pages.
Non-Final Office Action for U.S. Appl. No. 13/183,901, dated Feb. 12, 2015, 9 pages.
Baumann, A. et al., "Meibomian gland dysfunction: A comparative study of modern treatments," French Journal of Ophthalmology, vol. 37, No. 4, Apr. 2014, Elsevier Masson SAS, pp. 303-312.
Non-Final Office Action for U.S. Appl. No. 11/931,914, dated Jun. 8, 2015, 25 pages.
Non-Final Office Action for U.S. Appl. No. 12/015,593, dated Jun. 4, 2015, 20 pages.
Third Office Action for Chinese Patent Application No. 201210127347.3, dated Jun. 26, 2015, 7 pages.
Examination Report for European Patent Application No. 06801969.4, dated Jul. 6, 2015, 5 pages.
Notice of Allowance for U.S. Appl. No. 13/183,901, dated Aug. 12, 2015, 11 pages.
Blackie, Caroline A., et al., "Treatment for meibomian gland dysfunction and dry eye symptoms with a single-dose vectored thermal pulsation: a review," Current Opinion in Ophthamology, vol. 26, Issue 4, Jul. 2015, Lippincott Williams & Wilkins, pp. 306-313.
Doan, S., et al., "Evaluation of an eyelid warming device (Blephasteame®) for the management of ocular surface diseases in France: The ESPOIR study," Journal Françcais d'Ophtalmologie, vol. 37, Issue 10, Oct. 1, 2014, Elsevier Masson SAS, pp. 763-772.
Thode, Adam R., et al., "Current and Emerging Therapeutic Strategies for the Treatment of Meibomian Gland Dysfunction (MGD)," Drugs, vol. 75, Issue 11, Jul. 1, 2015, Springer International Publishing, pp. 1177-1185.
Vora, Gargi K., et al., "Intense pulsed light therapy for the treatment of evaporative dry eye disease," Current Opinion in Ophthalmology, vol. 26, Issue 4, Jul. 2015, Wolters Kluwer Health, Inc., pp. 314-318.
Advisory Action for U.S. Appl. No. 12/015,600 dated Nov. 3, 2015, 3 pages.
Examination Report for European Patent Application No. 08727830.5 dated Oct. 5, 2015, 5 pages.
Author Unknown, "appendages of the eye," The Free Dictionary by Farlex, Medical Dictionary, retrieved on Feb. 8, 2016, medical-dictionary.thefreedictionary.com/appendages+of+the+eye, Farlex and Partners, 1 page.
Author Unknown, "Medical Definition of ORBIT," Merriam-Webster Dictionary, retrieved Feb. 8, 2016, www.merriam-webster.com/medical/orbit, Merriam-Webster, Incorporated, 2 pages.
Goslin, Krysta, et al., "Evaluation of a Single Thermal Pulsation Treatment for Dry Eye and Meibomian Gland Dysfunction and Likelihood of Positive SJO Test," Investigative Ophthalmology & Visual Science, vol. 56, Jun. 2015, The Association for Research in Vision and Ophthalmology, 2 pages (Meeting Abstract).
Hynes, Michael, et al., "Design of a subtarsal ultrasonic transducer for mild hyperthermia of meibomian glands treating Dry Eye Disease," Investigative Ophthalmology & Visual Science, vol. 56, Jun. 2015, The Association for Research in Vision and Ophthalmology, 3 pages (Meeting Abstract).
Nakayama, Naohiko, et al., "Analysis of Meibum Before and After Intraductal Meibomian Gland Probing in Eyes with Obstructive Meibomian Gland Dysfunction," Cornea, vol. 34, Issue 10, Oct. 2015, Wolters Kluwer Health, Inc., pp. 1206-1208.
Nakayama, Naohiko, et al., "Analysis of Meibum Before and Following Intraductal Meibomian Gland Probing for Eyes with Obstructive Meibomian Gland Dysfunction," Investigative Ophthalmology & Visual Science, vol. 56, Jun. 2015, The Association for Research in Vision and Ophthalmology, 2 pages (Meeting Abstract).
Ngo, William, et al., "Effect of Lid Debridement-Scaling on Dry Eye Signs and Symptoms in Sjogren's Syndrome," Investigative Ophthalmology & Visual Science, vol. 56, Jun. 2015, The Association for Research in Vision and Ophthalmology, 2 pages (Meeting Abstract).
Tanabe, Hirotaka, et al., "Effect of Eye Shampoo for Obstructive Meibomian Gland Disease," Investigative Ophthalmology & Visual Science, vol. 56, Jun. 2015, The Association for Research in Vision and Ophthalmology, 2 pages (Meeting Abstract).
Vegunta, Srav, et al., "Tear osmolarity measurements in ocular graft-versus-host disease patients undergoing intense pulsed light (IPL) and meibomian gland expression (MGX)," Investigative Ophthalmology & Visual Science, vol. 56, Jun. 2015, The Association for Research in Vision and Ophthalmology, 2 pages (Meeting Abstract).
Non-Final Office Action for U.S. Appl. No. 14/510,843, dated Feb. 4, 2016, 10 pages.
Final Office Action for U.S. Appl. No. 12/015,593, dated Feb. 16, 2016, 22 pages.
Notice of Allowance for U.S. Appl. No. 12/015,600, dated Jan. 20, 2016, 7 pages.
Non-Final Office Action for U.S. Appl. No. 13/590,828, dated Feb. 26, 2016, 11 pages.
Fourth Office Action for Chinese Patent Application No. 201210127347.3, dated Feb. 29, 2016, 9 pages.
Decision of Rejection for Japanese Patent Application No. 2013-226709, dated Feb. 2, 2016, 8 pages.
Author Unknown, "Simple Definition of AROUND," Merriam-Webster's Learner's Dictionary, accessed Aug. 15, 2016, www.merriam-webster.com/dictionary/around, 1 page.
Author Unknown, Definition of "Orbit," Miller-Keane Encyclopedia and Dictionary of Medicine, Nursing, and Allied Health, Seventh Edition, 2003, Saunders, medical-dictionary.thefreedictionary.com/orbit, accessed Sep. 29, 2016, 1 page.
Author Unknown, "Medical Definition of PERIORBITAL," Merriam-Webster: Medical Dictionary, accessed Aug. 15, 2016, www.merriam-webster.com/medical/periorbital, 1 page.

(56) References Cited

OTHER PUBLICATIONS

Di Pascuale, Mario A., et al, "Lipid tear deficiency in persistent dry eye after laser in situ keratomileusis and treatment results of new eye-warming device," Journal of Cataract & Refractive Surgery, vol. 31, Issue 9, Sep. 2005, Elsevier, pp. 1741-1749.

Hynes, Michael, B., et al., "Design of a Subtarsal Ultrasonic Transducer for Mild Hyperthermia Treatment of Dry Eye Disease," Ultrasound in Medicine & Biology, vol. 42, Issue 1, Jan. 2016, Elsevier Inc., pp. 232-242.

Matsumoto, Yukihiro, et al., "Efficacy of a New Warm Moist Air Device on Tear Functions of Patients With Simple Meibomian Gland Dysfunction," Cornea, vol. 25, Issue 6, Jul. 2006, Lippincott Williams & Wilkins, pp. 544-650.

Non-Final Office Action for U.S. Appl. No. 11/541,308, dated Sep. 29, 2016, 26 pages.

Non-Final Office Action for U.S. Appl. No. 14/618,392, dated Sep. 30, 2016, 11 pages.

Final Office Action for U.S. Appl. No. 14/510,843, dated Aug. 25, 2016, 13 pages.

Final Office Action for U.S. Appl. No. 13/590,828, dated Sep. 9, 2016, 12 pages.

Extended European Search Report for European Patent Application No. 16170742.7, dated Sep. 8, 2016, 8 pages.

Dudee, Jitander S., "Affidavit," mailed Aug. 26, 2016, 2 pages.

U.S. Appl. No. 09/178,772, filed Oct. 26, 1998, not published.

Author Unknown, "arGentis Licenses Third Treatment for Dry Eye Syndrome", Business Wire, May 12, 2008, accessed Jun. 4, 2008, 2 pages.

Author Unknown, "New Over-the-Counter Dry Eye Drop Now Available to Help Estimated 40 Percent of Americans Who Suffer from Occasional or Chronic Dry Eye", Business Wire News Release, Mar. 31, 2008, accessed Jun. 5, 2008, 4 pages.

Author Unknown, "The Honan Intraocular Pressure Reducer (Honan's Balloon)," The Lebanon Corporation, Lebanon, Indiana, http://www.honanballoon.com/, accessed on May 29, 2009, 2 pages.

Author Unknown, "Treat high eye pressure—a major risk factor for Glaucoma," Product Information Booklet for Xalatan, Pfizer Inc., Copyright 2003, Jul. 2003, 11 pages.

Author Unknown, "Understanding Glaucoma—What You Can Do to Save Your Sight," Krames Communications, Copyright 1994, San Bruno, California, 16 pages.

Author Unknown, "What is Glaucoma—The Sneak-Thief of Sight," http://www.glaucoma.org.au/whatis.htm, last updated on Feb. 10, 2006, accessed on Feb. 18, 2008, 5 pages.

Author Unknown, "What is PNT," Ophthalmic International, http://www.ophthalmicinternational.com/PNT_ROW_What_is_pnt.html, accessed on Oct. 31, 2006, 2 pages.

Agnifili et al., "In vivo confocal microscopy of meibomian glands in glaucoma," British Journal of Ophthalmology, vol. 97, No. 3, Mar. 2013, pp. 343-349, United Kingdom.

Akyol-Salman, Ilknur et al., "Efficacy of Topical N-Acetylcysteine in the Treatment of Meibomian Gland Dysfunction," Journal of Ocular Pharmacology and Therapeutics, vol. 26, No. 4, Aug. 1, 2010, pp. 329-333.

Author Unknown, "Implantable Glaucoma Devices," American National Standard for Ophthalmics, ANSI Z80. -200X, Draft Copy, Revised Apr. 5, 2007, 45 pages.

Arita, R. et al., "Topical diquafosol for patients with obstructive meibomian gland dysfunction," British Journal of Ophthalmology, vol. 97, No. 6, Jun. 2013, pp. 725-729.

Aronowicz, JD et al. "Short Term Oral Minocycline Treatment of Meibomianitis," British Journal of Ophthalmology, vol. 90, No. 7, Jul. 2006, 6 pages.

Author Unknown, Definition of Platform, Merriam-Webster Dictionary, accessed Dec. 10, 2012, 3 pages, http://www.merriam-webster.com/dictionary/platform.

Author Unknown, Definition of On, Merriam-Webster Dictionary, accessed Dec. 14, 2012, 5 pages, http://www.merriam-webster.com/dictionary/on.

Author Unknown, Definition of Platform, Macmillan Dictionary, accessed Dec. 10, 2012, 2 pages, http://www.macmillandictionary.com/dictionary/british/platform.

Author Unknown, "New Breakthrough Treatment for Evaporative Dry Eye Disease Introduced by Dry Eye Specialist, Mark R. Mandel, M.D.," PR Newswire, Dec. 11, 2012, 2 pages.

Bell, Jerald A. et al., "Glaucoma, Primary Open Angle," Excerpt, Aug. 16, 2005, 16 pages.

Blackie, Caroline A. et al., "Inner Eyelid Surface Temperature as a Function of Warm Compress Methodology," Optometry and Vision Science, vol. 85, No. 8, Aug. 2008, pp. 675-683.

Blackie, Caroline A. et al., "Nonobvious Obstructive Meibomian Gland Dysfunction" Cornea, vol. 29, No. 12, Dec. 2010, pp. 1333-1345.

Blackie, Caroline A. et al., "Recovery Time of an Optimally Secreting Meibomian Gland," Cornea, vol. 28, No. 3, Apr. 2009, pp. 293-297.

Booth et al., "TIGR and Stretch in the Trabecular Meshwork," Investigative Ophthalmology and Visual Science, vol. 40, 1999, pp. 1888-1889.

Butovich, Igor et al., "Meibomian Lipid Glands and the Impact of Temperature," Investigative Opthalmology & Visual Science, vol. 51, No. 11, Nov. 2010, pp. 5508-5518.

Cuevas, M. et al., "Correlations Among Symptoms, Signs, and Clinical Tests in Evaporative-Type Dry Eye Disease Caused by Meibomian Gland Dysfunction (MGD)," Current Eye Research, vol. 37, No. 10, Oct. 2012, pp. 855-863.

Dausch, Eva et al., "Dry Eye Syndrome in Women's Health and Gynecology: Etiology, Pathogenesis and Current Therapeutic Strategies," Geburtshilfe und Frauenheilkunde, vol. 70, No. 9, Jan. 1, 2010, pp. 707-711. (Abstract Only).

Donnenfeld, Eric et al., "Topical Ophthalmic Cyclosporine: Pharmacology and Clinical Uses," Survey of Ophthalmology, vol. 54, No. 3, May/Jun. 2009, pp. 321-338.

Finis, D. et al., "Meibom-Drusen-Dysfunktion," Klinische Monatsblatter fur Augenheilkunde, vol. 229, No. 5, Mar. 2012, pp. 506-513 (Abstract translated only).

Foulks, Gary N. et al., "Topical Azithromycin Therapy for Meibomian Gland Dysfunction: Clinical Response and Lipid Alterations," Cornea, vol. 29, No. 7, Jul. 2010, pp. 781-788.

Foulks, Gary N., "Meibomian Gland Dysfunction: The Past, Present, and Future," Eye and Contact Lens, vol. 36, No. 5, Sep. 2010, pp. 249-253.

Foulks, G. et al., Comparative Effectiveness of Azithromycin and Doxycycline in Therapy of Meibomian Gland Dysfunction, ARVO Annual Meeting, May 2011, pp. 3816 (Abstract only).

Friedland, B., et al., "A novel thermodynamic treatment for meibomian gland dysfunction," Current Eye Research, vol. 36, No. 2, Feb. 2011, pp. 79-87.

Gayer, S. et al., "Ocular Decompression Devices: Liquid Mercury Balloon vs. the Tungsten Powder Balloon," American Journal of Ophthalmology, 2006, vol. 142, No. 3, pp. 500-501.

Geerling, G., et al., "The international workshop on meibomian gland dysfunction: report of the subcommittee on management and treatment of meibomian gland dysfunction," Mar. 2011, pp. 2050-2064, Investigative Ophthalmology & Visual Science, vol. 52, No. 4.

Goto, E., et al. "Treatment of Non-Inflamed Obstructive Meibomian Gland Dysfunction by an Infrared Warm Compression Device," Br. J. Ophthalmology, vol. 86, pp. 1403-1407, Dec. 2002.

Goto, Eiki, et al., "Tear Evaporation Dynamics in Normal Subjects and Subjects with Obstructive Meibomian Gland Dysfunction," Investigative Ophthalmology & Visual Science, vol. 44, No. 2, pp. 533-539, Feb. 2003.

Greiner, J., "A Single LipiFlow R Thermal Pulsation System Treatment Improves Meibomian Gland Function and Reduces Dry Eye Symptoms for 9 months," Current Eye Research, vol. 37 No. 4, Apr. 2012, pp. 272-278.

Greiner, J., "Long-term 12-month improvement in meibomian gland function and reduced dry eye symptoms with a single thermal pulsation treatment," Clinical and Experimental Ophthalmology, vol. 41, No. 6, Aug. 2013, pp. 524-530.

(56) References Cited

OTHER PUBLICATIONS

Gupta, S. et al. "Docetaxel-Induced Meibomian Duct Inflammation and Blockage Leading to Chalazion Formation," Prostate Cancer Prostatic Diseases, vol. 10, No. 4, 2007.
Khandelwal, et al., "Androgen regulation of gene expression in human meibomian gland and conjunctival epithelial cells," Molecular Vision, vol. 18, Apr. 27, 2012, pp. 1055-1067.
Knop, E. et al., "Meibomian Glands: Part III—Dysfunction—Argument for a Discrete Disease Entity and as an Important Cause of Dry Eye," Ophthalmologe, vol. 106, No. 11, Nov. 2009, pp. 966-979. (Abstract Only).
Knop, E. et al., "Meibomian Glands: Part IV—Functional Interactions in the Pathogenesis of Meibomian Gland Dysfunction (MGD)," Ophthalmologe, vol. 106, No. 11, Nov. 2009, pp. 980-987. (Abstract Only).
Kokke, K.H. et al., "Oral Omega-6 Essential Fatty Acid Treatment in Contact Lens Associated Dry Eye," Contact Lens and Anterior Eye, vol. 31, No. 3, 2008, pp. 141-146.
Korb, Donald et al., "The Effect of Two Novel Lubricant Eye Drops on Tear Film Lipid Layer Thickness in Subjects with Dry Eye Symptoms," Optom. Vis. Sci., vol. 82, No. 7, 2005, pp. 594-601.
Korb, Donald R. et al., "Increase in Tear Film Lipid Layer Thickness Following Treatment of Meibomian Gland Dysfunction", Lacrimal Gland, Tear Film & Dry Eye Syndromes, Plenum Press, 1994, pp. 293-298.
Korb, Donald R. et al., "Lid Wiper Epitheliopathy and Dry Eye Symptoms," Eye & Contact Lens, vol. 31, No. 1, 2005, pp. 2-8.
Korb, Donald R. et al., "Restoration of Meibomian Gland Functionality with Novel Thermodynamic Treatment Device—A Case Report," Cornea, vol. 29, No. 8, Aug. 2010, pp. 930-933.
Korb, Donald R. et al., "Tear Film Lipid Layer Thickness as a Function of Blinking," Cornea, vol. 13, No. 4, 1994, pp. 354-359.
Korb, Donald R. et al., Slide entitled "Inner Eyelid Surface Temperature as a Function of Warm Compress Methodology," from presentation entitled "The Greatest Anterior Segment Disease and Contact Lens Complications Course," AOA Meeting, Seattle, Washington, Jun. 27, 2008, 2 pages.
Korb, Donald R., O.D., et al., "Meibomian Gland Dysfunction and Contact Lens Intolerance," Journal of the American Optometric Association, vol. 51, No. 3, Mar. 1980, pp. 243-251.
Korb, Donald R., Slide entitled "Inner Eyelid Surface Temperature as a Function of Warm Compress Methodology," from presentation entitled "The Tear Film and Dry Eye States A Fertile Research Area," University of California at Berkeley, School of Optometry, Apr. 11, 2008, 2 pages.
Korb, et al., "Forceful Meibomian Gland Expression with a Standardized Force of 8 PSI in Patients with Obstructive Meibomian Gland Dysfunction," ARVO Annual Meeting, Poster Session, Program No. 3819, Poster Board No. D952, May 3, 2011, 2 pages (Abstract Only).
Korb, et al., "Prevalence of lid wiper epitheliopathy in subjects with dry eye signs and symptoms," Cornea, vol. 29, No. 4, Apr. 2012, pp. 377-383.
Korb, et al., "Restoration of meibomian gland function post Lipiflow treatment," ARVO Annual Meeting, May 2011, pp. 3818 (Abstract only).
Kuscu, Naci Kemal, et al., "Tear Function Changes of Postmenopausal Women in Response to Hormone Replacement Therapy," Maturitas, vol. 44, pp. 63-68, 2003.
Lane, S. et al., "A New System, the LipiFlow, for the Treatment of Meibomian Gland Dysfunction," Cornea, vol. 31, No. 4, Apr. 2012, pp. 396-404.
Lemp, Michael A. et al., "Blepharitis in the United States 2009: A Survey-Based Perspective on Prevalence and Treatment." Ocul. Surf, vol. 7, No. 2 Suppl, Apr. 2009, pp. S1-S14.
Lemp, Michael A., et al., "The Therapeutic Role of Lipids-Managing Ocular Surface Disease," Supplement to Refractive Eyecare of Ophthalmologists, vol. 9, No. 6, Jun. 2005.

Li, Li-Hu et al., "Analysis of the efficacy in the treatment of meibomian gland dysfunction," International Eye Science, vol. 13, No. 7, Jul. 2013, pp. 1495-1497.
Maskin, S. et al., "Intraductal Meibomian Gland Probing with Adjunctive Intraductal Microtube Steriod Injection (MGPs) for Meibomian Gland Dysfuction," ARVO Annual Meeting, May 2011, pp. 3817 (Abstract only).
Maskin, Steven L., "Intraductal Meibomian Gland Probing Relieves Symptoms of Obstructive Meibomian Gland Dysfunction," Corena, vol. 29, No. 10, Oct. 2010, pp. 1145-1152.
McCann, L. et al., "Effect of First Line Management Therapies on Dry Eye Disease," ARVO Annual Meeting, May 2011, pp. 3829 (Abstract only).
Matsumoto, Yukihiro et al., "The Evaluation of the Treatment Response in Obstructive Meibomian Gland Disease by In Vivo Laser Confocal Microscopy," Graefes Arch Clin Exp Ophthalmol, vol. 247, No. 6, Jun. 2009, pp. 821-829.
Miller, David, "Pressure of the Lid on the Eye," Arch Ophthalmology, vol. 78, 1967, pp. 238-330.
Mitra, M. et al., "Tear Film Lipid Layer Thickness and Ocular Comfort after Meibomian Therapy via Latent Heat with a Novel Device in Normal Subjects," Eye, pp. 1-4, 2004.
Mori, Asako, et al., "Disposable Eyelid-Warming Device for the Treatment of Meibomian Gland Dysfunction", Japan Journal of Ophthalmology, vol. 47, pp. 578-586, 2003.
Author Unknown, "NEI/FDA CDER Glaucoma Clinical Drug Trial Design and Endpoints Symposium," Agenda, Mar. 13-14, 2008, Bethesda, Maryland, 3 pages.
Olson, Mary Catherine, B.A., et al., "Increase in Tear Film Lipid Layer Thickness Following Treatment with Warm Compresses in Patients with Meibomian Gland Dysfunction," Eye & Contact Lens, vol. 29, No. 2, pp. 96-99, 2003.
Paugh, J.R. et al., "Meibomian Therapy in Problematic Contact Lens Wear," Entrez PubMed, Optom Vis Sci, vol. 68, No. 11, Nov. 1990, pp. 803-806 (abstract only).
Paugh, Jerry R. et al., "Precorneal Residence Time of Artificial Tears Measured in Dry Eye Subjects," Optometry and Vision Science, vol. 85, No. 8, Aug. 2008, pp. 725-731.
Pucker, A. et al., "Analysis of Meibum and Tear Lipids," The Ocular Surface, vol. 10, No. 4, Oct. 2012, pp. 230-250.
Romero, Juan M., et al., "Conservative Treatment of Meibomian Gland Dysfunction," Contact Lens Association of Ophthalmology, Eye & Contact Lens, vol. 30, pp. 14-19, 2004.
Shiozawa, K. et al., "Correlation of the presence of meibomian gland dysfunction with the incidence of superficial punctate keratopathy after penetrating keratoplasty," Nihon Ganka Gakkai Zasshi, vol. 107, No. 2, Feb. 2003, pp. 84-87.
Sullivan, Benjamin D., et al., "Impact of Antiandrogen Treatment on the Fatty Acid Profile of Neutral Lipids in Human Meibomian Gland Secretions," Journal of Clinical Endocrinogy & Metabolism, Vo. 85, No. 12, pp. 4866-4873, 2000.
Sullivan, David et al., "Do Sex Steroids Exert Sex-Specific and/or Opposite Effects on Gene Expression in Lacrimal and Meibomian Glands?" Molecular Vision, vol. 15, No. 166, Aug. 10, 2009, pp. 1553-1572.
Suzuki, Tomo et al., "Estrogen and Progesterone Control of Gene Expression in the Mouse Meibomian Gland," Invest. Ophthalmol. Vis. Sci., vol. 49, No. 5, Apr. 2008, pp. 1797-1818.
Suzuki, Tomo, "Meibomitis-Related Keratoconjunctivitis: Implications and Clinical Significance of Meibomian Gland Inflammation," Cornea, vol. 31, Supplemental Issue, Nov. 2012, pp. S41-S44.
Taban et al., "The Importance of Lowering Intraocular Pressure," Medscape Ophthalmology, Feb. 20, 2008, Medscape, 6 pages.
Tan, J. et al., "The Effect of Non-Surgical Intraocular Pressure Reduction on the Optic Nerve Head," IOVS, vol. 41, No. 4, Mar. 15, 2000, 1522-B897, 1 page.
Tang, Qin et al., "Clinical analysis of meibomian gland dysfunction in elderly patients," International Eye Science, vol. 13, No. 7, Jul. 2013, pp. 1419-1423.
Tobler, David et al., "Nanotech Silver Fights Microbes in Medical Devices," Medical Device & Diagnostic Industry, May 1, 2005, 6 pages.

(56) References Cited

OTHER PUBLICATIONS

Toyos, Rolando, "Intense Pulsed Light for Dry Eye Syndrome," Cataract & Refractive Surgery Today, Apr. 2009, pp. 1-3.
Wolff et al., "Eugene Wolff's Anatomy of the Eye and Orbit," Excerpt, Capman and Hall Medical, 1997, p. 170.
Unknown, "TearScience Launches Breakthrough Technology in Canada to Address the Root Cause of Evaporative Dry Eye," Business Wire, Jun. 9, 2011, http://www.businesswire.com/news/home/20110609005860/en/TearScience-Launches-Breakthrough-Technology-Canada-Address-Root, 2 pages.
Vasta, Stephanie, "Aggressive Treatments Developed for Meibomian Gland Dysfunction," Primary Care Optometry News, Nov. 1, 2009, 3 pages.
Wang, Y. et al., "Baseline Profiles of Ocular Surface and Tear Dynamics After Allogeneic Hematopoietic Stem Cell Transplantation in Patients With or Without Chronic GVHD-Related Dry Eye," Bone Marrow Transplantation, vol. 45, No. 6, Jun. 2010, pp. 1077-1083.
Wells, Anthony P. et al., "Corneal Hysteresis but Not Corneal Thickness Correlates with Optic Nerve Surface Compliance in Glaucoma Patients," Investigative Ophthalmology and Visual Science, vol. 49, 2008, pp. 3262-3268 (abstract only).
Willis, et al., Meibomian gland function, lid wiper epitheliopathy, and dry eye symptoms, ARVO Annual Meeting, May 2011, pp. 3740 (Abstact only).
Zhang et al., "Efficacy of physical therapy meibomian gland dysfunction," International Eye Science, International Journal of Ophthalmology, vol. 13, No. 6, Jun. 2013, pp. 1267-1268.
Cunniffe, M. Geraldine et al., "Topical antiglaucoma treatment with prostaglandin analogues may precipitate meibomian gland disease," Ophthalmic Plastic and Reconstructive Surgery, Sep.-Oct. 2011, p. 128-129, vol. 27, No. 9, Lippincott Williams and Wilkins, Philadelphia, PA.
Holifield, Karintha and Lazzaro, Douglas R., "Case report: Spontaneous stenotrophomonas maltophilia keratitis in a diabetic patient," Eye and Contact Lens, Sep. 2011, pp. 326-327, vol. 37, No. 5, Philadelphia PA.
Korb, Donald R. and Blackie, Caroline A., "Meibomian gland therapeutic expression: Quantifying the applied pressure and the limitation of resulting pain," Eye and Contact Lens, Sep. 2011, pp. 298-301, vol. 37, No. 5, Philadelphia, PA.
Korb, D. et al., "Meibomian gland therapeutic expression: quantifying the applied pressure and the limitation of resulting pain," Eye Contact Lens, vol. 37 No. 5, Sep. 2011, pp. 298-301.
Akyol-Salman, I. et al., "Comparison of the efficacy of topical N-acetyl-cysteine and a topical steroid-antibiotic combination therapy in the treatment of meibomian gland dysfunction," Journal of Ocular Pharmacology and Therapeutic, vol. 28, No. 1, Feb. 2, 2012, pp. 49-52.
Author Unknown, "TearScience's LipiFlow Multi-center Clinical Study Shows Improved Meibomian Gland Secretions and Dry Eye Symptoms," Business Wire, Mar. 5, 2012, 2 pages.
Asbell, P. et al. "The international workshop on meibomian gland dysfunction: report of the clinical trials subcommittee," Investigative Ophthalmology and Visual Science, Mar. 2011, pp. 2065-2085.
Foulks et al., "Improving awareness, identification, and management of meibomian gland dysfunction," Ophthalmology, vol. 119, No. 10 Sup., Oct. 2012, 12 pages.
Arita, F. et al., "Comparison of the long-term effects of various topical antiglaucoma medications on meibomian glands," Cornea, vol. 31, No. 11, Nov. 2012, pp. 1229-1234.
Advisory Action for U.S. Appl. No. 13/590,828, dated Jan. 27, 2017, 3 pages.
Notice of Allowance for U.S. Appl. No. 13/590,828, dated Mar. 8, 2017, 9 pages.
First Examination Report for Indian Patent Application No. 1318/MUMNP/2009, dated Mar. 14, 2017, 20 pages.
Non-Final Office Action for U.S. Appl. No. 11/541,308, dated Apr. 27, 2017, 21 pages.
Author Unknown, "IFU Manual for PNT Model 1000," Revision H, Ophthalmic International, Fountain Hills, Arizona, Feb. 11, 2009, 24 pages.
Author Unknown, "Home," http://www.heatedeyepad.com/home.html, accessed Dec. 16, 2016, Digital Heat, 2 pages.
Author Unknown, "Introducing: Thermofoil Heaters," Minco Bulletin HS-202, 2002, 9 pages.
Author Unknown, "Product," http://www.heatedeyepad.com/product.html, accessed Dec. 16, 2016, Digital Heat, 2 pages.
Aragona, P., et al., "Towards a dynamic customised therapy for ocular surface dysfunctions," British Journal of Ophthalmology, vol. 97, No. 8, Aug. 13, 2013, pp. 955-960.
Mori, A., et al., "Efficacy of the Treatment by the Disposable Eyelid Warming Instrument for Meibomian Gland Dysfunction," Poster Presentation, Hall A, The Association for Research and Vision in Ophthalmology Annual Meeting, Fort Lauderdale, Florida, Apr. 30, 2000, 1 page.
Non-Final Office Action for U.S. Appl. No. 14/618,392, dated Jun. 28, 2017, 23 pages.
Non-Final Office Action for U.S. Appl. No. 14/746,328, dated May 31, 2017, 11 pages.
Final Office Action for U.S. Appl. No. 12/015,600 dated May 21, 2015, 12 pages.
Notice of Rejection for Japanese Patent Application No. 2013-226709, dated Mar. 24, 2015, 10 pages.
Final Office Action for U.S. Appl. No. 11/541,308, dated Oct. 25, 2017, 25 pages.
Final Office Action for U.S. Appl. No. 14/746,328, dated Nov. 16, 2017, 12 pages.
Second Examination Report for Indian Patent Application No. 1318/MUMNP/20097 dated Nov. 18, 2017, 2 pages.

\* cited by examiner

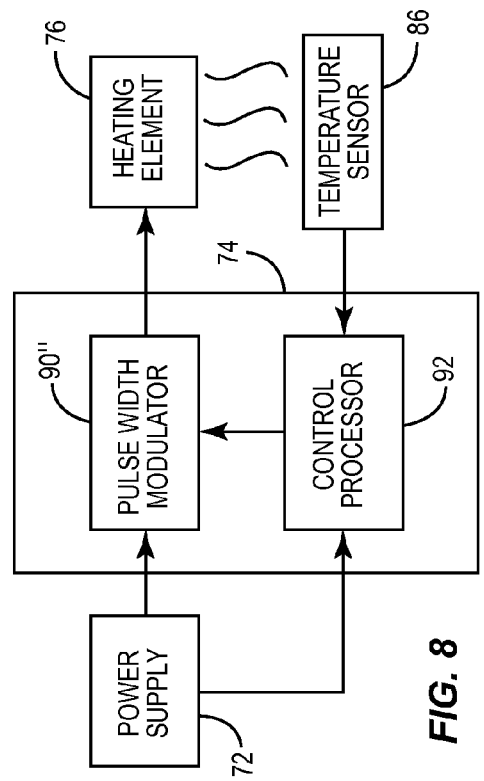
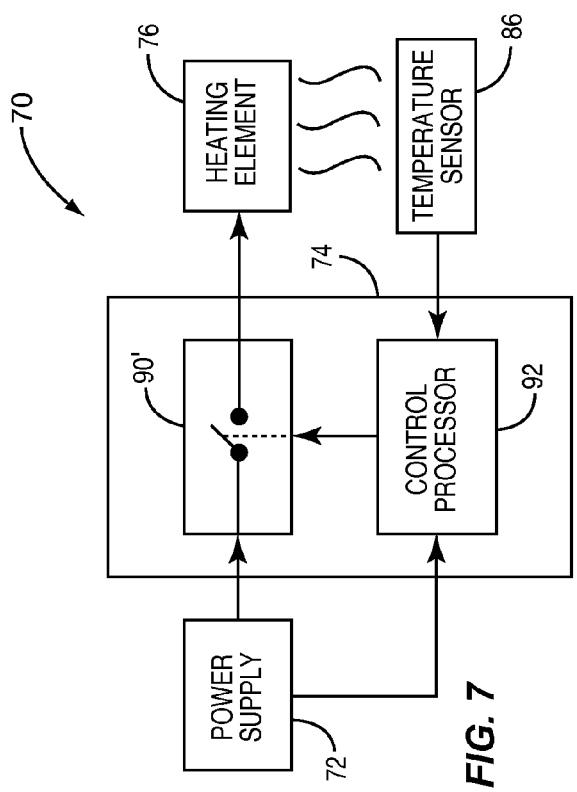
*FIG. 8*
*FIG. 7*

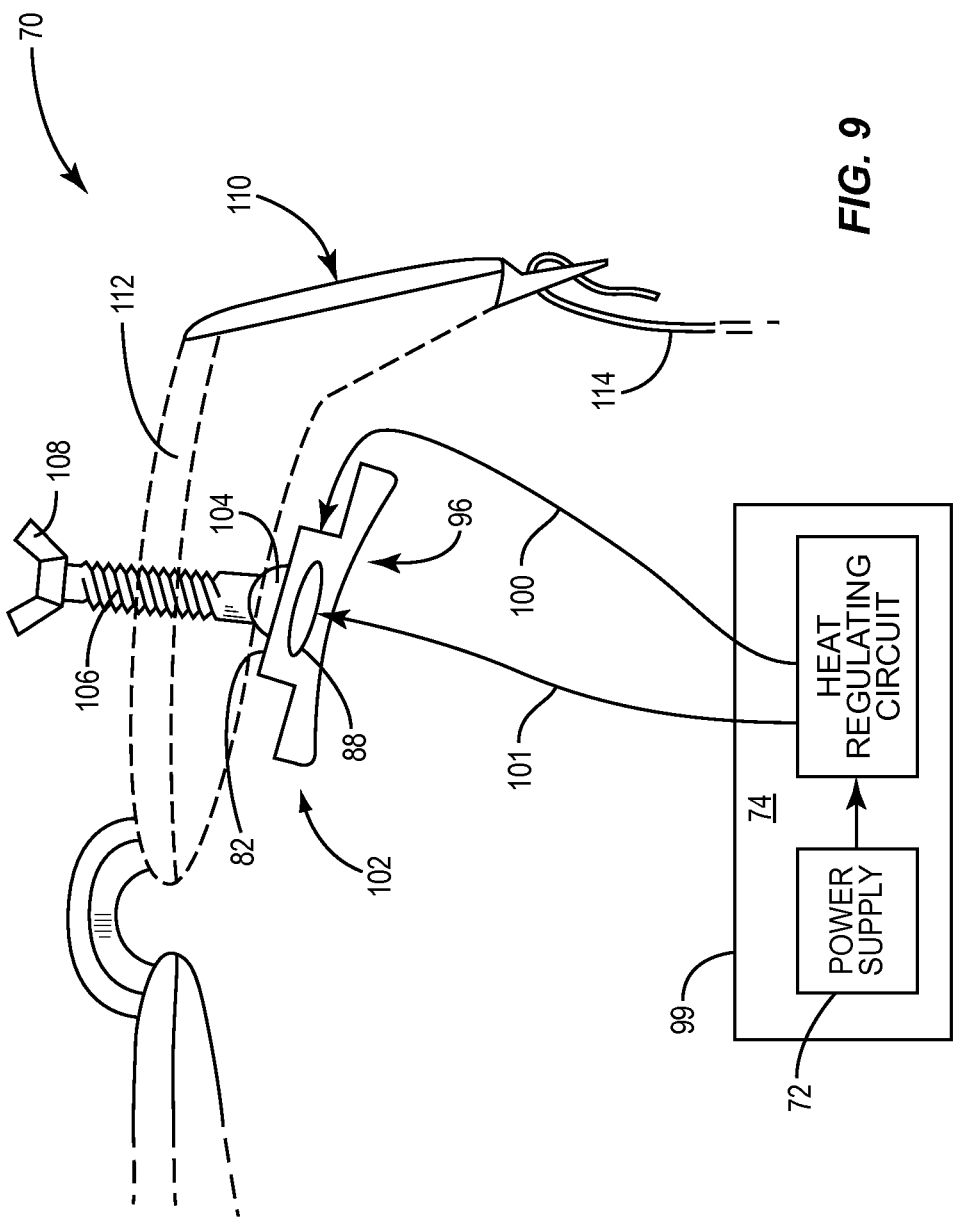

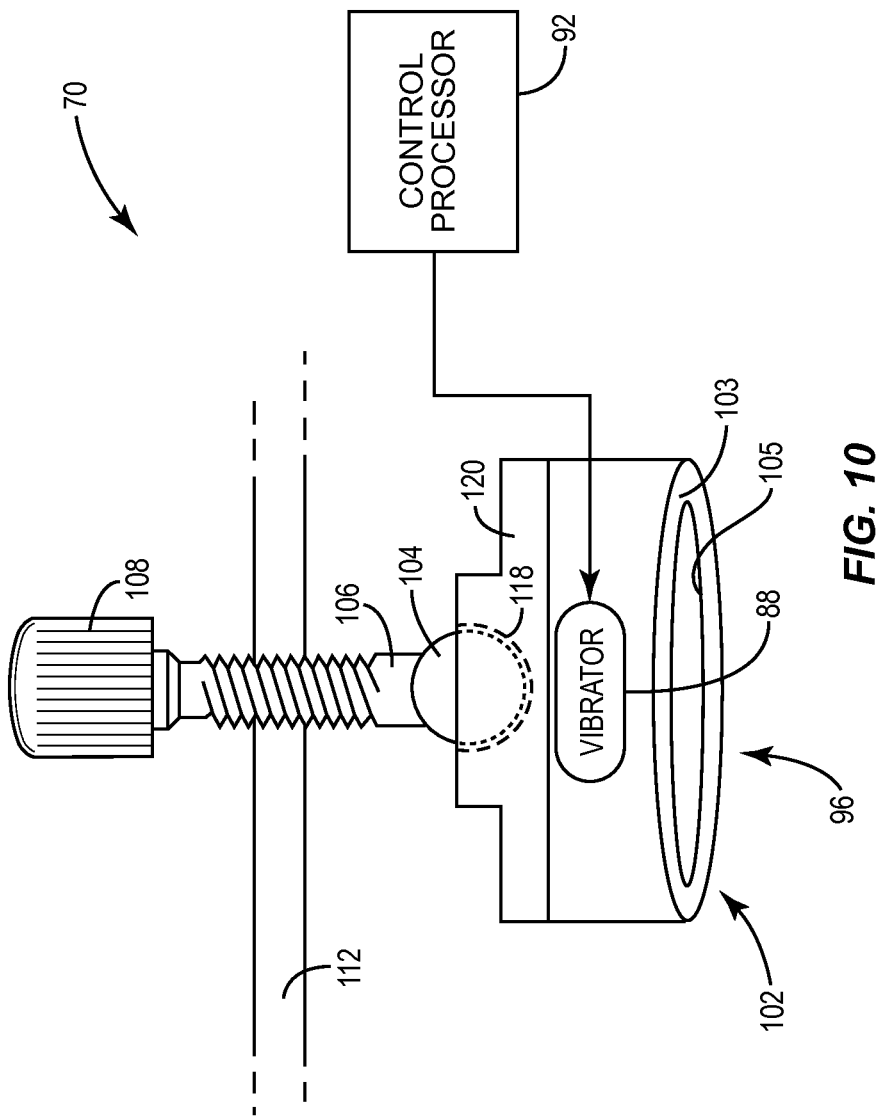

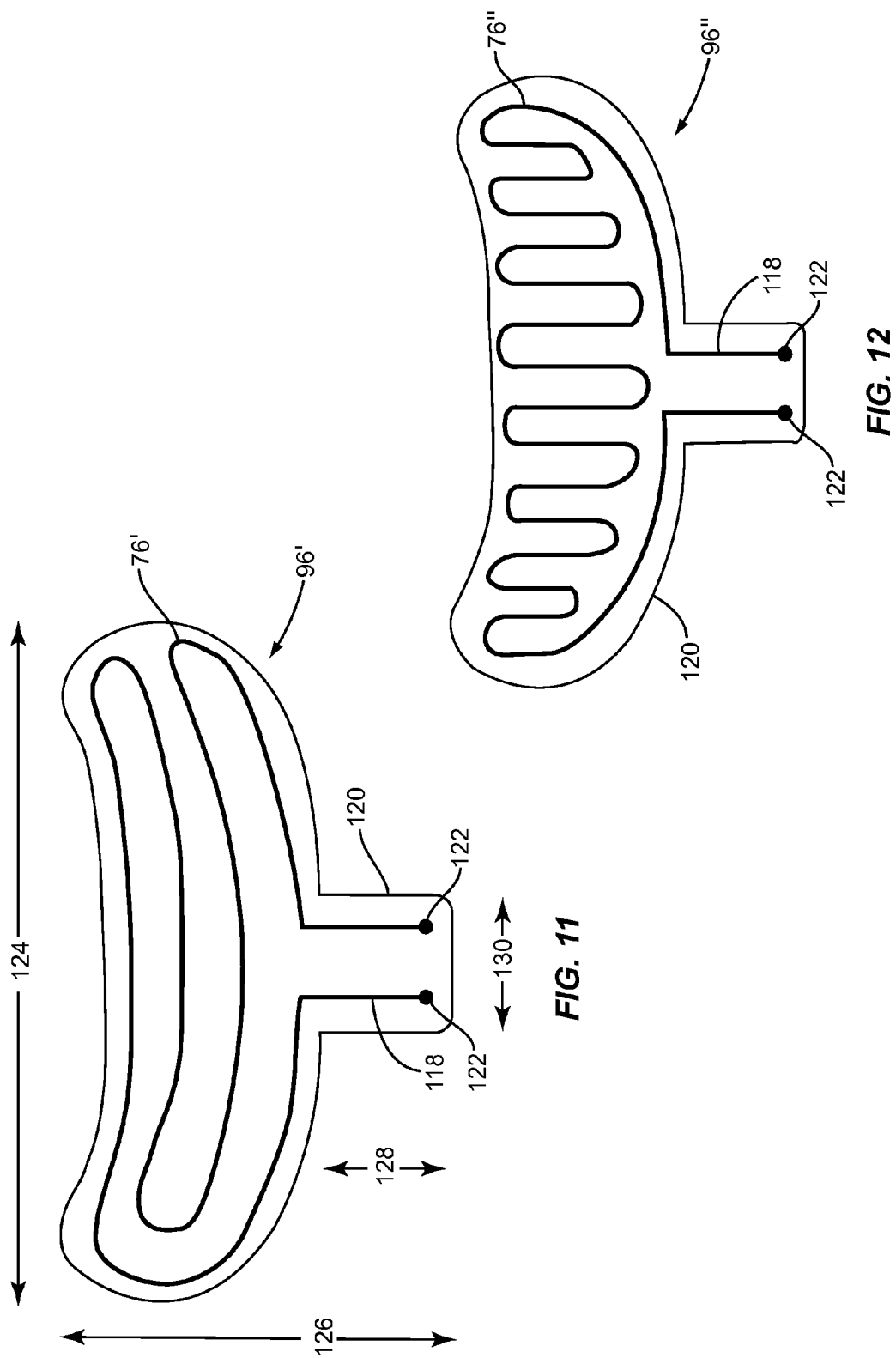

METHODS, APPARATUSES, AND SYSTEMS FOR REDUCING INTRAOCULAR PRESSURE AS A MEANS OF PREVENTING OR TREATING OPEN-ANGLE GLAUCOMA

RELATED APPLICATIONS

The present application is a divisional application of, and claims priority to, U.S. patent application Ser. No. 12/246,071, filed on Oct. 6, 2008, published as U.S. Patent Application Publication No. 2009/0043365, and titled METHODS, APPARATUSES, AND SYSTEMS FOR REDUCING INTRAOCULAR PRESSURE AS A MEANS OF PREVENTING OR TREATING OPEN-ANGLE GLAUCOMA, which is incorporated by reference in its entirety, and is a continuation-in-part of U.S. patent application Ser. No. 11/541,291 filed on Sep. 26, 2006, now issued as U.S. Pat. No. 7,981,095, and entitled "METHOD AND APPARATUS FOR TREATING MEIBOMIAN GLAND DYSFUNCTION EMPLOYING FLUID JET," which is a continuation-in-part of U.S. patent application Ser. No. 11/434,033 filed on May 15, 2006, now issued as U.S. Pat. No. 8,915,253, and entitled "METHOD AND APPARATUS FOR TREATING GLAND DYSFUNCTION EMPLOYING HEATED MEDIUM," which claims priority to U.S. Provisional Patent Application No. 60/700,233 filed on Jul. 18, 2005 and entitled "METHOD AND APPARATUS FOR TREATING GLAND DYSFUNCTION," all of which are incorporated herein by reference in their entireties.

U.S. patent application Ser. No. 12/246,071 is also a continuation-in-part of U.S. patent application Ser. No. 11/541,308 filed on Sep. 29, 2006, published as U.S. Patent Application Publication No. 2007/0060988, and entitled "MELTING MEIBOMIAN GLAND OBSTRUCTIONS," which is a continuation-in-part application of U.S. patent application Ser. No. 11/434,054 filed on May 16, 2006, now issued as U.S. Pat. No. 8,083,787, and entitled "METHOD AND APPARATUS FOR TREATING MEIBOMIAN GLAND DYSFUNCTION," which claims priority to U.S. Provisional Patent Application No. 60/700,233 filed on Jul. 18, 2005 and entitled "METHOD AND APPARATUS FOR TREATING GLAND DYSFUNCTION," all of which are incorporated herein by reference in their entireties.

U.S. patent application Ser. No. 12/246,071 is also a continuation-in-part of U.S. patent application Ser. No. 12/015,558 filed on Jan. 17, 2008, now issued as U.S. Pat. No. 7,981,146, and entitled "INNER EYELID TREATMENT FOR TREATING MEIBOMIAN GLAND DYSFUNCTION," which claims priority to U.S. Provisional Patent Application No. 60/880,850 filed on Jan. 17, 2007 and entitled "METHOD AND APPARATUS FOR TREATING MEIBOMIAN GLAND OBSTRUCTIVE DISEASE," all of which are incorporated herein by reference in their entireties.

FIELD OF THE INVENTION

The present invention relates to methods and apparatuses for reducing intraocular pressure (IOP) as a means of preventing or treating open-angle glaucoma. More particularly, the methods and apparatuses sustainably reduce intraocular pressure (IOP), which causes ocular hypertension (OHT) or glaucoma and which is widely believed to be a leading cause of blindness.

BACKGROUND OF THE INVENTION

Glaucoma is the name given to a group of eye diseases in which the optic nerve at the back of the eye is slowly destroyed. In some people, the damage may be caused by poor blood supply to the vital optic nerve fibers, a weakness in the structure of the nerve, or a problem in the health of the nerve fibers themselves. However in most people, this damage is the result of a reduction or blockage of circulation of aqueous or its drainage, known as open-angle glaucoma. As illustrated in FIG. 1, aqueous humor 10 flows through the inside of the eye 12 and nourishes the lens 14, the iris 16, and the inside 18 of the cornea 20. The aqueous humor 10 leaves the cornea 20 and enters into the trabecular meshwork 22, which is the eye's "drain." The trabecular meshwork 22 contains tiny holes or passages 24 that surround the iris 16. Normally, the aqueous 10 flows freely through the trabecular meshwork 22 and into Schlemm's canal 26, where it then enters back into the bloodstream. However in open-angle glaucoma, if the trabecular meshwork 22 becomes clogged, more aqueous humor 10 flows into the eye 12 than can freely drain out. As a result, intraocular pressure (IOP) can rise, causing ocular hypertension (OHT). OHT is an important risk factor for glaucoma, although other risk factors can contribute to glaucoma, including reduced blood flow to the affected area of the optic nerve.

It is important to reduce elevated IOP as quickly as possible after diagnosis to either prevent the onset of glaucoma or if glaucoma has already damaged the optic nerve and caused vision loss, to prevent any further damage and vision loss. The importance of lowering IOP to treat glaucoma is known. (See, Taban et al., The Importance of Lowering Intraocular Pressure, Medscape Ophthalmology, Feb. 20, 2008) Once IOP is lowered, a suitable treatment is selected to keep IOP under control at normal levels. Known treatments include medication, laser treatment, and surgery. Patient factors such as age, general health, and stage of glaucoma, as well as various socioeconomic and technologic factors may lead to different recommendations for different patients. In the case of medication, eyedrops and pills are the most common treatments. Both can be used to decrease the production of aqueous humor in the eye, but side effects can occur, including headaches, eye irritation, and/or blurred or dimmed vision. Further, the effectiveness of medication diminish over time.

Laser treatment known as "trabeculoplasty" is another accepted procedure for treatment of open-angle glaucoma if medications inadequately control IOP levels. This procedure is commonly performed using either a cw argon laser or a cw diode laser. In this procedure, the laser energy is delivered gonioscopically using a contact goniolens. As illustrated in FIG. 2, laser energy 28 emitted from a laser (not shown) is focused onto a small diameter spot 30 on the trabecular meshwork 22. The laser energy 28 heats the meshwork tissue 32 until a white spot (or laser burn) is created. It is generally accepted that the laser burns cause shrinkage in the trabecular meshwork tissue 32. This shrinkage is believed to cause the meshwork tissue 32 disposed between the laser burns to stretch and become more open, thereby decreasing the resistance of the trabecular meshwork 22 to aqueous humor outflow thus reducing IOP. If effective, trabeculoplasty may reduce IOP by twenty to twenty-five percent. (See Taban et al., *The Importance of Lowering Intraocular Pressure*, Medscape Ophthalmology, Feb. 20, 2008)

Several issues can exist with laser trabeculoplasty. One issue is that the IOP lowering effect tends to disappear over time. IOP may only be adequately controlled for just a few years. Successive treatment may be limited without risking coagulative damage to the trabecular meshwork. Another issue that may be encountered with laser trabeculoplasty is pressure spiking. In the days following the trabeculoplasty procedure, the patient's IOP can rise above pretreatment levels. This pressure spiking requires careful monitoring and control. Other complications include iritis, hyphema, and development of peripheral anterior synechiae.

Another accepted method for treatment of open-angle glaucoma is invasive surgery. Trabeculectomy and tube shunts are the most typical procedures performed. In trabeculectomy, the surgeon removes a section of the limbal tissue underneath a scleral flap to create a path for aqueous humor to drain out of the eye and into a bleb formed by the conjunctiva to reduce IOP. Complications that can occur from trabeculectomies including hypotony, flat chambers, chorodial effusions, suprachoroidal hemorrhages, elevated IOP, hyphema, cataract, and infection. Tube shunts are most commonly used in open-angle glaucoma if trabeculectomy has failed. A tube is placed in the anterior chamber that allows aqueous humor to flow to an extraocular reservoir secured near the equator on the sclera to reduce IOP. Complications of tube shunts include overfiltration, tube-cornea touch, tube obstruction, tube erosion, tube migration, and ocular motility disorders. Other less common surgical interventions include ciliary body abalation, endocyclophotocoagulation, or cyclecryotherapy.

There exists a need to provide a non-invasive method, apparatus, and system for treating open-angle glaucoma which results in longer term IOP control and without side effects or issues that can arise from known methods, including medication, laser treatment, and surgery.

SUMMARY OF THE EMBODIMENTS

Embodiments of the present invention include methods, apparatuses, and systems for reducing intraocular pressure (IOP) levels in a patient as a means of either preventing or treating open-angle glaucoma. The breakthrough of the present invention is that heat, when applied at a temperature above body temperature and directed to the trabecular meshwork in the patient's eyes, can sustainably reduce IOP. The application of heat to the trabecular meshwork has the effect of loosening or relaxing protein clogs or blockages or other inhibitors in the trabecular meshwork that may either be reducing or obstructing of the outflow of aqueous humor thereby increasing the patient's IOP as a result. Preferably, the heat is directed to circumference area of the sclera in a line towards the trabecular meshwork and outside or out of line with the pupil and iris of the eye for safety reasons. This may also enable higher temperatures of heat to be applied to compensate for any heat transfer losses that may occur. The applied heat can be diffuse and non-focused to direct heat energy to the trabecular meshwork via intervening tissue.

Force can also applied to the patient's eye globe to apply pressure to the trabecular meshwork. Pressure can further assist in the loosening or relaxing of protein clogs or other inhibitors in the trabecular meshwork. The force may be increased and decreased continuously to provide a massaging force to the trabecular meshwork. The relaxation of protein clogs or blockages or other inhibitors has the effect of restoring the outflow of aqueous and sustainably lowering IOP for treating open-angle glaucoma.

In one embodiment, a patient is checked for signs of ocular hypertension (OHT) by first measuring the patient's IOP level. OHT can lead to the development of glaucoma or be an indication that glaucomatous eyes already exist in the patient. The patient's IOP level is diagnosed to determine if the IOP level is elevated or at an unsafe level. Normal IOP levels can vary with different patients and can vary based on a variety of factors, such as time of day, heart rate, respiration, exercise, fluid intake, systemic medication, topical drugs, alcohol consumption, etc. IOP also usually increases with age and thickness of their cornea, as examples. The patient is then diagnosed to determine if their IOP is elevated above their normal or expected IOP levels. If an elevated IOP is determined to exist, treatment may be administered in accordance with embodiments of the present invention. This includes applying a combination of regulated heat and/or force, including but not limited to a massaging force, to the patient's eye globe such that the heat and massaging force is applied to the trabecular meshwork. The temperature of the heat and/or the amount of pressure generated by the force may be regulated according to desired temperature and pressure profiles. Regulated heat and force may be applied at the same time or in serial fashion. The regulated heat and force may also be automatically applied by a device or system, manually, or a combination of manual and automated application. After heat and/or force are applied to the trabecular meshwork for the prescribed amount of time, the heat and/or force are removed from the trabecular meshwork. The patient's IOP is subsequently measured. If the patient's IOP level has been reduced to safe levels, treatment can end and a follow-up visit scheduled to monitor the patient's IOP level. If the patient's IOP level is not reduced to a safe level, treatment can be repeated during the same session or at a later time, as prescribed by the attending medical clinician or physician. Further, periodic follow-up visits and treatments may he desired or required to maintain the patient's IOP within safe levels.

A variety of devices may be used to apply heat and/or force to trabelcular meshwork. A heating and force application device may be employed that applies heat and force to the outside of the patient's eyelid, wherein the heat and force are directed to and applied to the trabecular meshwork. A heating and pressure regulating device or system may be used to control heat and force applied to the patient's eyelid. The heating and pressure regulating device may he provided in the form of goggles or other apparatus desired to fit over the patient's eye. A massaging force may be provided in the form of a vibratory force or pressure, or may be provided in the form of a gas or fluid jet that inflates and deflates a bladder placed against the patient's eye to provide a massaging force to the trabecular meshwork, as examples.

In another embodiment, a heat application device may be provided in the form of a lens with an embedded heating element. The heating element can be tightly regulated to prevent burning. The lens is placed inside the patient's eyelid and over top the sclera. The heating element contained inside the lens may be located around the circumference of the lens such that heat is applied proximate the trabecular meshwork but outside of the iris and pupil. Directing heat directly into the area of the iris or pupil may cause damage or may not allow the temperature of the heat to be transferred at the most effective levels to the trabecular meshwork. After heat is applied to the trabecular meshwork using the lens, the lens may be removed such that a force, such as a massaging force, can then be applied to the patient's eye to apply a force to the trabecular meshwork. As discussed above, applying a force to the trabecular meshwork can assist in the loosening or relaxing of protein clogs or other inhibitors that are reducing or preventing the outflow of aqueous humor through the trabecular meshwork and through Schlemm's canal. Before force is applied, the lens may be required to be removed since the lens structure may obstruct an applied force from reaching the trabecular meshwork when over top the patient's eye. Again, after treatment, the patient's IOP is subsequently measured. If the patient's IOP level has been reduced to safe levels, treatment can end and a follow-up visit scheduled to monitor the patient's IOP level. If the patient's IOP level is not reduced to a safe level, treatment can be repeated during the same session or at a later time, as prescribed by the attending medical clinician or physician. Further, periodic follow-up visits and treatments may he desired or required to maintain the patient's IOP within safe levels.

Those skilled in the art will appreciate the scope of the present invention and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the invention, and together with the description serve to explain the principles of the invention.

FIGS. 7-8 are block diagrams of a trabecular meshwork heating control circuit that may be employed in the trabecular meshwork heat and force application device of FIG. 6;

FIG. 9 is a goggle assembly for providing heat and massaging force treatment to the trabecular meshwork to treat open-angle glaucoma;

FIG. 10 is a close-up view of the goggle assembly of FIG. 9;

FIGS. 11-12 illustrate heating elements that may be used in a trabecular meshwork heating application device;

DETAILED DESCRIPTION OF THE PREFERRED EMBODIMENTS

Figure 1:
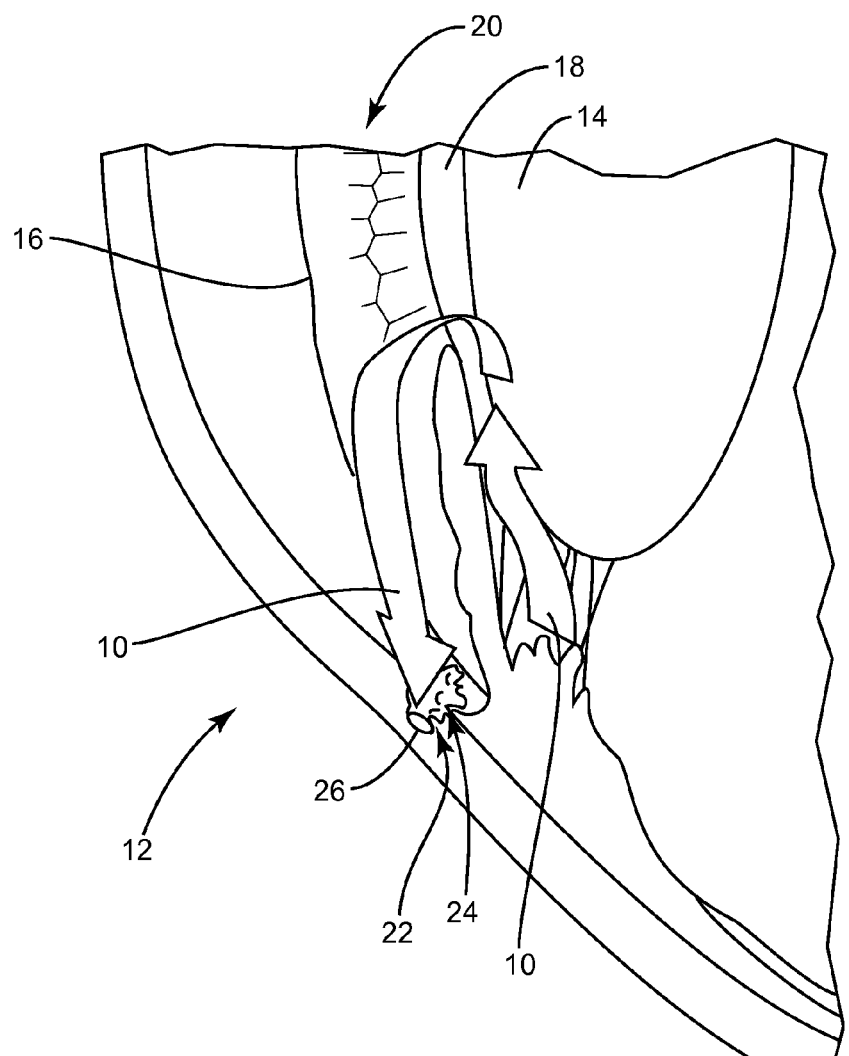
FIG. 1 is a close-up view of the lower front half of the eye illustrating circulation and drainage of aqueous in the eye under normal conditions.

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

Embodiments of the present invention include methods, apparatuses, and systems for reducing intraocular pressure (IOP) levels in a patient as a means of either preventing or treating open-angle glaucoma. The breakthrough of the present invention is that heat, when applied at a temperature above body temperature and directed to the trabecular meshwork in the patient's eyes, can sustainably reduce IOP. The application of heat to the trabecular meshwork has the effect of loosening or relaxing protein clogs or blockages or other inhibitors in the trabecular meshwork that may either be reducing or obstructing of the outflow of aqueous humor thereby increasing the patient's IOP as a result. Preferably, the heat is directed to circumference area of the sclera in as line towards the trabecular meshwork and outside or out of line with the pupil and iris of the eye for safety reasons. This may also enable higher temperatures of heat to be applied to compensate for any heat transfer losses that may occur. The applied heat can be diffuse and non-focused to direct heat energy to the trabecular meshwork via intervening tissue.

Force can also applied to the patient's eye globe to apply pressure to the trabecular meshwork. Pressure can further assist in the loosening or relaxing of protein clogs or other inhibitors in the trabecular meshwork. The force may be increased and decreased continuously to provide a massaging force to the trabecular meshwork. The relaxation of protein clogs or blockages or other inhibitors has the effect of restoring the outflow of aqueous and sustainably lowering IOP for treating open-angle glaucoma.

In one embodiment, a patient is checked for signs of glaucoma. Such signs can include ocular hypertension (OHT), which can be measured by measuring the patient's IOP level, or other factors such as reduced blood flow to the optic nerve area. OHT can lead to the development of glaucoma or be an indication that glaucomatous eyes already exist in the patient. The patient's IOP level is diagnosed to determine if the IOP level is elevated or at an unsafe level and/or if other glaucoma factors exist. Normal IOP levels can vary with different patients and can vary based on a variety of factors, such as time of day, heart rate, respiration, exercise, fluid intake, systemic medication, topical drugs, alcohol consumption, etc. IOP also usually increases with age and thickness of their cornea, as examples. The patient is then diagnosed to determine if their IOP is elevated above their normal or expected IOP levels. If an elevated IOP and/or other glaucoma factors are determined to exist, treatment may be administered in accordance with embodiments of the present invention. This includes applying a combination of regulated heat and/or force, including but not limited to a massaging force, to the patient's eye globe such that the heat and massaging force is applied to the trabecular meshwork. The temperature of the heat and/or the amount of pressure generated by the force may be regulated according to desired temperature and pressure profiles. Regulated heat and force may be applied at the same time or in serial fashion. The regulated heat and force may also be automatically applied by a device or system, manually, or a combination of manual and automated application. After heat and/or force are applied to the trabecular meshwork for the prescribed amount of time, the heat and/or force are removed from the trabecular meshwork. The patient's IOP can be subsequently measured as well as looking for other glaucoma factor signs. If the patient's IOP level has been reduced to safe levels and/or other glaucoma factors have been addressed to the satisfaction of the physician or technician, treatment can end and a follow-up visit scheduled to monitor the patient's IOP level and/or other glaucoma factors. If the patient's IOP level is not reduced to a safe level and/or other glaucoma factors are still of concern, treatment can be repeated during the same session or at a later time, as prescribed by the attending medical clinician or physician. Further, periodic follow-up visits and treatments may be desired or required to maintain the patient's IOP within safe levels.

The application of heat and/or massaging force to the trabecular meshwork to lower IOP in a patient's eye in a sustained manner was discovered as a result of conducting studies on patients. The study consisted of approximately fifteen patients. In the study, heat and pressure was applied to the patient's eye and directed towards the trabecular meshwork. Because force was being applied to the outside of the patient's eye globe as part of the treatment, the treatment causing increased IOP levels was of concern. Increased IOP levels can cause retinal damage thus impacting the visual function of the eye. Thus, the patient's IOP was measured before and after treatment to observe the results. The inventors expected the patient's IOP to be the same or slightly lower as a result of the treatment, because the massaging force was applied for longer periods of time than, for example, the force applied by a Honan balloon. A Honan balloon is a well-known device that is applied for short periods of time to a patient's eyes to reduce IOP just prior to surgery.

It was found that application of heat and massaging force to the patient's eye did in some cases result in a reduced IOP immediately following the procedure. It was then theorized that the drop in IOP levels would be short lived, because for example, the reduction in IOP levels as a result of employing the Honan balloon on a patient only lasts for approximately 1 to 3 hours. However, for some patients, the reduction in lop levels lasted for several months in some cases. This sustained reduction in IOP levels lead the inventors to theorize that the patient may have been suffering from abnormally elevated IOP levels that were either causing or could cause glaucoma. An analysis was performed to determine the reasons for the unexplained prolonged reduction in IOP levels as a result of applying heat and massaging force to the patient's eye. The analysis resulted as follows.

Figure 3:
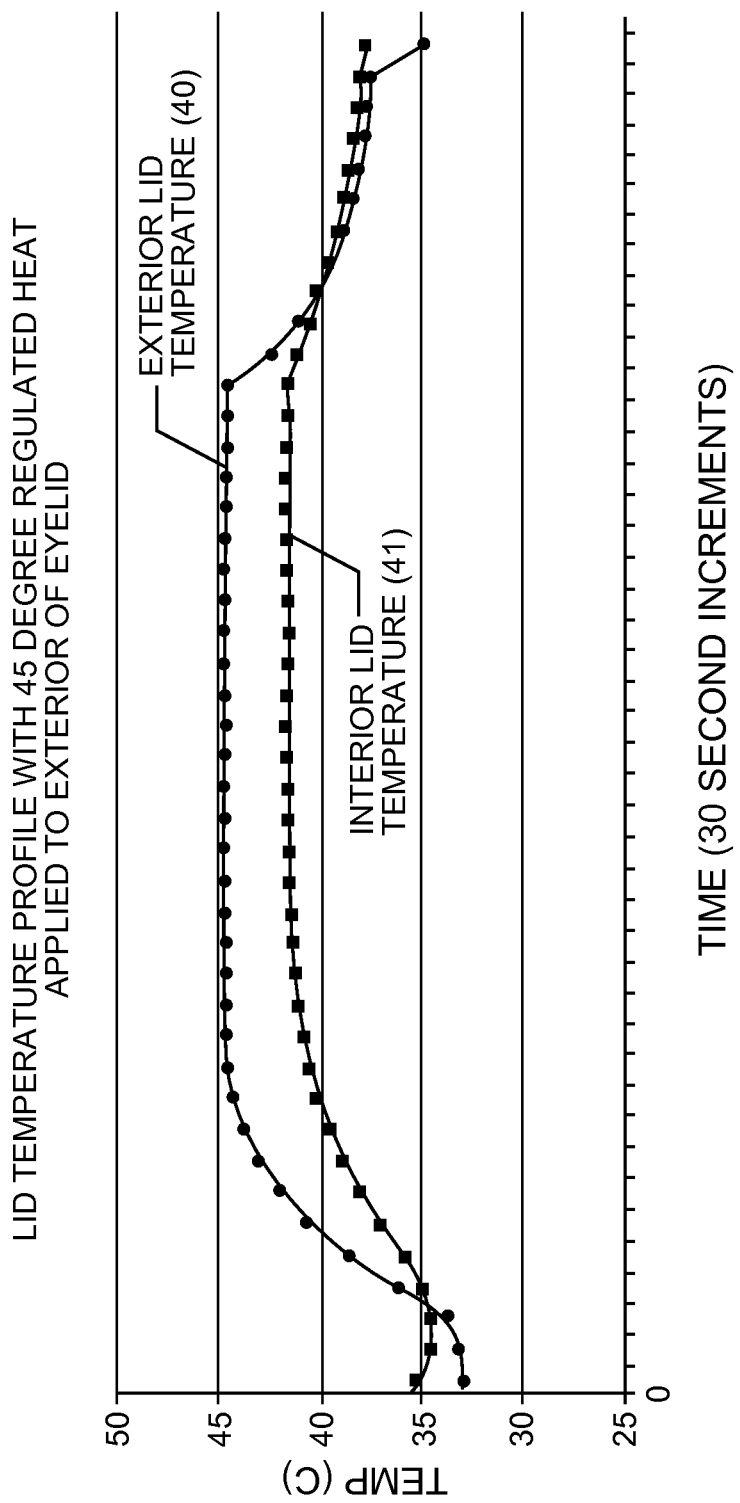
FIG. 3 is an exemplary eyelid temperature profile of an inner and outer eyelid temperature versus time when heat is applied to the exterior of the eyelid.

The application of heat and force to the patient's eye was theorized to be applying heat and force to the trabecular meshwork. FIG. 3 illustrates how the application of heat to the outside of the patient's eyelid results in increased temperatures inside the patient's eyelid at the actual eye, albeit with a temperature drop occurring across the eyelid. FIG. 3 illustrates a treatment temperature of 45 degrees Celsius applied to the outside of the patient's eyelid, as indicated, by curve 40. Curve 40 illustrates a relatively constant 45 degrees Celsius treatment temperature for a specified treatment time. The temperature at the inner surface of the patient's eyelid, indicated by curve 41, also increased as a result when heat was applied to the outside of the eyelid, albeit with as heat loss drop due to the heat loss from the transfer of heat from the outside of the eyelid to the eye. If heat is applied to the inside of the eyelid and to the trabecular meshwork, FIG. 3 illustrates that temperature losses will be reduced and thus requires either less heat and/or heat application for shorter periods of time for the heat to be transferred to the trabecular meshwork.

The application of heat and force to the trabecular meshwork is believed to have the effect of loosening or relaxing proteins or other inhibitors produced by and contained in the trabecular meshwork that have formed inhibitors and clogged pores. Clogged pores in the trabecular meshwork can reduce or obstruct secretion in the outflow pathway of the trabecular meshwork and thus reduce drainage of aqueous into Schlemm's canal. IOP rises as a result of blocked or reduced drainage of aqueous through the trabecular meshwork. By relaxing or loosening the proteins or other inhibitors in the trabecular meshwork, proper aqueous outflow is restored and elevated IOP levels as a result of the clogged drainage can decrease as a result. Loosening or relaxing proteins without damaging their physical cellular structure in trabecular meshwork can be performed.

For example, studies were discovered by the inventors that indicate the TIGR protein produced and located in the trabecular meshwork has been predicted to possess characteristics that could influence the outflow resistance in the trabecular meshwork. (see Booth et al., *TIGR and Stretch in the Trabecular Meshwork*, Investigative Ophthalmology and Visual Science, 40:1888-89, 1999) Characteristics of the TIGR protein include its oligomerization, specific binding to the trabecular meshwork cells, and potential interactions with other extracellular matrix molecules in the trabecular meshwork. Changes in TIGR protein properties due to structural mutations and/or its increased expression could be mechanisms involving outflow obstruction in the trabecular meshwork. These mutations can be associated with glaucoma. Id.

Figure 4:
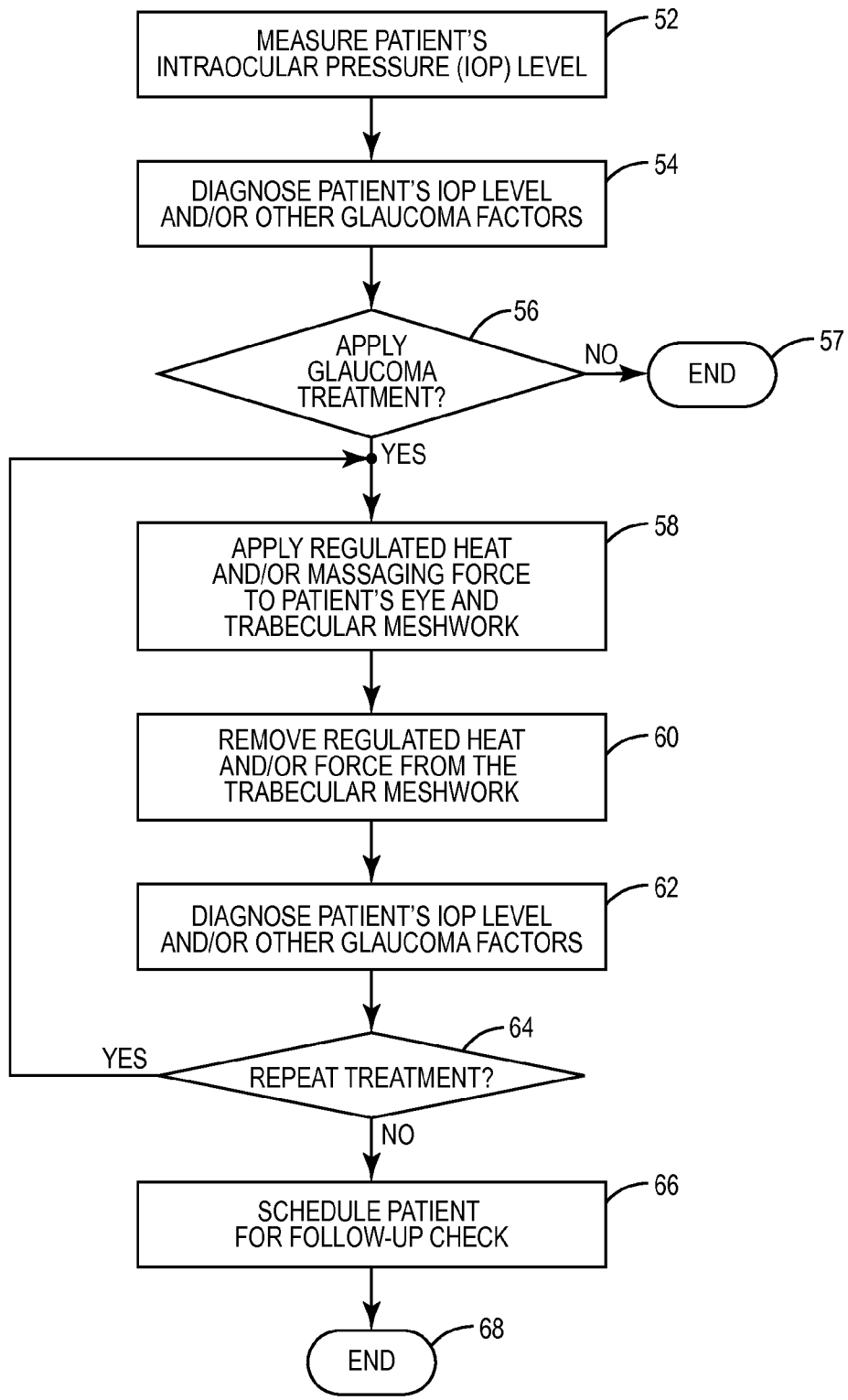
FIG. 4 is flow chart illustrating an exemplary process for measuring, diagnosing, and treating elevated IOP levels to either prevent or retard the further effect of open-angle glaucoma, according to one embodiment.

In this regard. FIG. 4 is a flowchart illustrating the steps of a basic embodiment of the present invention for diagnosing and treating elevated IOP in a patient as a means of either preventing or halting the effect of glaucoma to retard further vision loss. The process starts by a physician or certified clinician measuring the patient's IOP level to determine if IOP is at an elevated or unsafe level in the patient's eye (step 52). Any technology or methodology can be used to measure the IOP of the patient's eye. This includes applanation tonometry, electronic indentation tonometry, non-contact tonometry (pneumotonometry), and indentation (Schiotz) tonometry, as well known. Next, the physician or clinician diagnosing the patient determines if the measured IOP level is at elevated or at unsafe level and/or if other glaucoma factors exists, such as reduced blood flow for example (step 54). It is generally agreed that normal IOP levels for a patient is between 10 mmHg and 20 mmHg. The average value of IOP has been observed to be approximately 15.5 mm Hg with fluctuations of about 2.75 mmHg.

With regard to IOP, IOP levels can vary from patient to patient and based on a variety of conditions. For example, IOP can vary throughout the day and night. The diurnal variation for normal eyes is typically between 3 and 6 mmHg. This variation may increase for glaucomatous eyes. During the night, IOP usually decreases due to slower production of aqueous humor. IOP can vary with a number of other factors, such as heart rate, respiration, exercise, fluid intake, systemic medication, and topical drugs. Alcohol consumption can also lead to a transient decrease in intraocular pressure and caffeine intake may increase IOP. IOP may also become elevated due to anatomical problems, inflammation of the eye, genetic factors, as a side-effect from medication, or during exercise. IOP also usually increases with age. Corneal thickness and rigidity can also affect what is considered to be a normal IOP for a particular patient. The thicker the patient's cornea, the higher IOP may be and still be considered at a normal, safe level. Thus, when diagnosing the patient, the physician or clinician must take into account their experience and these wide range of factors to determine lithe patient's IOP is at elevated or unsafe levels such that treatment should be administered.

If the patient's IOP level is determined to be at a safe level and/or other glaucoma factors are such that treatment should not be administered (decision 56), the process ends (step 57). If on the other hand, the patient's IOP is determined to he at an elevated or unsafe level and/or other glaucoma factors exist such that treatment should be administered (decision 56), treatment according to the non-invasive treatment process and apparatuses according to the present invention may be used to lower IOP and sustainably over other methods. The treatment process in general is to apply regulated heat and/or force to the patient's trabecular meshwork in order to loosen or relax protein clogs or other inhibitors that are reducing or preventing normal outflow of aqueous humor (step 58). The applied heat can be diffuse and non-focused to direct heat energy to the trabelcular meshwork via intervening tissue. For the purposes of this application, to "loosen" or "relax" proteins or other inhibitors in the trabecular meshwork means to lessen the rigidity of any inhibitors such that outflow is increased. By sustainably, it is meant that IOP is reduced for periods of time, such as up to three months for example, although the present invention is not limited to any specific amount of time.

Any number of methods and devices may be used to apply heat and/or force to the trabecular meshwork. Examples of these methods and devices will he described through the remainder of this application. For example, the heat may be applied to the outside of the patient's eyelid or inside the patient's eyelid on the eye. As illustrated in FIG. 3 and previously discussed, the heat transfer characteristics to the trabecular meshwork will be different depending on which of these methods of heat transfer is employed. If heat is applied to the outside of the patient's eyelid, a greater temperature and/or duration of heat may he required due to the heat loss across the patient's eyelid. One reason contributing to heat loss is the intervening tissue of the eyelid between the heat application device and the patient's eye.

Also, it has been found that blood now through blood vessels in the patient's eyelid tends to act as a heat sink carrying heat away from the eye. If instead, heat is applied to the inside of the patient's eyelid on the eye, temperature and/or duration may be reduced while still attaining the same effective heat transfer to the trabecular meshwork. Regardless of where heat is applied by the heat application device, the temperature of the heat application device should he regulated such that the resulting heat that reaches and is applied to the trabecular meshwork is the desired temperature to be effective in loosening or relaxing protein clogs or other inhibitors in the trabecular meshwork.

It may only be required to increase the temperature at the trabecular meshwork a few degrees above body temperature (e.g. 40 to 44 degrees Celsius) for a sufficient period of time (e.g., 20 minutes) to loosen or relax protein clogs or other inhibitors in the trabecular meshwork. The goal is to apply heat sufficient to loosen or relax protein clogs or other inhibitors, but to not raise the temperature to a point where the proteins are damaged. Duration of heat as well as the application of force can interplay with heat transfer for an effective treatment. For example, a longer duration of treatment (e.g., 60 minutes) may allow the temperature of heat application to the patient's eye to he reduced (e.g., 42 degrees Celsius) while still providing an effective lowering of the patient's IOP, as opposed to a higher temperature of heat application e.g., 47 degrees Celsius) applied for a shorter period of time (e.g., 45 minutes).

Further, the application of force may assist the application of heat to sufficiently loosen or relax protein clogs or other inhibitors and reduce IOP as a result. For example, a force may be applied such that a pressure is applied to the trabecular meshwork. The application may also allow the temperature of the heat application and/or duration of application to be reduced from what it would otherwise be, to sufficiently loosen or relax protein clogs or other inhibitors and reduce IOP as a result. (e.g., 40-45 degrees Celsius for a duration of thirty (30) to sixty (60) minutes). The force may also be applied in the form of a vibratory or massaging force, to assist in the loosening or relaxing of protein clogs or other inhibitors. The force may also be applied either simultaneously during heat application, for a portion of heat application, or subsequent to heat application.

Turning back to FIG. 4, after the desired amount of heat and/or force combination has been applied to the patient's eye and thus the trabecular meshwork and for the desired duration, the heat and/or force application is removed from the trabecular meshwork (step 60). The physician or clinician then measures the patient's IOP level and/or determines if the glaucoma factors remain (step 62). The patient or physician determines if treatment should be reapplied or not during the same session based on the measured IOP level and/or analysis of other glaucoma factors (decision 64). The physician or clinician can check to determine if the patient's IOP level has lowered. However, the IOP level measured may still not be lowered to normal or safe levels to ensure the prevention of glaucoma or to retard its continued effect. If IOP level remains elevated beyond desired levels and/or other glaucoma factors exist in an undesired or unsafe manner, the physician or clinician can reapply treatment by repeating steps 58-62, as discussed above. If treatment should not continue (decision 64). treatment ends and the patient is scheduled for a follow-up visit in the future as part of monitoring the patient's IOP (step 66). It is important to continue to monitor the patient's IOP level over time to ensure that it remains lowered. The present invention has been shown to sustainably lower IOP, but inevitably, IOP levels may rise again such that periodic and continued treatment should be administered.

Figure 5:
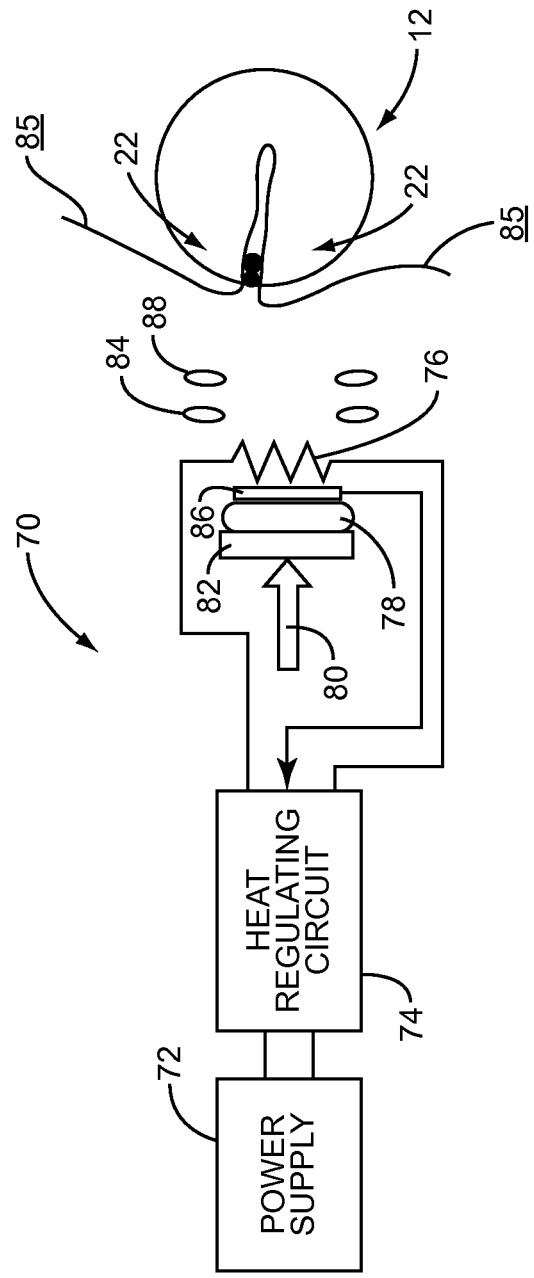
FIG. 5 is block diagram of a trabecular meshwork heating and force application device for treating open-angle glaucoma.

FIG. 5 illustrates a block diagram of one embodiment of a heat and force application device 70 that may be employed with the present invention to apply heat and/or force to the trabecular meshwork to reduce IOP. In this embodiment, the heat and force application device 70 applies heat and/or force to the outside of the patient's eyelid and in a direction towards the trabecular meshwork, such that heat and pressure is transferred and applied to the trabecular meshwork. The heat and force application device 70 directs diffuse and non-focused heat energy to the trabecular meshwork via intervening tissue in this embodiment. This may be desirable so that heat energy is not directed directly onto the trabecular meshwork risking damage to same, although the invention is not limited to diffused, non-focused heat energy. It is noted that this treatment (as well as the other treatments described and apparatus described herein) can be utilized or adapted for either the upper or lower eyelid, or both upper and lower eyelid for either left or right eye, or both left and right eyes. In this embodiment, a power supply 72 supplies power to a heat regulating circuit 74, which may be of any suitable design to provide heat regulation. This heat regulating circuit 74 applies an electrical signal such as a current (AC, DC, pulsed, programmed or modulated) to a heating element 76 (e.g., a flexible foil heater element that produces heat by virtue of the heat produced when current passes through a resistor, i.e., resistive heating) in order to produce a regulated temperature transfer to the trabecular meshwork within the therapeutic range (e.g. 40-45 degrees Celsius). This heating element 76 is used to generate the heat which ultimately is transferred to the trabecular meshwork for heat therapy.

In the present embodiment, a heat sink 84 is disposed between the heating element 76 and eyelid 85 of eyeball 22. The heat sink 84 is show in a cross-section view to illustrate that the heat sink 84 is preferably in the shape of a ring with a void in the center. Although not limiting, this is so heat is preferentially directed to the circumference area of the sclera in a line towards the trabecular meshwork and outside or out of line with the pupil and iris of the eye for safety reasons. This may also enable higher temperatures of heat to be applied to compensate for any heat transfer losses that may occur. This heat sink 84 may be either, for example, a flexible silicon member that flexes (along with the heating element in some embodiments) to conform to the shape of the eye being treated. In one embodiment, a flexible silicone rubber pad that is relatively thermally conductive (e.g., one or two layers 1/16 inch thick) can be used. Alternatively, the heat sink 84 may be a rigid or relatively rigid thermally conductive member, which is pre-shaped to closely conform to the outer surface of the eyelid 85. In this embodiment, one typical size or multiple sizes may be provided to match the eyeball contour and apply heat to both the upper an lower lids simultaneously, which could then apply heat to the trabecular meshwork through a single eyelid of a single eye or both eyelids of a single eye, or a single eyelid of both eyes or both eyelids of both eyes.

In this embodiment, the heating element 76 is sandwiched between the heat sink 84 and an insulator 78. Insulator 78 serves to minimize heat loss from the back side of the heating element 76, and thereby assists in channeling heat from the heating element 76 through the heat sink 84 to the eyelid 85. In certain embodiments, a backing plate 82 is optionally applied to the outer surface of the thermal insulator 78 in order to assist in attaching the assembly to the eyelid or otherwise contacting and engaging the eyelid 85, as will become clear later. In certain embodiments, a slight force, illustrated by arrow 80, urges the heat sink 84 into close contact with the eyelid 85 in order to more efficiently transfer thermal energy to the trabecular meshwork while also applying three to the trabecular meshwork to urge the loosening or relaxing of protein clogs or other inhibitors in the trabecular meshwork.

In accordance with certain embodiments, the heating element 76 is realized as a flexible foil resistive heating element. Such elements comprise a flex-circuit having resistive pathways through which electrical current is passed to cause generation of resistive heat. In such heating elements, the temperature can often be monitored by measurement of the resistance of the element, which changes somewhat as the element heats up. Resistance can be measured in a number of ways including indirectly by measuring the current flow to the heating element and/or the voltage applied across it. Hence, in such heating elements as used in this particular embodiment, the primary or only mode of heat production is via direct contact of the heating unit with heat provided by resistive heating and production of potentially harmful infrared light energy is minimal or non-existent. Additionally, the heating element 76 may be realized as a collection or array of heating elements without limitation. Each of these variables and others will occur to those skilled in the art upon consideration of the present teachings. Other types of resistive heating elements may also be used without departing from embodiments consistent with the present invention.

The circuit depicted in FIG. 5 is general in nature and may utilize many variations consistent with embodiments of the present invention. In one embodiment, a fixed temperature device, such as that illustrated in FIG. 5, may be utilized in which the heat regulating circuit 74 is factory calibrated to produce the desired constant therapeutic temperature at heating element 76. This constant therapeutic temperature can be factory calibrated by measurement of the temperature and resistance of the heating element 76 or heat sink 84 so that a safe and therapeutic level of heat is obtained. A selection of heat settings can be provided for use by the clinician or physician. The heat regulating circuit 74 may also incorporate a timer so that heat is applied for a specified period of time once the heating cycle starts, and the heat is terminated after the specified treatment time. In addition, the heat regulating circuit 74 may trigger an alarm notifying the user of an end of the treatment period when the specified treatment time has expired. In general, a treatment time of about thirty minutes has been found to be satisfactory, but a great deal of variation and optimization may be possible without deviating from the present invention. Generally, times ranging between about thirty (30) and sixty (60) minutes are appropriate, depending upon the severity of protein clogs or other inhibitors in the trabecular meshwork and temperature, but this should not be considered limiting.

For purposes of this document, the insulator 78 is suitably insulative so as to tend to serve as a barrier to the escape of heat from the rear of the heating element 76, whereas, the heat sink 84 should be suitably conductive so as to tend to draw heat from the heating element 76 toward the eyelid 85. In embodiments where contact with the human eyelid is desired, it is often desirable that the heat sink 84 or other element placed in contact with the eyelid 85 be soft and comfortable. This may limit the actual absolute thermal conductivity of that material. However, so long as there is a reasonable tendency for heat to flow through the material, it will be considered a heat sink. Similarly, the insulator 78, due to similar restrictions as well as size, is unlikely to resemble an ideal insulator, but keeping the heat adequately directed toward the eye 12 with a reduction in heat loss over the bare heating element 76 is adequate to be considered an insulator. The relative thermal conductivity of the heat sink 84 can therefore he greater than the thermal conductivity of the insulator 78, and preferably it should be much greater (e.g., a factor of 10). That is, the insulator 78 should preferably be less conductive of heat than the heat sink 84.

In prototypes, the insulator 78 had thermal conductivity of approximately 0.10 W/mK (watt per meter-Kelvin), while the heat sink had a thermal conductivity of approximately 1.3 W/mK. However, these conductivity values should not be considered limiting. In certain embodiments, the hacking plate 82 may serve adequately to provide the function of the insulator 78.

It will be appreciated by those skilled in the art that the terms "heat sink" and "thermal insulator" arc relative terms that describe the tendency of a material, in any form, to either absorb and transfer heat or inhibit the flow of heat. For example, the insulator 78 can also be provided in the form of an air or other gas pocket.

For purposes of this document, the term "heat sink" will suggest that the substance in question is a relatively good conductor of heat (compared to the insulator utilized). For materials such as thermally conductive silicon rubber, heat conductivity is generally better than that which would be considered a thermal insulator, even though it may not be as good as a metal such as steel or aluminum. However, commercially available materials that are designed for enhanced thermal conductivity are available and are made of flexible material such as silicon rubber. Similarly, most "thermal insulators" will inherently conduct a certain amount of heat. This fact will not preclude a material from being considered a thermal insulator for purposes of this document. Thermally insulating materials such as insulating foam rubber and plastics and the like are commercially available.

One example of a thermally insulating material suitable for use in embodiments of the present invention is neoprene rubber with a thickness of approximately ⅛ to ¼ inch, but these dimensions should not be considered limiting. Thermally conductive silicone rubber materials can be obtained commercially from a number of sources including, for example, Stockwell Elastomerics, Inc. of 4749 Talbut Street, Philadelphia, Pa. 19136 as product T100.

The heat and force application device 70 may also include a separate temperature sensor 86 adjacent to the heating element 76. This temperature sensor 86 is shown for convenience as occupying a separate layer in the structure, but this is merely for convenience of illustration. Temperature sensor 86 could be placed anywhere between the insulator 78 and the heat sink 84, between the heating element 76 and the heat sink 84, between the heating element 78 and the insulator 78, embedded within the heating element 76, embedded within the heat sink 84, or at the surface of the eyelid 85, without limitation, so as to read the temperature being generated by the heating element 76 and/or delivered to the outer surface of the eyelid 85, which is transferred to the trabecular meshwork. If the heat sink 84 and insulator 78 properly do their job, any of these points can be used to measure the temperature that is ultimately delivered to the outer surface of the eyelid (or can be calibrated to represent the final eyelid surface temperature to a reasonable degree of accuracy (after a settling time period).

The temperature sensor 86 may be realized as an array of sensors in certain embodiments. Temperature sensor 86 sends an electrical signal back to the heat regulating circuit 74 so that the heat regulating circuit 74 can monitor the actual temperature generated by heating element 76. Feedback control techniques can then be utilized so that proper heating within a therapeutic range is maintained at heating element 76. Temperature sensor 86 may be realized in a number of ways including, but not limited to, a thermocouple (e.g., the extremely small thermocouples available from Physitemp Instruments Inc. of 154 Huron Avenue, Clifton, N.J. 07013) or a conventional miniature thermistor.

The heat and force application device 70 illustrated in FIG. 5 may also include a vibratory element 88. The vibratory element 84 generates a vibratory force towards the eyelid 85 and to the trabecular meshwork to aid in the loosening or relaxing of protein clogs or other inhibitors in the trabecular meshwork, as previously described. The vibrating element 88 is show in a cross-section view to illustrate that it is preferably in the shape of a ring with a void in the center. Although not limiting, this is so vibratory force is preferentially directed to the circumference area of the sclera in a line towards the trabecular meshwork and outside or out of line with the pupil and iris of the eye for safety reasons. The vibratory element 88 is optional, and may or may not be activated during heat application by the heating element 76. For example, the vibratory element 88 may be activated after the heat regulating circuit 74 is controlled to deactivate heating, such that the heat and vibratory force are applied to the trabecular meshwork at different times.

Figure 6:
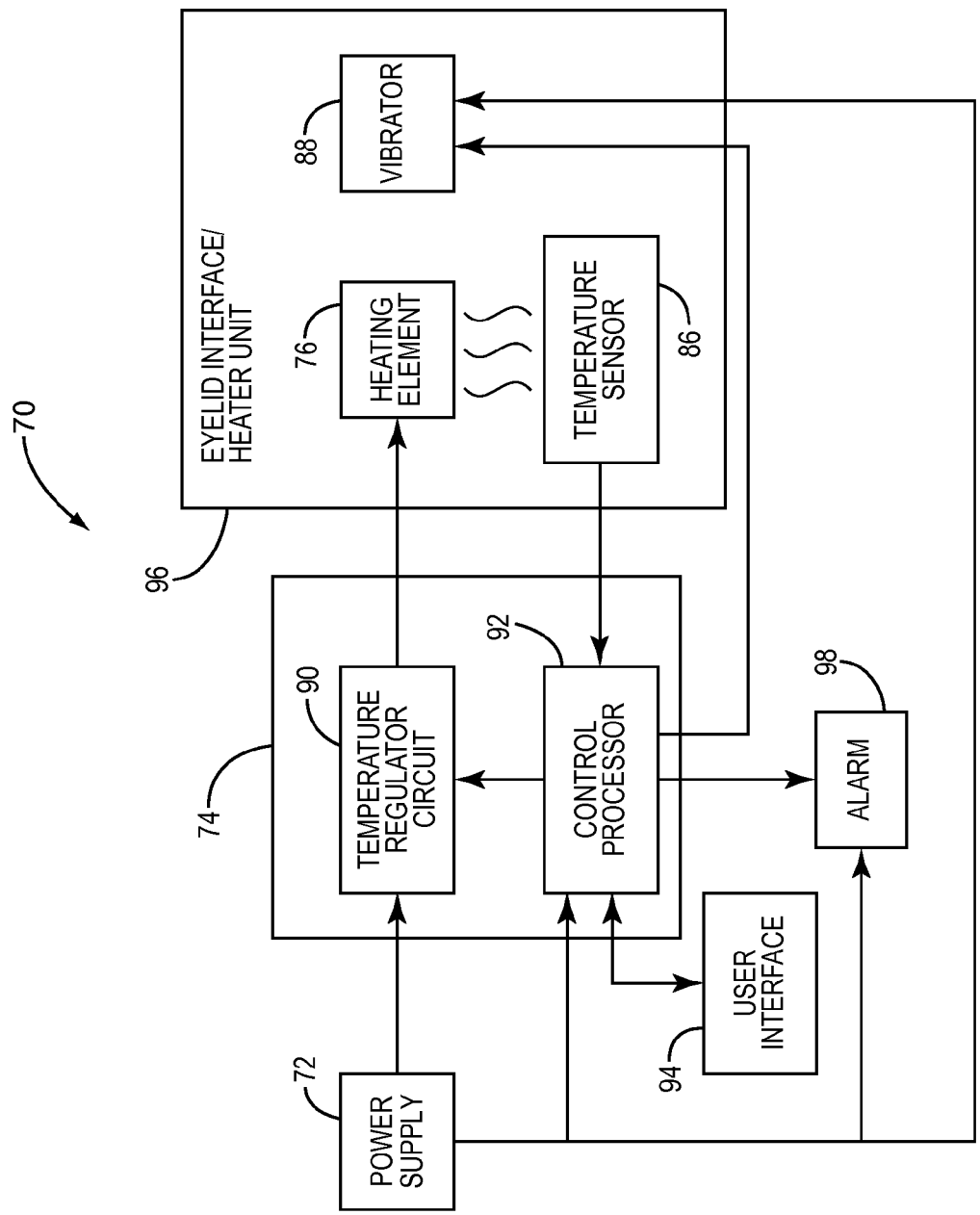
FIG. 6 is an expanded block diagram of a trabecular meshwork heat and force application device of FIG. 5.

FIG. 6 illustrate block diagram of the heat and force application device 70 components consistent with FIG. 5 to further illustrate this embodiment. A heater unit 96 incorporates (in addition to a thermal heat sink 84, insulator 78, backing plate 82, etc.) heating element 76, along with a separate or integral temperature sensor 86 and the vibratory element 88, which all form a part of the heater unit 96, which is placed in contact with the eyelid. In this embodiment, a control processor 92 uses a temperature regulator circuit 90 (such as those previously described or other design) to form the heat regulating circuit 74. Power supply 72 supplies power both to the heating, element 76 and the control processor 92, as well as being able to supply power to the vibrating element 88 and an optional alarm 98. In this embodiment, a user interface 94 (e.g., which may incorporate display) may be supplied, in which the user may interact with the control processor 92 in order to control various aspects of the operation of the device 70. In one embodiment, for example, the user interface 94 may be utilized to adjust the treatment time, temperature, and application of force, including control of the vibratory element 88. Elements of this and other embodiments may be freely interchanged without departing from the invention.

For purposes of this document, it is useful to define vibratory energy as mechanical motion having a frequency component and an amplitude component. It is currently believed to be most desirable that the frequency component be between approximately 0.1 Hz and 300 Hz and include random oscillations, and that the amplitude component be defined as the amount of displacement in the direction of the trabecular meshwork 22, which is preferably up to about 3 mm, with a currently preferred deflection being about 0.5 mm. However, this should not be considered limiting since optimization of these parameters and definition of a suitable profile may be optimized by experimentation. In one embodiment, for example, the temperature profile might be to establish a constant temperature of 45 degrees Celsius for thirty (30) minutes with application of linearly increasing vibratory energy from 0.1 Hz to 300 Hz and over the last five (5) minutes the amplitude of the vibratory energy decreasing front 3 mm to 0 mm linearly. The actual profiles used can be optimized experimentally after considerations of the teachings provided herein.

As noted earlier, the heating profile of the heating element 76 used in prototypes produced a temperature gradient of several degrees Celsius across the eyelid. Prototypes utilized Minco Thermofoil Heater HK5207R6.5L12A. While quite functional, this heating element 76 did not have an ideal temperature profile and thus only heated a portion of the eyelid.

FIGS. 7 and 8 illustrate further embodiments for controlling the application of heat that may be employed in the heat regulating circuit 74 illustrated in FIGS. 5 and 6. In the embodiment of FIG. 7, the heat regulating circuit 74 is implemented by use of the control processor 92, which received feedback information from temperature sensor 86 and utilizes this information to control a temperature regulator circuit in the form of a switch 90' that applies power to the heating element 76 in order to regulate the temperature of the heating element 76. While this embodiment depicts the heating element 76 and temperature sensor 86 as being two separate devices, as previously indicated, the resistance of the heating element 76 or other characteristics of the heating element 76 can also be utilized for purposes of sensing the operational temperature of the heating element (s). Control processor 92 operates using an internal or external clock (not shown) so that it may further provide control of the amount of time in which the heating element 76 is activated and may provide an alarm in the event of a malfunction or in the event of the end of the specified treatment periods. Other functions may also be carried out with control processor 92 without departing from the present invention.

FIG. 8 depicts a further embodiment of a mechanism for regulating the temperature of the heating element 76. In this embodiment, the control processor 92 similarly controls the operation of the heating element 76 based upon temperature sensed by either a separate temperature sensor 86, or by the heating element 76 itself. This information is used to control a heat regulating circuit in the form of a pulse width modulator 90". By increasing the width of the pulses produced by pulse width modulator 90" (i.e., increasing the duty cycle), the heating element 76 will produce more heat, and reducing the width of pulses produced by pulse width modulator 90" will reduce the temperature of heat generated by heating element 76. Other modulation schemes, including but not limited to a variable voltage and/or variable current source may also be utilized to regulate the heating of the heating element 76 without departing from the present invention. Again, control processor 92 may also control other functions, as will be discussed later.

FIG. 9 illustrates one embodiment of the heat and force application device 70, consistent with embodiments of the present invention is depicted in which a separate housing 99 is used to house the power supply 72 and the temperature regulating circuit 90. This housing 99 can be attached by wiring 100 to the heater unit 96 and by wiring 101 to the vibratory element 88, if present. Alternatively, the power supply 72 and the heat regulating circuit 74 can be embedded within the goggle assembly or a helmet-like assembly. Heater unit 96 incorporates some or all of the elements described in FIGS. 5 and 6 (as well as variations described later) with the outer surface of the heat sink 84 providing an interface to the eyelid 85. Heater unit 96 could incorporate the heat sink 84, the heating element 76, possibly temperature sensor 86, as well as insulator 78 and backing plate 82. One or two layers of a 1/16 inch thick silicon rubber heat sink can be used. The backing plate 82 in the present embodiment is utilized to affix a ball 104 to a captivating socket in the backing plate 82 so that the heater unit 96 can be rotated and otherwise adjusted with respect to a holder (e.g., goggles as will be described) to appropriately contact the eyelid 85 to transfer heat to the trabecular meshwork. The ball 104 is in turn connected to a threaded shaft 106 which has a wing nut, thumbscrew, or other conveniently manipulated termination 108 so that the user, clinician, nurse, physician or clinician can screw the shaft 106 in to adjust the contact with the eyelid 85 and thereby adjust the initial pressure placed on the eyelid 85 by the heater unit 96. In this embodiment, the shaft 106 is screwed through a lenspiece 112 forming a part of a goggle 110 which the user straps to the patient's head using adjustable straps 114 in a more or less conventional manner.

In certain embodiments, the heat sink 84, or the entire heater unit 96 or portions thereof may be made disposable so that the regulator and other parts may be re-used with multiple patients, while remaining sanitary.

For purposes of this document, goggles 110 are used as an illustrative embodiment of a holder or interfacing mechanism that keeps the heater unit 96 in place, but other mechanisms are also possible. Thus, the use of the term "goggle" for descriptive purposes shall be considered to be any type of goggle, frame, headgear, goggle-like headgear, helmet, strap, or other device that fits on a patient's head in any manner and can be utilized to hold a heater unit, such as 96, in contact with a patient's eyelid 85 during treatment, as described herein. A goggle's lenspiece 112 as discussed is defined as an element of the goggle 110 or other device that is situated approximately where a lens would normally reside in front of the eye 12, and does not necessarily imply the presence of an actual optical lens.

In this embodiment, goggles similar to those used for swimming can be adapted to carry the heater unit 96 and hold it in proximity to the eyelid 85 being treated during the specified treatment time. While the goggles 110 illustrated in FIG. 9 are more or less conventional goggles, such as those used for covering the eyes during swimming, any other suitable mechanism for holding the heater unit 96 in place at one or more of the eyelids to be treated can be utilized, including adhesives, tapes, straps, helmets, clamps or any other suitable expedient. Each such mechanism can be considered a suitable interfacing mechanism for purposes of this document.

FIG. 10 illustrates a further embodiment of a heat and force application device 70 depicted. An exemplary vibrating element 88 is incorporated within the apparatus. In this embodiment, a generic vibrator 88 is depicted as embedded within an eyepiece 102. Further, the eyepiece 102 is preferentially shaped in the form of a ring 103 with a void 105 in the center so heat and force are preferentially directed to the circumference area of the sclera in a line towards the trabecular meshwork and outside or out of line with the pupil and iris. However, this embodiment could include a solid eyepiece 102 as well, if temperature and force are monitored and controlled such that any heat or force reaching the iris or pupil does not inflict damage. Such vibrating element 88 can be of any suitable design. There are multiple mechanisms that can be utilized, to provide vibratory energy to the heated eyepiece 102. Examples, which should not be considered limiting, are as follows:

First, an offset motor can be used and attached to the outer surface of the eyepiece heater unit 96 or shaft 106. Some such offset motors operate by having an eccentric weight attached to the shaft that causes vibration when the motor is powered. An offset motor is used in cellular telephones and beepers to alert the user. They are readily commercially available in different sizes and can operate to produce vibrations at various different frequencies and amplitudes. An appropriate frequency and amplitude can be determined by experimentation upon consideration of this teaching.

Button type vibration motors can be embedded within the eyepiece 102 or otherwise attached in a manner operative to induce vibration. A small motor can also be placed on the threaded shaft 106 which attaches to the goggle/mask 110 and heater unit 96. The motor can then be used to rotate a figure eight screw causing it to move in and out. The amount of displacement in this case is fixed but the speed (frequency) can be controlled with a micro-processor unit. Further, a small piezoelectric motor can be used to move the threaded shaft 106 which attaches to the goggle 110 and heater unit 96. The amount of displacement and frequency of operation can be controlled with a microprocessor unit.

The threaded shaft 106 between the lenspiece 112 and the heater unit 96 can be removed and replaced with a diaphragm. The diaphragm can be placed between the goggles 110 and the heater unit 96, attached to both. A simple pulsating gas (e.g., air) or fluid pump can be used to inflate and deflate the diaphragm thus providing mechanical motion to the heater unit 96. The amount of gas or fluid and frequency of pulses can be controlled by a microprocessor unit.

Other embodiments wherein mechanical energy, where mechanical energy is defined as any form of mechanical pressure on the trabecular meshwork to assist in loosening or relaxing protein clogs or other inhibitors is applied using any suitable mechanism can be devised upon consideration of the present teachings. Once the heating element 76 has served to loosen or relax protein clogs or other inhibitors in the trabecular meshwork, application of mechanical energy such as pulsing, vibratory energy, milking, etc. action to the eyelid can further assist in stimulating the protein clogs or other inhibitors to assist in loosening or relaxing protein clogs or other inhibitors in the trabecular meshwork to restore the flow path for aqueous humor.

FIG. 11 depicts one example of a heating unit 96' employing a heating element 76' that is customized for heating the eyelid 85 and transferring heat to the trabecular meshwork. Such heater element design 76' can be fabricated by foil heater companies such as Minco of 7300 Commerce Lane, Minneapolis, Minn., 55432. In this embodiment, the outside profile of the heater element is designed to fit the contour of the lower eyelid 85, but other designs can be devised to treat the upper eyelid or both eyelids 85 simultaneously. One typical set of working dimensions for such a heater design is approximately 1.8 inches for dimension 124 approximately 1.015 inches for dimension 126 and approximately 0.375 inches for the tab 120 at dimensions 128 and 130. Of course, these dimensions should not be considered limiting, but are believed to be suitable for an average sized human eyelid. This design provides tab 120 that is bent back at about 90 degrees away from the eyelid 85 and provides for attachment of wires 118. Additionally, tab 120 and the shape of the foil heater reduces the unevenness of heating across the eyelid noted in standard commercial foil heaters that were tested.

In accordance with certain embodiments, a heater unit 96" (e.g. as in FIG. 12) may be attached with wires 118 coupled to the heating element 76" and a plug connection to the temperature regulator circuit 90, so that the heater unit 96" may be detached for cleaning, or for disposal at a portion at (e.g., the heat sink), or the entire heater unit 96. In this manner, sanitation can be maintained while portions of the apparatus can be reused, and speed of treatment enhanced.

The heating is resistive heating produced by the resistance of the conductive path between the conductors that terminate at tab 120. In this embodiment, the heating path meanders left to right and right to left to provide the resistive path producing the heat. In other embodiments, the resistive path can meander up and down and down and up to produce the resistive path as depicted in FIG. 12. Many other patterns can also be used. The dimensions and precise layout of the paths are designed to maintain distance between conductors, line width and resistance appropriate to generate the required heat with an even heating profile, utilizing conventional design principles for foil heater or other resistive heater designs. Moreover, other heating technologies other than foil heaters and other than resistive heating can be used without departing from the present invention.

Those skilled in the art will appreciate upon consideration of the present teachings that many variations in the embodiments depicted are possible without departing from the present invention. For example, the heating element 76 should preferably provide heat to the eyelid 85 that is directed to the trabecular meshwork 22 preferably without being directly directed to the iris or pupil, and this may be accomplished, using an array of heating elements rather than a single heating element. The heating element 76 is preferably a flexible heating element, such as a foil heating element, to assist with conforming to the shape of the eyelid 85. However, the heating element 76 may also be rigid and provided in preformed shapes to conform with one average or a variety of eyelid shapes and sizes. Alternatively, a rigid heating element 76 may be accompanied by a soft heat sink 84 which would conform to the eyelid 85. As discussed earlier, this heat sink 84 can be made of a thermally conductive rubber, a fluid, gel or gas filled diaphragm, a damp cloth, or any number of materials which would be thermally conductive and readily conformable.

The heat sink 84 may be made of thermally conductive rubber or silicon or can be an encapsulated fluid or gelatin. In other embodiments, the heat sink 84 can be a solid thermally conductive material which is appropriately shaped to conform to the eyelid geometry (i.e., conform to a surface that is approximately a section of an oblique spheroid). The insulator 78 can be made from a nonconductive rubber or foam material (where nonconductive is intended to mean low thermal conductivity) or may be made from a low thermal conductivity solid material. The heating element 76 may be used in conjunction with a thermal conductive gel, liquid, or cream to fill gaps between the heat sink 84 and eyelid 85 in order to provide a more uniform conductive boundary between the eyelid 85 and the heater unit 96. Alternatively, sweat produced from heating the lids inherently assists in increasing heat transfer and is a byproduct of using a nonabsorbent heat sink like thermally conductive silicon rubber. The layers depicted can be integrated together in any suitable manner and may take any other form suitable to the end purpose of providing relatively uniform regulated heating of the eyelid.

The temperature regulating circuit 90, which regulates temperature of the heating element 76, and if present the vibratory element 88, may be operated under computer control and may have temperature set points and vibratory set points including amplitude and frequency that are adjustable by the user. Additionally, if desirable, a variety of temperature profiles and/or mechanical energy profiles can be implemented under computer control where the temperature and vibratory energy can be ramped up and/or down over time if this is deemed to be a desirable control feature. The temperature regulator 90 and/or mechanical energy element can also operate on a timer to limit the time limit of the treatment. While pulse width modulation and simple on/off switching have been disclosed for regulating the temperature of the heating element, other embodiments will occur to those skilled in the art upon consideration of the present teaching. In accordance with certain embodiments, this heat regulation and/or mechanical energy regulation may be carried out under control of a computer, such as a microprocessor operating under control of a computer program stored as instructions in an electronic computer readable storage medium, such as a read only memory (ROM) or other suitable storage medium.

The power supply 72 may utilize batteries which may be replaceable or rechargeable, or the power source may utilize AC power which may be converted to DC as needed for implementation of the device.

Any suitable mechanism can be utilized for attaching the heater unit 96 to the eyelid 85. As disclosed above, this can be done with double sided medical tape or with a head piece, such as goggles 110, to hold the heater unit 96 in place. In other embodiments, the heater unit 96 may be strapped in place, held in place by the bridge of the nose, swiveled into place, screwed into place by means of a goggle mechanism, latched into placed, or utilizing any other suitable adjustment mechanism from goggles or other head gear. Such mechanism serves to adjust the amount of force placed on the eyelid from the heater unit 96. In other embodiments, a mechanism may also be devised which automatically adjusts the force placed on the eyelid 85, and the mechanism may be included either within the heater unit 96 or otherwise coupled to the heater unit 96 (for example, in the goggles 110) to transmit mechanical energy to the heater unit 96.

Figure 13:
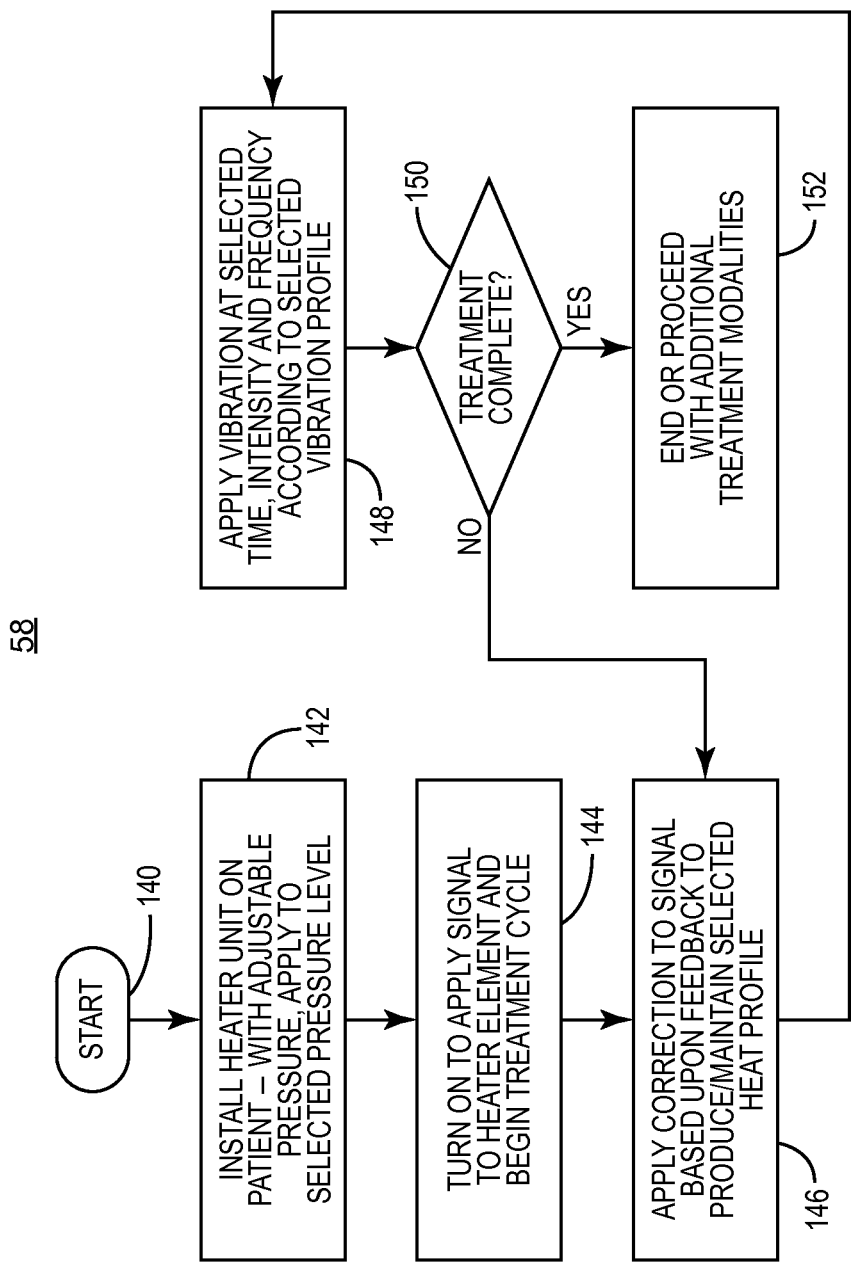
FIG. 13 is a flow chart illustrating an embodiment of a process for applying heat and vibratory force to the trabecular meshwork to treat open-angle glaucoma.

With reference to FIG. 13, one can envision any number of treatment regimens that can be carried out using the various embodiments disclosed. This flow chart depicts the general process one would go through to carry out a treatment in accordance with certain embodiments, and to perform step 58 in FIG. 4, for example. First, the heater unit 96 is installed onto the patient (e.g., using the goggle 110 arrangement or adhesive arrangements depicted) (step 142). In those embodiments in which force can be applied, the pressure is adjusted to urge the heater unit 96 into contact with the eye 12 or eyelids 85 to be treated with a selected measure of gentle force. The heater unit 96 can then be turned on and the treatment cycle begins according to a manual or automated process (step 144).

Once the heater unit 96 reaches an appropriate treatment temperature (e.g., 45 degrees Celsius), feedback control is utilized to maintain the heat at a constant level or to achieve a desired heat treatment profile (step 146). Similarly, at a desired timing of the treatment profile, mechanical energy can be added (if the embodiment of the heater unit 96 is so equipped) (step 148). it currently appears that best results can be achieved when mechanical energy is applied when the therapeutic temperature is reached and discontinued shortly after the heat therapy is completed. This process proceeds according to the selected treatment profile (either selected by an operator or pre-programmed) until the treatment profile is complete (decision 150). The treatment then either ends or additional treatment is resumed (step 152).

Thus, a method of treating at least one of a patient's eyelids with a regulated heat in a manner consistent with certain embodiments involves: placing a heating unit 96 having a heating element 76 in contact with the patient's eyelid to transfer heat to the trabecular meshwork; and applying a control signal to the heating element 76 to generate heat at the heating element 76 and transfer the generated heat to the trabecular meshwork for a prescribed time period.

Figure 14:
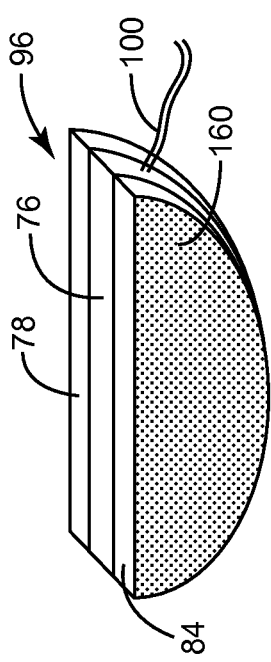
FIGS. 14-16 illustrate various trabecular meshwork heat application device assemblies that may be used to treat open-angle glaucoma.

Referring now to FIG. 14, a heating unit 96 consistent with certain embodiments is depicted in which again a layered sandwich style assembly is depicted with an insulator 78 providing a rearmost layer, the heating element 76 providing a central layer, and the thermal heat sink 84 providing a front layer, which will be placed in contact with the eyelid 85. The heating unit 96 is also a diffuse and non-focused heat source. In this embodiment, an adhesive 160 is applied to the outer surface of the heat sink 84 in order to affix the heater unit 96 to the eyelid 85. In this example, the adhesive 160 may be in the form of a double-sided adhesive tape, which has a cover that is peeled off to reveal the adhesive in order to affix the heater unit 96 to the eyelid 85. In the example depicted, the thermal heat sink 84 may be flexible or pliable so that when pressed in place it conforms to the shape of the eyelid 85 to provide close contact between the thermal heat sink 84 and the eyelid 85. However, in other embodiments, the surface carrying the adhesive 160 may be shaped in a manner that conforms with the up and down, as well as top left and right curvature of the eyelid to be treated. In this example, thermal heat sink 84 can be rigid rather than pliable. A somewhat half-moon shape is depicted for ease of illustration, but the shape is preferably one which closely conforms to the shape of an eyelid or pair or eyelids 85. In particular, since the lower eyelid is generally most problematic, a suitable shape to conform to the lower eyelid 85 is desirable.

When using any adhesive mechanism to attach the heater unit 96, it is desirable to clean and dry the surfaces to which the adhesive is applied in order to remove all body oils and the like to assure that the adhesive will firm affix to the eyelid 85 properly. Failure to do so may result in separation of the heater unit near the edges rather than conforming with the eyes.

Figure 15:
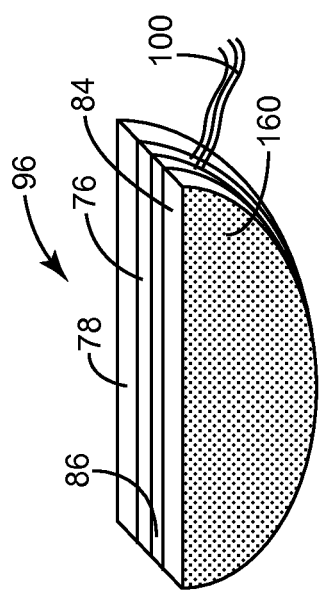

A similar embodiment to FIG. 14 is depicted in FIG. 15. In this embodiment, a temperature sensor 86 is embedded in a layer prior to or forming a part of the thermal heat sink 84. While depicted as a layer 80, the temperature sensor may be a single element temperature sensor or may be an array of temperature sensors, which detects temperature across the various segments or regions of the heating element 76. Additionally, while a single foil heating element 76 has been discussed heretofore, the heating element 76 may be realized as an array of heating elements which may be individually controlled in order to provide uniform heating to the point on the eyelid 85 where heat is directed to transfer heat to the trabecular meshwork.

Figure 16:
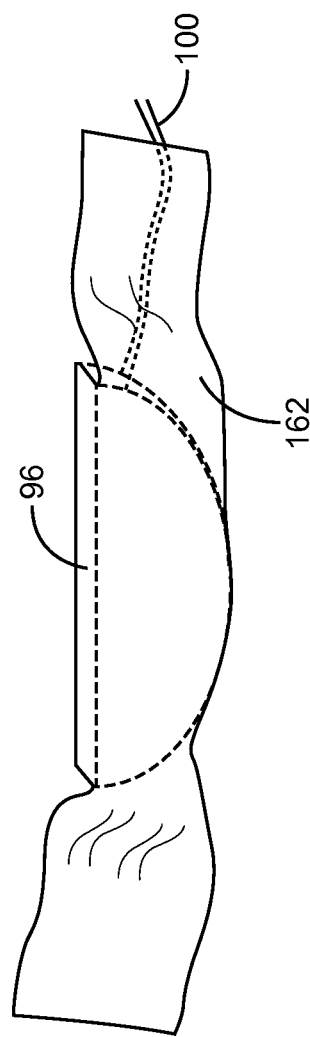

FIG. 16 depicts another embodiment consistent with embodiments of the present invention in which is a heater unit, such as any of those described heretofore 96, can be attached to the eyelid by use of a strip of adhesive tape, such as a single side adhesive medical adhesive tape 162, in order to hold the heater unit 96 in contact with the eyelid for treatment. Again, the heater unit 96 is depicted as having a relatively flat but flexible contact surface which conforms to the shape of the eyelid 85 being treated in the example illustrated. However, an eyelid conformal shape using a more rigid heat sink 84 may also be utilized without departing from embodiments consistent with the present invention.

Figure 17:
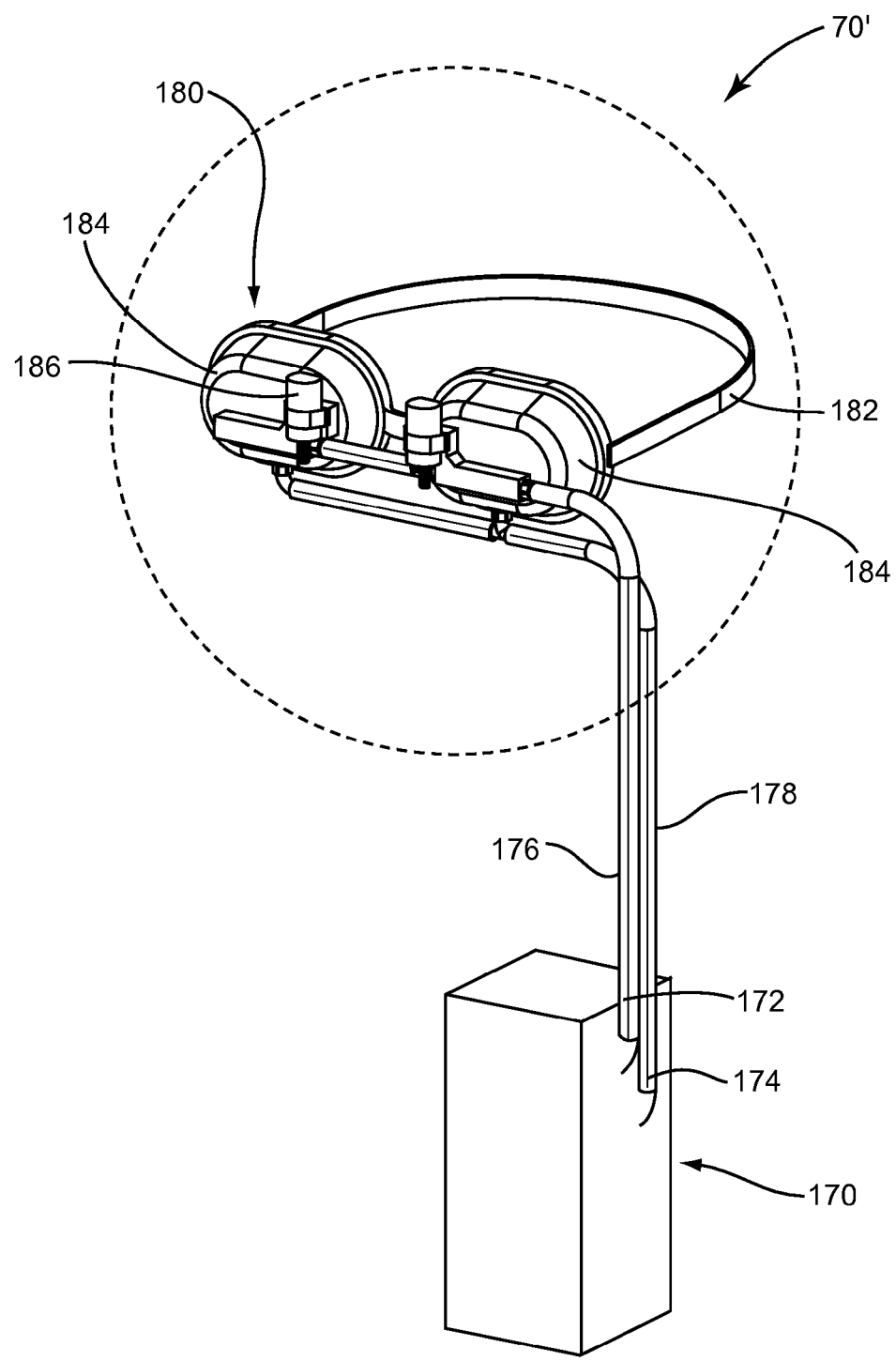
FIG. 17 is a perspective view of a trabecular meshwork heat and force application device employing goggles, according to an alternative embodiment.

Embodiments of the heat and force application device 70 can also be executed using a variety of other energy transfer devices, such as pumpable mediums, including for gases (i.e., air), other fluids or liquids (glycerin, oils, and the like), and creams. One such alternative heat and force application device 70' is illustrated in FIG. 17. As illustrated in FIGS. 17-22, the heat and force application device 70' comprises a means for applying a jet of a heated fluid to the exterior surface of the eyelid 85 towards the trabecular meshwork. The means comprises broadly a pump 170, goggles 180, and means for delivering a fluid jet to the patient's eyelid to transfer heat and force to the trabecular meshwork.

As illustrated in FIG. 17, the apparatus 70' comprises a pump 170, which may be either AC (wall plug) or DC (battery) powered (not shown). The pump 170 can be between 1/32 hp and 1/8 hp, with 1/16 hp being preferred based upon currently available data. One such pump is model STQP with pump head Q3CKC manufactured by Fluid Metering, Inc. of Syosset, N.Y. The pump 170 has respective fluid inlet and outlet ports 172, 174. Attached to the respective inlet and outlet ports 172, 174 is a conduit such as Polyester® tubing which connects to a goggle-type mask generally indicated at 180. Further, the pump 170 may be equipped with a heater (not shown) that heats the medium to the desired temperature. It will he noted that the preferred temperature of 40 degrees Celsius to 47 degrees Celsius is not the fluid temperature at the pump exit, but rather is the temperature of the fluid at the exit of a fluid delivery means 186. Thus, should the heater be located proximate the pump 170, the temperature may have to be higher in order to account for a temperature drop as the fluid travels to the goggles 180. Alternatively, the heater may be positioned on the tubing proximate the fluid inlet of goggles or mask 180 where the temperature drop would be minimal. Depending upon the type of heated medium employed and the location of the heater itself, heat may be supplied by means of conduction, convection, or radiation, as appropriate.

Figure 18:
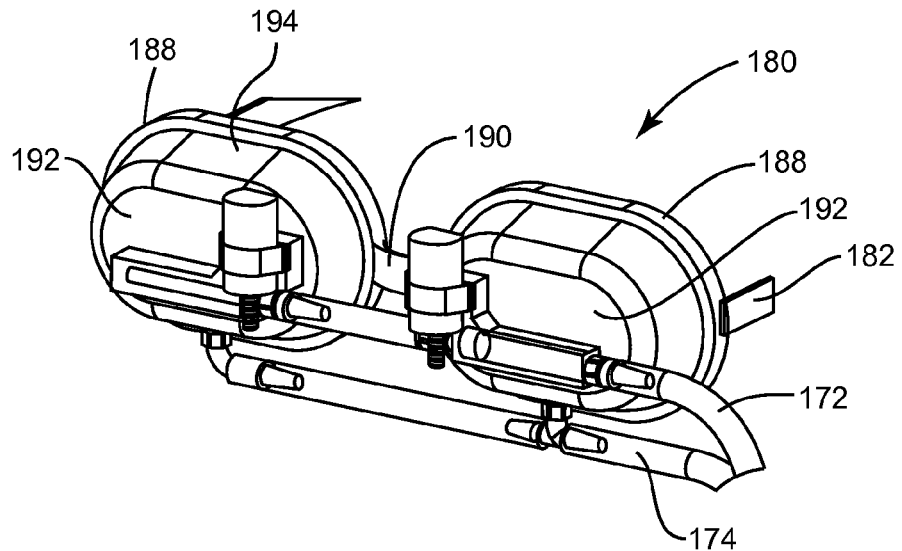
FIGS. 18-19 are front and rear perspective views of the goggles illustrated in FIG. 17.
Figure 19:
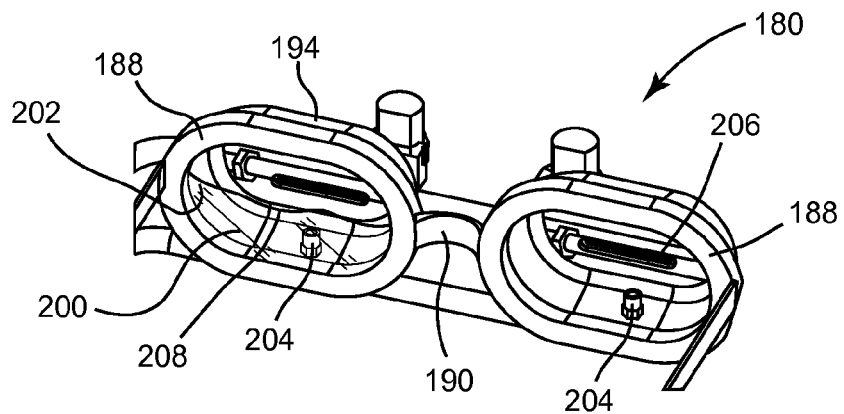

Mask 180 includes a headband 182, which is connected to the outer edges of mask eyepieces 184. Headband 182 should be fabricated from a flexible material such as rubber, but should maintain the eyepieces 184 firmly in place against the orbit and cheek areas surrounding the eye. The respective eyepieces 184 arc substantially identical in structure and function and for ease of description reference will be made to "an eyepiece" or a component thereof. Turning to FIGS. 18 and 19, the eyepiece 184 comprises an oval annulus or ring 188 of a flexible material such as rubber, plastic or neoprene of a size sufficient to cover the orbit of the eye and the eyelids and to create a seal there around. Again, although not limiting, this ring design may be preferential so that heat and/or force is directed to the circumference area of the sclera in a line towards the trabecular meshwork and outside or out of line with the pupil and iris of the eye. The respective eyepieces are connected together with a nose piece or bridge 190, which in the preferred embodiment is integrally molded with the eyepieces 184. Similarly, the nose bridge 190 may be a separately attached component, such as in conventional swim goggles. One side of the ring 188 is adapted to lie flush with the skin of the user and the opposite side is adapted to mount a lens 192 via conventional means (such as adhesive bonding or overmolding) to form a water tight seal. The techniques for lens mounting are well known to those skilled in the art. The lens 192 is integrally molded as a single clear unit and has a bottom wall 200, side walls 202, top wall 194, and front wall 208 which together define a cavity. Drain opening 204 is molded into the bottom wall 200 and front wall 208 has a slit opening 206 which mounts the means for delivering a jet of a heated medium or jet means 186, as described in greater detail herein below.

Figure 20:
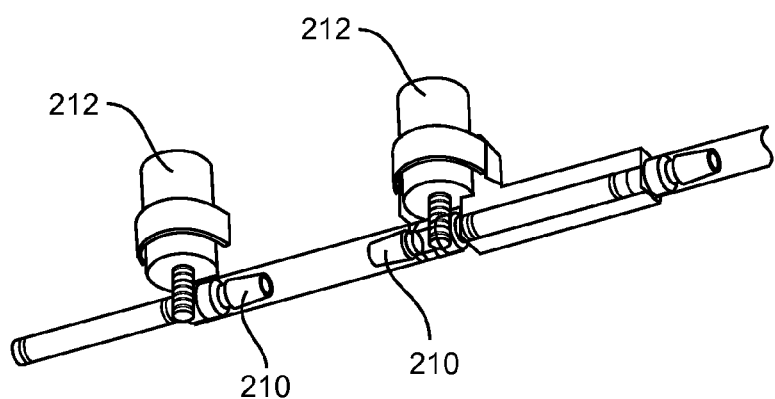
FIG. 20 is a front perspective view taken from below and showing the fluid delivery components of the trabecular meshwork heat and massaging system illustrated in FIG. 17.
Figure 21:
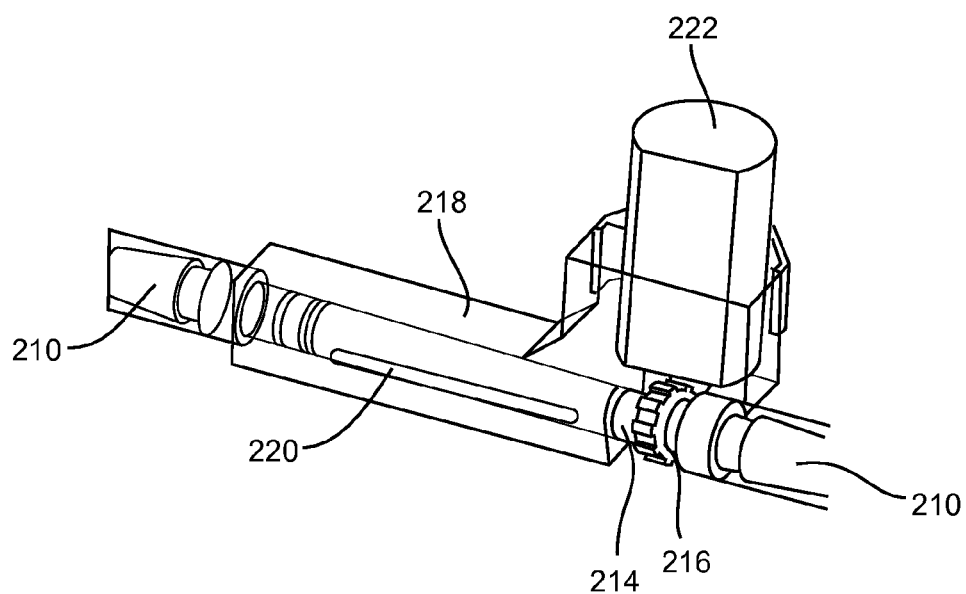
FIG. 21 is a rear perspective view of the fluid jet orifices of the trabecular meshwork heat and force application device illustrated in FIG. 17.

Turning to FIGS. 20 and 21, the jet means or rotary distributor valve 186 comprises a cylindrical manifold 214 having a bore (not shown) extending along its length. A spiral pattern of jet orifices 212 are positioned along a portion of the length of manifold 214 and each of respective orifices 212 is in fluid communication with the bore. The manifold 214 may also be equipped with a "neutral" position in which no fluid is permitted to exit the orifices 212. At one end of manifold 214 is an integrally molded gear 216 and a nipple 210 at each end. The manifold 214 is mounted for rotation between the nipples 210. One nipple 210 serves as the fluid inlet and the other serves as the fluid outlet. A housing 218 having a bore surrounds the manifold 214, which is snugly mounted for rotation therein. The housing 218 has a longitudinal slit 220, which allows fluid from the respective jet orifices 212 to pass there through such that upon rotation of the manifold, 214 the jet orifices 212 are sequentially exposed to the slit 220 and fluid is directed at the eyelid 85. A small electric or water driven motor 222 is attached to the goggles 180 such that the drive shaft thereof rotates gear 216.

In another aspect of the invention, a thin, flexible membrane 188 (shown in one eyepiece in FIG. 19, such as a plastic membrane (not shown) can be located within the goggle cavity and positioned such that when in place on the eye 12 of the patient, the membrane is substantially in contact with and covers the eyelid 85. The membrane operates to define a closed chamber into which the fluid jet is directed and which strikes the membrane. The force of the fluid jet is then transmitted through the intervening membrane and the eyelid into the trabecular meshwork to assist in loosening or relaxing protein clogs or other inhibitors to reduce IOP.

In operation, the physician or clinician would position the device, i.e., the goggles 180 over their eyes with the headband 182 extending around the head to hold the goggles 182 in place such that when the jet of the heated medium is delivered, it is applied to the exterior surface of the eyelid 85, proximate the trabecular meshwork to be treated. As previously mentioned, the goggles 180 should be firmly, but comfortably in place so as to not to move upon actuation of the apparatus. Alternatively, the device may be manually held in place against the patient's head. Upon activation of the pump 170, the heated fluid begins to move through the conduits 172, 174. During the initial start up period of the apparatus, the fluid is circulated by pump 170 and is heated to the required temperature. Once the preferred operating temperature has been reached, the motor 222 is activated and gear 216 begins to rotate, which in turn rotates the manifold 214. As the manifold 214 rotates, the jets 212 line up sequentially with the slit 220 and the fluid jet is directed to the exterior surface of the eyelid. Further, the fluid jet may also be pulsatory in nature wherein the fluid jet is intermittent. This intermittency may help to disclose some of the proteins in the trabecular meshwork 22. Other pulsatory configurations are also possible. As the manifold 214 rotates, a continuous side to side scan of the eyelid 85 with warm water jets and by allowing only one jet on each eye to be active at any instant in time, effective massage pressure is maximized, while discomfort is minimized. After the fluid has impacted the eyelid, it is collected in drain opening 204 and is drained out of the system loop.

It is believed that jet pulse frequencies of less than 300 Hz are effective. Depending upon the composition of the protein clog or other inhibitors, repeated application of the heated fluid to the trabecular meshwork may be required. The jet of the heated medium should be maintained for sufficient time to loosen or relax protein clogs or other inhibitors in the trabecular meshwork to restore the aqueous humor flow path to reduce IOP.

Figure 22:
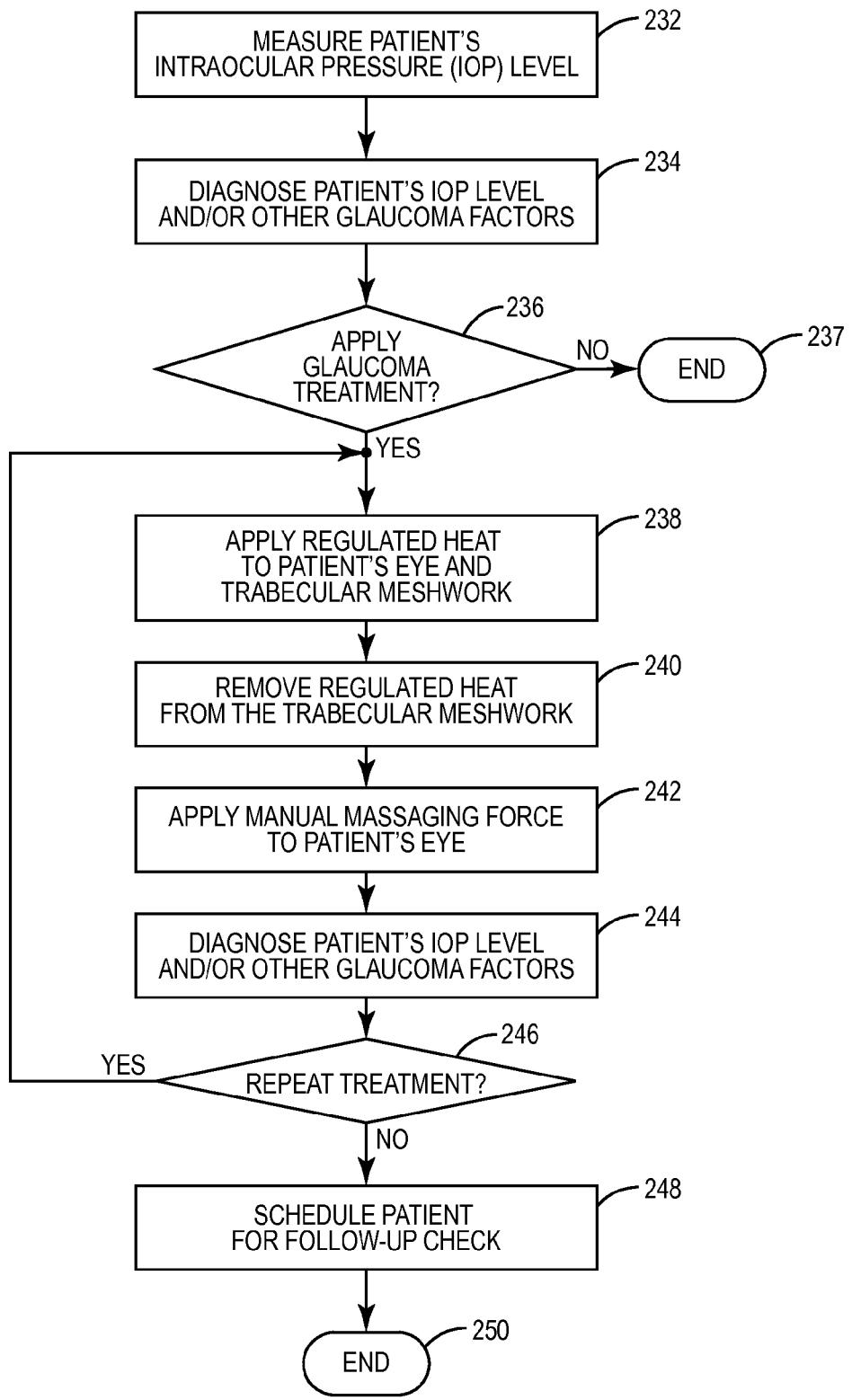
FIG. 22 is flow chart illustrating an alternative exemplary process for measuring, diagnosing, and treating elevated IOP as a symptom of open-angle glaucoma.

FIG. 22 is a flowchart illustrating the steps of an alternate embodiment of the present invention for diagnosing and treating elevated IOP in a patient as a means of either preventing or halting the effect of glaucoma to retard further vision loss. In this embodiment, regulated heat is applied to the trabecular meshwork initially without any force (other than may be caused inherently by application of a heat application device) to apply pressure to the trabecular meshwork. Instead, heat is applied, and force is applied subsequently, either manually or with a force generating device.

The process starts by a physician or certified clinician measuring the patient's IOP level to determine if an elevated or unsafe IOP exist in the patient's eye (step 232). As previously discussed with respect to FIG. 4, any technology or methodology can be used to measure IOP of a patient's eye. Next, the physician or clinician diagnoses the patient to determine if the measured IOP level is at an elevated or unsafe levels and/or other glaucoma factors exists (step 234) as previously discussed in FIG. 4.

If the patient's IOP level is determined to be at a safe level and/or other glaucoma factors exist such that treatment should not be administered (decision 236), the process ends (step 237). If on the other hand, the patient's IOP is determined to be at an elevated or unsafe level and/or other glaucoma factors are to the satisfaction of the attending physician or technician such that treatment should be administered (decision 236), treatment according to the non-invasive treatment process and apparatuses may be used to lower IOP. In this embodiment, the treatment process applies a regulated heat to the patient's trabecular meshwork in order to loosen or relax protein clogs or other inhibitors that are reducing or preventing normal outflow of aqueous humor (step 238). Any number of methods and devices may be used to apply heat to the trabecular meshwork as previously discussed and as will be discussed throughout this application. The temperature of the heat and duration of application may be applied as previously discussed.

After the desired amount of heat has been applied to the trabecular meshwork and for the desired duration, the heat application is removed from the trabecular meshwork (step 240). Thereafter, a manual application of force is applied to the eye to apply pressure to the trabecular meshwork to assist in the loosening or relaxing protein clogs or other inhibitors and reduction IOP as a result. For example, a cyclical force may be applied such that a pressure of 5 psi is applied to the trabecular meshwork. The application may also allow the temperature of the heat application and/or duration of application to be reduced from what it would otherwise be, to sufficiently loosen or relax protein clogs or other inhibitors and reduce IOP as a result. (e.g., 48 degrees Celsius temperature, at pressure of 3 psi, for duration of 30 minutes). The force may also be applied in the form of a vibratory or massaging force, to assist in the loosening or relaxing of protein clogs or other inhibitors.

The physician or clinician then measures the patient's IOP level and/or determines if glaucoma factors still exist that are unsatisfactory (step 244). The patient or physician determines if treatment should be reapplied or not during the same session based on the measured IOP level and/or these glaucoma factors (decision 246). The physician or clinician will check to see if the patient's IOP level has lowered. However, the IOP level measured still may not be low enough to be at safe levels to prevent the developed glaucoma or to retard its continued effect. If IOP level remains elevated, beyond desired levels and/or other glaucoma factors are not to the satisfaction of the physician or clinician, the physician or clinician can reapply treatment by repeating steps 238-244, as discussed above. If treatment should not continue (decision 246), treatment ends and the patient is scheduled for a follow-up visit in the future as part of monitoring the patient's IOP (step 248). It is important to continue to monitor the patient's IOP level over time to ensure that it remains lowered and/or to monitor other glaucoma factors in the patient. The present invention has been shown to sustainably lower IOP, but inevitably, IOP levels may rise again such that periodic and continued treatment should be administered.

Figure 2:
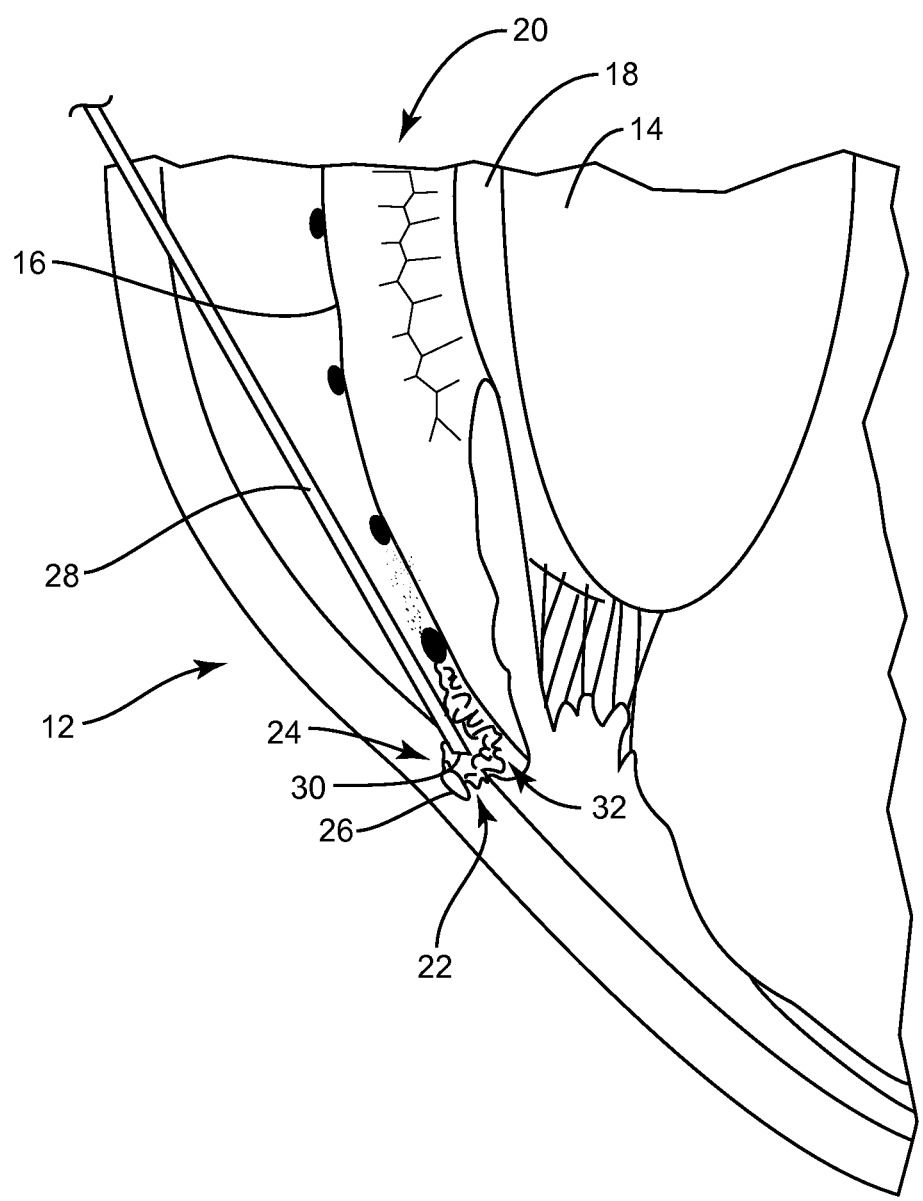
FIG. 2 is a close-up view of the lower front half of the eye illustrating opening drainage holes in the trabecular meshwork to restore drainage and reduce intraocular pressure (IOP) in the eye.
Figure 23:
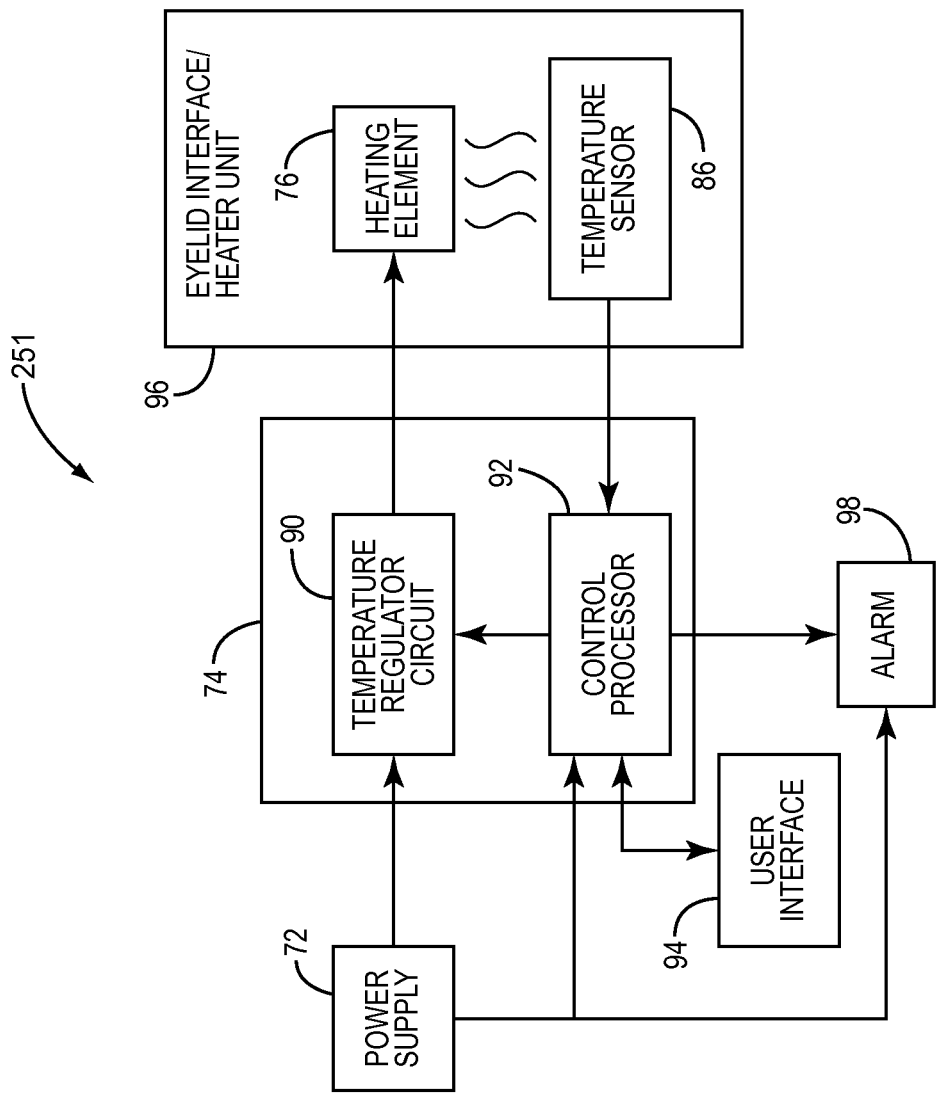
FIG. 23 is block diagram of a trabecular meshwork heating control circuit for treating open-angle glaucoma according to the exemplary process illustrated in FIG. 22.

FIG. 23 illustrates a block diagram of a heat application device 251 components that may be used in this embodiment. The block diagram is similar to the block diagram of FIG. 2, but the vibratory element 88 is not present, since a massaging force, if applied, is applied manually after the heat application device 251 is removed. All of the discussion regarding the heat generation and control aspects of the heat and force application device 70 illustrated in FIGS. 5-12 and discussed above is equally applicable to this beat application device 251 and thus will not be repeated.

Not only can beat be applied to the outside of the eyelid to transfer heat to the trabecular meshwork, but heat can also be applied to the inside of the eyelid on to the patient's eye globe to transfer heat to the trabecular meshwork. As discussed in co-pending application Ser. No. 12/015,558, it was previously unknown to apply heat to the inside of the eyelid and proximate the eye globe for other treatments not relating to glaucoma. Medical professionals would have thought it counterintuitive to apply heat to the sclera. It was thought that applying heat to the sclera would risk damage to the eyelid or the eyeball itself Previous studies of heat application to skin showed that damage could occur for temperatures at or above 45 degrees Celsius. These studies were conducted on external keratinized skin. The tissue on the inner eyelids is non-keratinized epithelium, and as such, is not as well protected from heat as keratinized skin. Thus, one would naturally believe that applying heat to the inside of the eyelid would produce a pain response at lower temperatures than on the outer eyelid surface. However, it has been surprisingly discovered that applying heat to the inside of the eyelid and the eye globe is safe if the heat is regulated, and if preferentially, the heat is applied outside the iris and pupil.

Applying heat to the eye globe outside the iris and pupil and proximate the trabecular meshwork may provide a more efficient conductive heat transfer to the trabecular meshwork. Attaining a more efficient heat transfer may allow higher temperatures to be attained at the trabecular meshwork and/or in a more efficient time to loosen or relax protein clogs. For example, it was determined that most patients can tolerate a surface temperature of 43-44.5 degrees Celsius without anesthesia and without significant pain. It was found that some patients could tolerate temperatures over 44.5 degrees Celsius without anesthesia.

Figure 24:
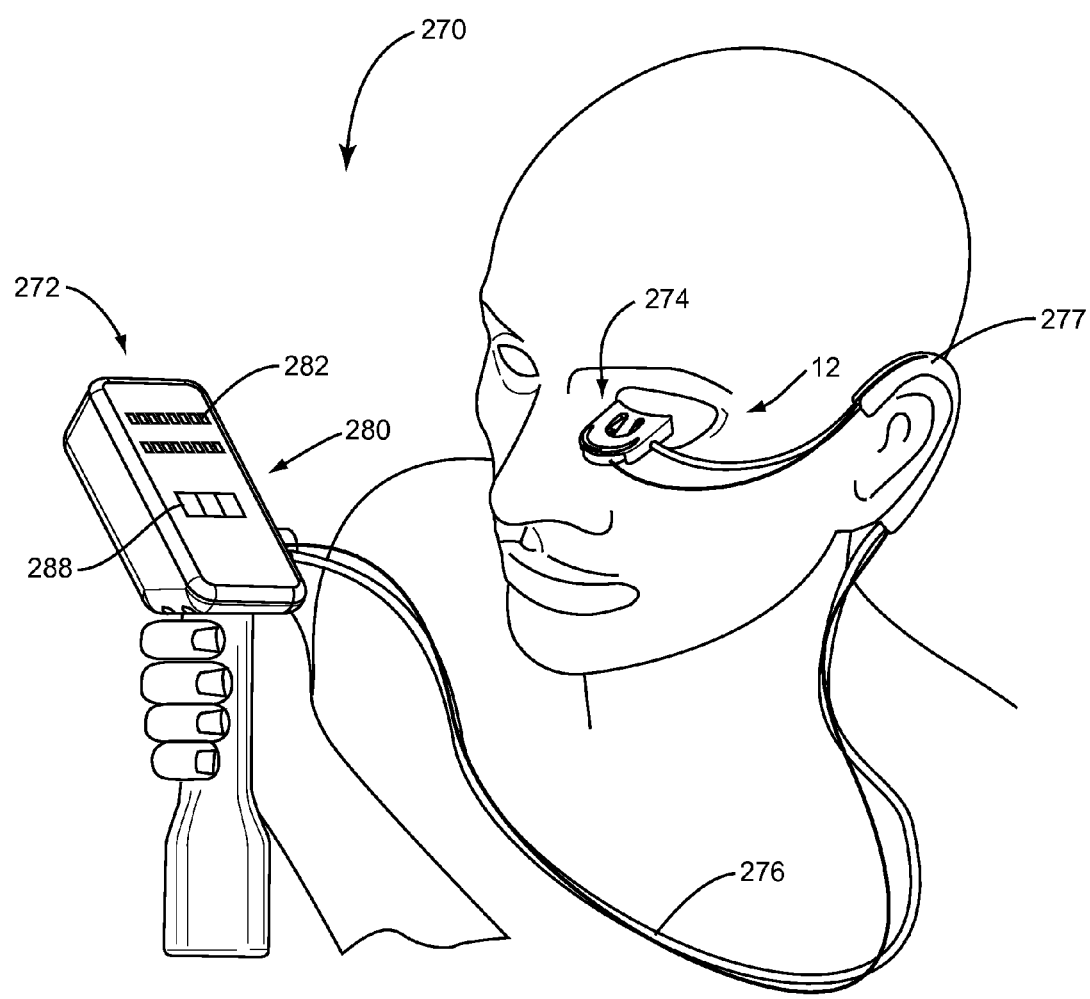
FIG. 24 illustrates a trabecular meshwork heat application device for treating open-angle glaucoma, according to an alternative embodiment.

In this regard, FIG. 24 illustrates an embodiment of a heat application device 270 that is adapted to apply heat directly to the eye globe as opposed to the patient's outer eyelid for treating elevated IOP levels. Preferably, the heating element, which will be discussed below, is designed to direct heat outside of the proximity of the patient's iris and pupil and to the sclera proximate the trabecular meshwork to direct the heat transfer primarily to the trabecular meshwork. In this embodiment, a heat application device 270 consists of a hand-held, battery-operated controller 272 that contains heat generating and regulation components. The controller 272 can also be a non hand-held device that is either mounted or rests on a table top, for example. The controller 272, as described herein, is intended to describe and encompass any device, including but not limited to electronic and pneumatic controls and supporting components, that is adapted to allow and control the application of heat to the patient's eye globe proximate the trabecular meshwork. The controller 272 is connected to a disposable component 274 to generate heat on the eye globe proximate the trabecular meshwork, as illustrated in FIG. 9. The disposable component 274 consists of a lid warmer 290 provided in the form of a lens (illustrated in FIGS. 25-27) that applies heat to the eye globe. The interface 76 wiring can be wrapped around the patient's ear 277 with any excess clipped to the patient's clothing.

The controller 272 may contain a user interface 280 to allow a physician or clinician to control the heat application device 270. Temperature being applied to the patient's eye globe can be seen on a temperature display 282. By observing temperature display 282, the physician can determine when a therapeutic temperature has been reached. For example, the temperature display 282 may be segment bar graph so that temperature level and the increasing or decreasing nature of the temperature level can be seen. The temperature level to be reached at the patient's eyelid can either be set to a static level within the controller 272, or controllable by a physician or clinician. A timer display 288 can be provided on the controller 272 to display the amount of time that heat has been applied to the patient's eye globe. The timer display 288 can display a cumulative amount of time passed or provide a countdown tinier if an initial duration is set. For example, the timer display 288 may be comprised of a number of seven segment displays.

Figure 25:
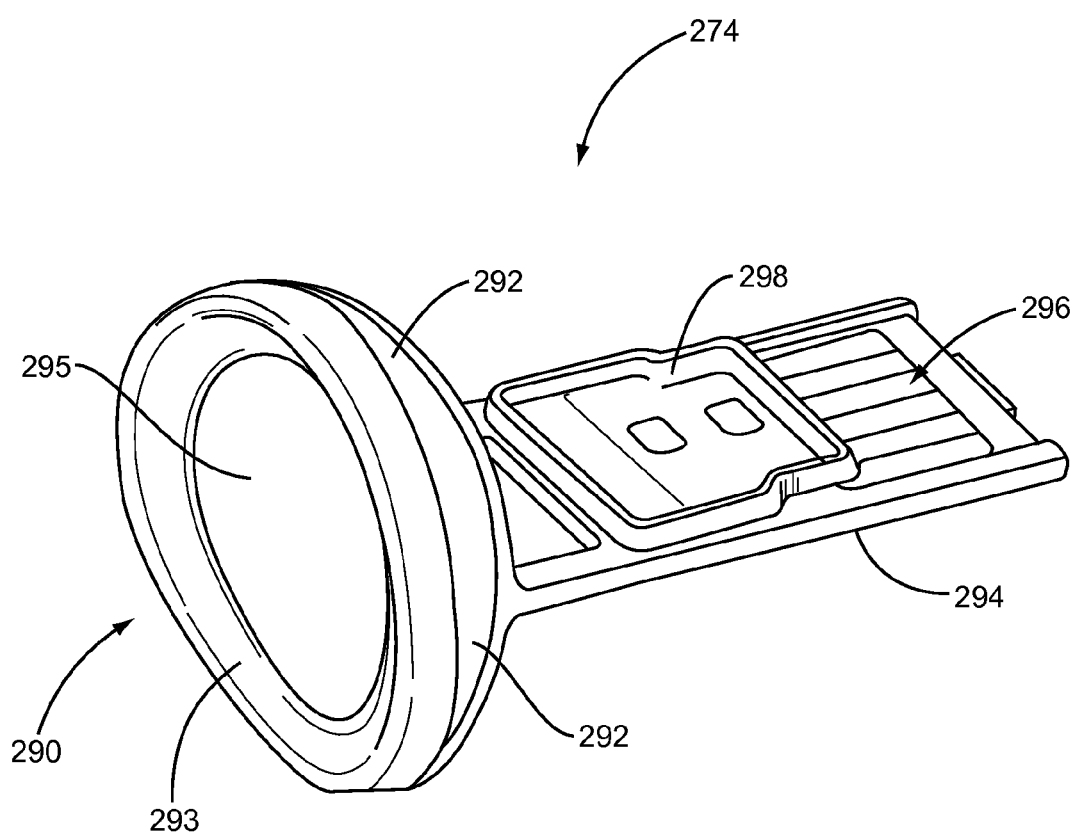
FIG. 25 illustrates a heating application component of the trabecular meshwork heat application device illustrated in FIG. 24.
Figure 26:
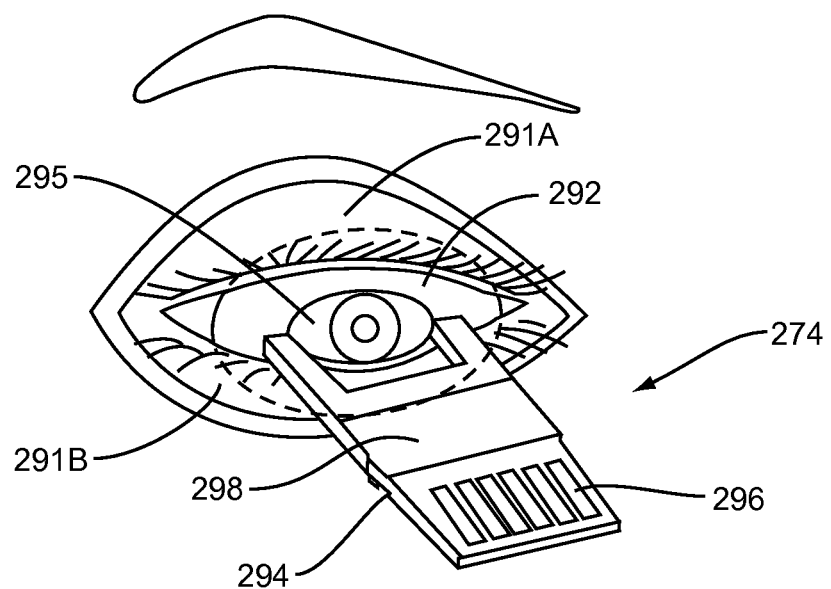
FIG. 26 illustrates the process of placing the heat application component illustrated in FIG. 25 on the patient's eye inside the eyelid to apply heat to the trabecular meshwork.

FIG. 25 illustrates the disposable component 274 in more detail. The disposable component 274 consists of a lid warmer 290 that includes a lens in the disclosed embodiment. The lens 290 contains a heating clement (illustrated in FIG. 27) to apply heat to a patient's eye globe. Preferably, the heating element is positioned in the lens 290 such that when the lens 290 is installed, the heating element, is outside of the proximity of the patient's iris and pupil to direct heat transfer to the trabecular meshwork and away from the iris and pupil. An insulator (shown in FIG. 27) may be included to insulate the heating element from inside of the patient's eyelid. As illustrated in FIG. 26, the lens 290 is placed on the patient's eye globe with the patient's upper and lower eyelids 291A, 291B resting on the outside surface of the lens 290. Before installation, the scleral side of lens 290 may be lubricated with saline, or equivalent lubricating drops. The lens 290 is then inserted onto the patient's eye under the eyelids 291A, 291B. The heating element 306 (illustrated in FIG. 27) is contained within the lens 290 that can apply heat to the patient's eye globe to be transferred to the trabecular meshwork when installed. The material used to construct the lens 290 is not electrically conductive, but is thermally conductive to allow heat from the heating element inside to be transferred to the patients eyelid. The lens 290 can be constructed out of a plastic, including a clear plastic such as LEXAN HPS2 for example. Further, the lens 290 can be constructed from a biocompatible material, such as polymethylmethacrylate (PMMA), epoxy, or other materials well known to those skilled in the art. The lens 290 may be flexible, but ideally should be only minimally compressible to fit against the patients eyeball.

The lens 290 also contains a lid warmer platform or tab 294 that is attached to the lens 290. The lid warmer platform 294 may be connected perpendicularly to the lens 290 such that it extends away from the patient's eye when installed. The lid warmer platform 294 provides a handle for insertion and movement or adjustment of the lens 290 and its heating element. It can also support a lens electrical interface 296 to allow the lens 290 to electrically connect the heating element inside the lens 290 to the controller 272 via the interface 276. The controller 272 can then apply electrical energy to the heating element to generate heat within the lens 290 and thus to the inside of the patient's eyelid when installed. Second, it provides a support structure for interface circuitry 298. The interface circuitry 298 provides electrical connections for energizing the heating element and communicating temperature measured at the lens 290 back to the controller 272 for heat regulation. A heat regulating circuit like that previously illustrated and discussed may be employed.

Figure 27:
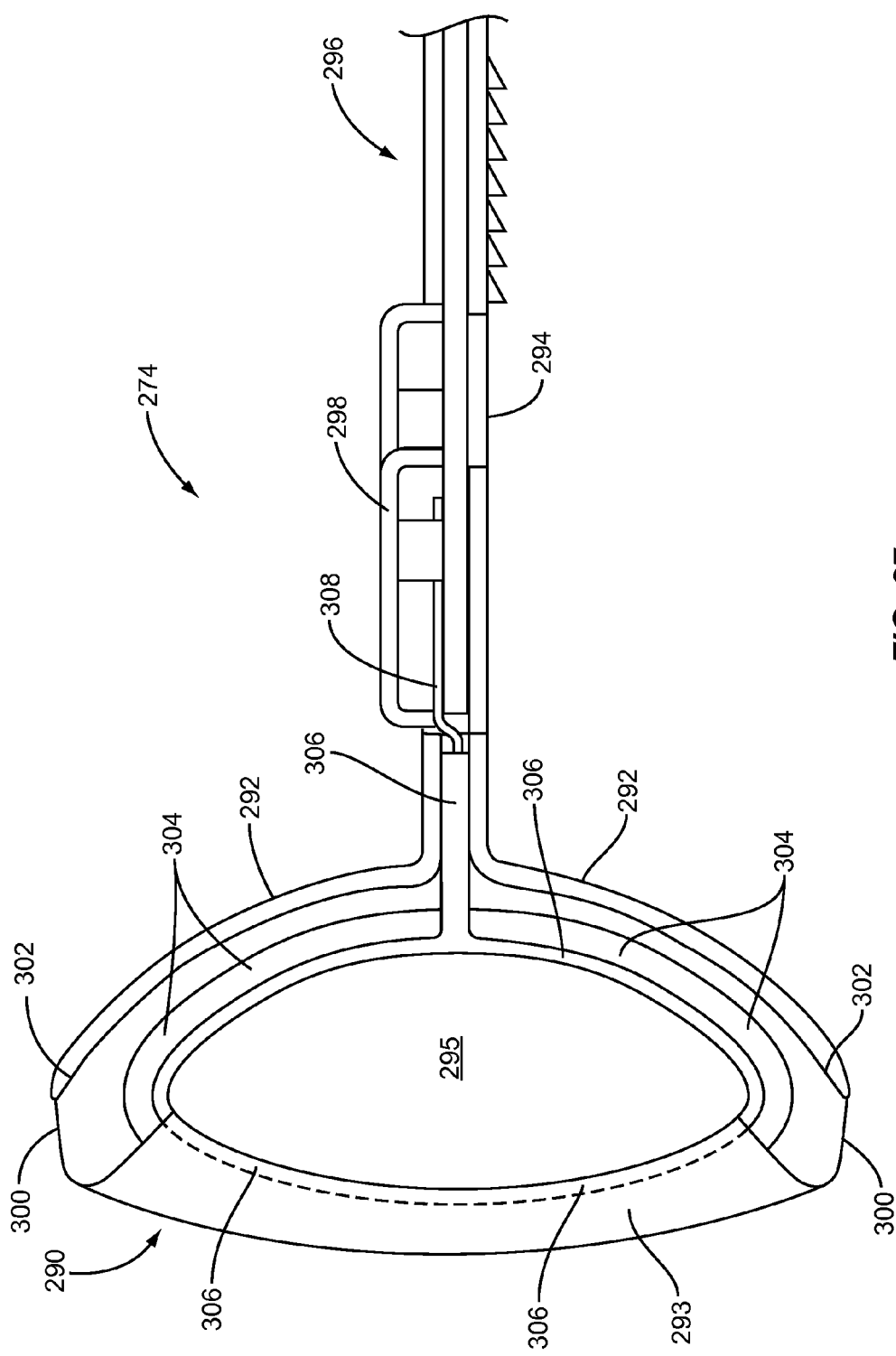
FIG. 27 illustrates a cross-sectional view of the heat application component illustrated in FIGS. 25-26.

FIG. 27 illustrates a cross-sectional view of the lid warmer employing the lens 290 illustrated in FIGS. 24-26 to further illustrate heat delivery components and features of the lid warmer, according to this embodiment. The lens 290 is formed by a donut-shaped scleral side 293 being attached to an eyelid side 292. The scleral side 293 contains an orifice 295 so that the heating element 306 is located around the perimeter of the eye away from the cornea and towards the trabecular meshwork 22 The scleral side 293 of the lens 290 contains a bend 300 around its circumference edge to provide an attachment edge 302 to support attachment of the eyelid side 292. Because of the bend 300, a hollow chamber 304 is formed inside the lens 290. The heating element 306 abuts against the scleral side 293 of the lens 290 so that the heat is generated adjacent the eye globe to transfer the heat to the trabecular meshwork 22. The hollow chamber 304 insulates the cornea from the heating element 306 contained inside the lens 290. The heating element 306 is attached to the interface circuitry 298 via a fused link 308, which is then attached to the controller 272 via the lid warmer platform 294 being attached to the controller interface 276. In this manner, the controller 272 can cause the heating element 306 inside the lens 290 to generate heat by applying an electrical signal to the interface circuitry 298, which is connected to the heating element 306. If the temperature exceeds the threshold temperature level of the fused link 308, the link 308 would melt and create an open circuit to disable the heating element 306 for safety reasons. Alternatively, the fused link 308 could be a thermal link provided as an integrated part of the heating element 306 such that the fused link 308 would melt and create an open circuit at a given threshold temperature.

The heating element 306 may be provided in any form or material. The heating element 306 may be a resistive type heater, a thick film heater, or any one of a number of other types, such as a "flex circuit" (etched metal on flexible substrate) well known to those skilled in the art. The heating element 306 can be formed to the shape of the lens 290. In the illustrated example, the heating element 306 is a material that is both electrically and thermally conductive. This may be important. The electrical conductivity characteristic allows current to be applied to the heating element 306 to generate resistive heat. The thermal conductivity characteristic serves to evenly distribute the resistive heat over the entire heating element 306 to more evenly distribute the heat to the patient's eyelid. Without these characteristics, it may be more difficult to regulate heat generated by the heating element to efficiently and effectively loosen or relax protein clogs or other inhibitors in the trabecular meshwork.

Examples include the E5101 carbon-loaded polyphenylene sulfide and the E2 liquid crystal polymer, both manufactured by Cool Polymers, Inc.

The size of the lens 290 may also play a part in the heating element 306 selection and the amount of heat it must generate to be effective. The lens 290 distributes heat generated by the heating element 306. A larger lens 290 may distribute the heat generated by the heating element 306 more uniformly and over a larger surface area. Also note that the application of heat to the patient's eye globe does not necessarily have to include an embedded heating element 306 in the lens 290. Heat application may be provided as part of the environment, such as air for example. The amount of heat applied, the temperature reached at the trabecular meshwork as a result, where the heat is applied on the patient's eyelid or surrounding tissue, and the duration of heat applied can control the selection of the heating source.

In addition to the insulation provided by the material used to construct the lens 290, the lens 290 may also contain an integrated insulator inside the chamber 304 as an additional measure of insulation. Insulation prevents substantial heat from reaching the inner cornea. As employed herein, the term "insulate" or "insulation" is intended to include any component or material and/or specific geometries of components or materials, wherein there is greater resistance to thermal conduction or radiation towards the surface of the eye than towards the eyelid. Stated alternatively, in the insulator thermal energy radiates more easily towards the eye globe that the eyelids 291A, 291B. Although not necessary, this may assist in greater comfort to the patient during treatment. In the lens 290 example of FIG. 27, the integrated insulator is air and is formed by the hollow chamber 304 that exists by the space left by the heating element 306 not filling up the entire volume of the hollow chamber 304. Further, the hollow chamber 304 may be provided in the form a biocompatible material such as polymethylmethacrylate (PMMA), epoxy, or other materials well known to those skilled in the art. The hollow chamber 304 may be flexible, but ideally should be only minimally compressible, as will become clear from the discussion that follows. The heating element 306 is biased according to its location in the lens 290, and in particular to be located behind the integrated insulator, to produce heat towards the eye globe the trabecular meshwork.

Figure 28:
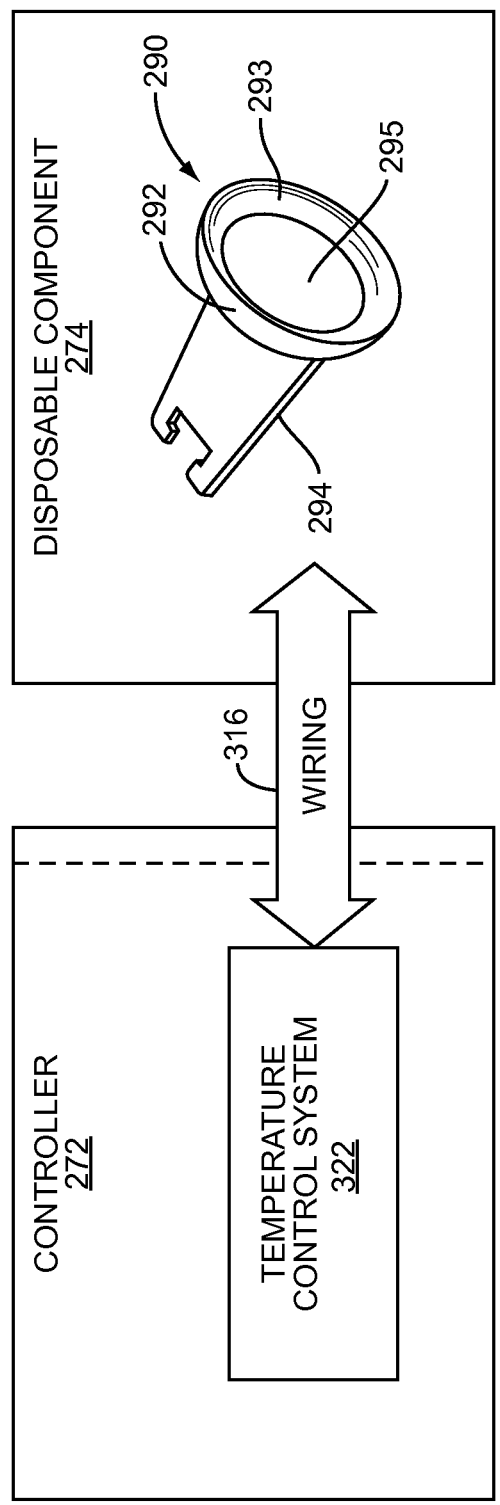
FIG. 28 illustrates a system diagram of temperature control and communication components of the trabecular meshwork heating device illustrated in FIGS. 24-27.

FIG. 28 supplements FIG. 27 to illustrate the interface components between the controller 272 and the disposable component 274 at a system level. The controller 272 of the heat and force application device 270 contains a temperature control system 322, which is wired via wiring 316 to the disposable component 274. The temperature control system 322 is the control component within the controller 272 that controls the heat applied to the patient's eye via the lens 290. The temperature control system 322 may operate similarly or just as the heating regulating circuit 74, previously described above.

Those skilled in the art will recognize improvements and modifications to the preferred embodiments of the present invention. All such improvements and modifications are considered within the scope of the concepts disclosed herein and the claims that follow.

What is claimed is:

1. A method of lowering a patient's intraocular pressure, comprising the steps of:
   measuring an intraocular pressure level of a patient's eye;
   transferring a regulated heat from a heating device to a trabecular meshwork of the patient's eye to provide a temperature level at the trabecular meshwork sufficient to loosen or relax one or more clogs in the trabecular meshwork to improve or restore an outflow path for aqueous humor through the trabecular meshwork;
   maintaining the regulated heat transfer to the trabecular meshwork for a period of time sufficient to loosen or relax the one or more clogs in the trabecular meshwork to improve or restore the outflow path for aqueous humor through the trabecular meshwork;
   preferentially directing a force to a circumference area of the patient's sclera in a line towards the trabecular meshwork, wherein preferentially directing the force to the circumference area of the patient's sclera in a line towards the trabecular meshwork comprises preferentially directing the force to the circumference area of the sclera in a line towards the trabecular meshwork and outside or out of line with a pupil and an iris; and
   wherein the steps of transferring the regulated heat and maintaining the regulated heat transfer are performed based on the intraocular pressure level in the patient's eye.

2. The method of claim 1, wherein transferring the regulated heat to the trabecular meshwork comprises transferring the regulated heat through the sclera and a cornea of the patient's eye and to the trabecular meshwork.

3. The method of claim 2, wherein transferring the regulated heat to the trabecular meshwork comprises directing the regulated heat in a direction in line with the trabecular meshwork and out of line with the iris and the pupil of the patient's eye.

4. The method of claim 2, further comprising measuring the intraocular pressure level of the patient's eye after performing the steps of transferring the regulated heat and maintaining the regulated heat transfer.

5. The method of claim 1, wherein the measuring the intraocular pressure level of the patient's eye is performed prior to a first time the steps of transferring the regulated heat and maintaining the regulated heat transfer are performed.

6. The method of claim 5, further comprising:
   diagnosing the intraocular pressure level in the patient's eye; and
   performing the steps of transferring the regulated heat and maintaining the regulated heat transfer based on the diagnosing of the intraocular pressure level in the patient's eye.

7. The method of claim 1, further comprising measuring the intraocular pressure level of the patient's eye after performing the steps of transferring the regulated heat and maintaining the regulated heat transfer.

8. The method of claim 1, further comprising discontinuing the transfer of the regulated heat to the trabecular meshwork.

9. The method of claim 8, further comprising, after the step of discontinuing the transfer of the regulated heat to the trabecular meshwork:
   measuring the intraocular pressure level of the patient's eye;
   diagnosing the intraocular pressure level in the patient's eye; and
   determining if the steps of transferring the regulated heat and maintaining the regulated heat transfer should be performed again based on the diagnosis.

10. The method of claim 1, wherein the period of time is between 10 and 120 minutes.

11. The method of claim 1, wherein the temperature level of the regulated heat transfer is such that the regulated heat reaching the trabecular meshwork is above body temperature.

12. The method of claim 11, wherein the temperature level of the regulated heat reaching the trabecular meshwork is between approximately 40 to 44 degrees Celsius.

13. The method of claim 1, wherein the transferring the regulated heat further comprises applying heat to an outer eyelid of the patient's eye such that the heat is transferred through the outer eyelid and through the sclera and lens of the patient's eye to the trabecular meshwork.

14. The method of claim 13, wherein the temperature of the heat applied to the outer eyelid of the patient's eye is between approximately 40 and 48 degrees Celsius.

15. The method of claim 1, wherein the transferring the regulated heat further comprises applying the regulated heat to the sclera of the patient's eye such that the regulated heat is transferred through the sclera and a cornea of the patient's eye to the trabecular meshwork.

16. The method of claim 15, wherein the temperature level of the regulated heat applied to the sclera of the patient's eye is between approximately 38 and 45 degrees Celsius.

17. The method of claim 1, wherein the preferentially directed force assists in loosening or relaxing the one or more clogs in the trabecular meshwork to improve or restore the outflow path for aqueous humor through the trabecular meshwork.

18. The method of claim 17, wherein the preferentially directed force is directed to the circumference area of the patient's sclera in a line towards the trabecular meshwork for a period of time.

19. The method of claim 18, wherein the period of time is between approximately 10 and 120 minutes.

20. The method of claim 17, wherein the preferentially directed force is applied simultaneously with the regulated heat transfer.

21. The method of claim 17, wherein the preferentially directed force is applied after discontinuing the transfer of the regulated heat to the trabecular meshwork.

22. The method of claim 1, wherein the preferentially directed force is a massaging force.

23. The method of claim 1, wherein the transferring the regulated heat to the trabecular meshwork further comprises transferring diffuse heat to the trabecular meshwork.

24. The method of claim 1, wherein the transferring the regulated heat further comprises applying the regulated heat between an inner surface of the patient's eyelid and eyeball such that the regulated heat is transferred to the trabecular meshwork.

25. The method of claim 1, wherein the preferentially directed force is a milking force.

* * * * *